US007955795B2

(12) United States Patent
Kumar

(10) Patent No.: US 7,955,795 B2
(45) Date of Patent: Jun. 7, 2011

(54) METHOD OF WHOLE GENOME AMPLIFICATION WITH REDUCED ARTIFACT PRODUCTION

(75) Inventor: Gyanendra Kumar, Guilford, CT (US)

(73) Assignee: QIAGEN GmbH, Hilden (DE)

( * ) Notice: Subject to any disclaimer, the term of this patent is extended or adjusted under 35 U.S.C. 154(b) by 650 days.

(21) Appl. No.: 10/456,056

(22) Filed: Jun. 6, 2003

(65) Prior Publication Data
US 2004/0248105 A1    Dec. 9, 2004

(51) Int. Cl.
*C12Q 1/68* (2006.01)
(52) U.S. Cl. .......................................................... 435/6
(58) Field of Classification Search .................. None
See application file for complete search history.

(56) References Cited

U.S. PATENT DOCUMENTS

| | | | |
|---|---|---|---|
| 3,687,808 A | 8/1972 | Merigan et al. | |
| 4,748,111 A | 5/1988 | Dattagupta et al. | |
| 4,965,188 A | 10/1990 | Mullis et al. | |
| 5,001,050 A | 3/1991 | Blanco et al. | |
| 5,043,272 A | 8/1991 | Hartley | |
| 5,106,727 A | 4/1992 | Hartley et al. | |
| 5,130,238 A | 7/1992 | Malek et al. | |
| 5,198,543 A | 3/1993 | Blanco et al. | |
| 5,262,311 A | 11/1993 | Pardee et al. | |
| 5,409,818 A | 4/1995 | Davey et al. | |
| 5,455,166 A | 10/1995 | Walker et al. | |
| 5,459,038 A * | 10/1995 | Reed et al. .................... 435/6 |
| 5,523,204 A | 6/1996 | Singer et al. | |
| 5,538,871 A | 7/1996 | Nuovo et al. | |
| 5,539,082 A | 7/1996 | Nielsen et al. | |
| 5,547,843 A | 8/1996 | Studier et al. | |
| 5,563,037 A | 10/1996 | Sutherland et al. | |
| 5,573,907 A | 11/1996 | Carrino et al. | |
| 5,593,836 A | 1/1997 | Niemiec et al. | |
| 5,614,390 A | 3/1997 | McCaslin et al. | |
| 5,629,158 A | 5/1997 | Uhlen | |
| 5,629,179 A | 5/1997 | Mierendorf et al. | |
| 5,639,599 A | 6/1997 | Ryder et al. | |
| 5,648,245 A | 7/1997 | Fire et al. | |
| 5,691,136 A | 11/1997 | Lupski et al. | |
| 5,714,331 A | 2/1998 | Buchardt et al. | |
| 5,719,262 A | 2/1998 | Buchardt et al. | |
| 5,736,365 A | 4/1998 | Walker et al. | |
| 5,792,607 A | 8/1998 | Bachman et al. | |
| 5,824,517 A * | 10/1998 | Cleuziat et al. ............. 435/91.2 |
| 5,854,033 A | 12/1998 | Lizardi | |
| 5,856,096 A | 1/1999 | Windle et al. | |
| 5,866,336 A | 2/1999 | Nazarenko et al. | |
| 5,876,924 A | 3/1999 | Zhang et al. | |
| 5,891,636 A | 4/1999 | Van Gelder et al. | |
| 5,925,517 A | 7/1999 | Tyagi et al. | |
| 5,942,391 A | 8/1999 | Zhang et al. | |
| 6,001,611 A | 12/1999 | Will | |
| 6,027,923 A | 2/2000 | Wallace | |
| 6,033,881 A | 3/2000 | Himmler et al. | |
| 6,096,880 A | 8/2000 | Kool | |
| 6,117,635 A | 9/2000 | Nazarenko et al. | |
| 6,124,120 A * | 9/2000 | Lizardi ........................ 435/91.2 |
| 6,140,055 A | 10/2000 | Todd et al. | |
| 6,143,495 A | 11/2000 | Lizardi et al. | |
| 6,183,960 B1 | 2/2001 | Lizardi | |
| 6,210,884 B1 | 4/2001 | Lizardi | |
| 6,214,587 B1 | 4/2001 | Dattagupta et al. | |
| 6,221,603 B1 | 4/2001 | Mahtani | |
| 6,242,188 B1 | 6/2001 | Dattagupta et al. ................ 435/6 |
| 6,255,082 B1 | 7/2001 | Lizardi et al. | |
| 6,280,949 B1 | 8/2001 | Lizardi | |
| 6,287,768 B1 | 9/2001 | Chenchik et al. | |
| 6,287,776 B1 | 9/2001 | Hefti | |
| 6,288,220 B1 | 9/2001 | Kambara et al. | |
| 6,291,187 B1 | 9/2001 | Kingmore et al. | |
| 6,291,193 B1 | 9/2001 | Khodadoust et al. | |
| 6,291,669 B1 | 9/2001 | Kwiatkowski et al. | |
| 6,294,664 B1 | 9/2001 | Ravikumar et al. | |

(Continued)

FOREIGN PATENT DOCUMENTS

AU    10240/97    11/1996

(Continued)

OTHER PUBLICATIONS

Tabor et al. ("Effect of manganese ions on the incorporation of dideoxynucleotides by bacteriophage T7 DNA polymerase and *Escherichia coli* DNA polymerase I" Proc Natl Acad Sci U S A. Jun. 1989;86(11):4076-80.*

(Continued)

*Primary Examiner* — Christopher M. Babic
(74) *Attorney, Agent, or Firm* — Ballard Spahr LLP

(57) ABSTRACT

Disclosed are compositions and methods for amplification of nucleic acid sequences of interest with greater efficiency and fidelity. The disclosed method relates to isothermal amplification techniques, such as Multiple Displacement Amplification (MDA), where the generation of DNA artifacts is decreased or eliminated. Generally, this can be accomplished by carrying out the reaction at elevated temperature. In particularly useful embodiments of the method, sugars and/or other additives can be used to stabilized the polymerase at high temperature. It has been discovered that generation of high molecular weight artifacts, in an isothermal amplification procedure, is substantially reduced or eliminated while still allowing the desired amplification of input DNA by carrying out the reaction at a higher temperature and, optionally, in the presence of one or more additives. It also has been discovered that isothermal amplification reactions can produce amplification products of high quality, such as low amplification bias, if performed at a higher temperature and, optionally, in the presence of one or more additives.

28 Claims, 2 Drawing Sheets

U.S. PATENT DOCUMENTS

| | | | |
|---|---|---|---|
| 6,297,006 B1 | 10/2001 | Drmanac et al. | |
| 6,300,073 B1 * | 10/2001 | Zhao et al. | 435/6 |
| 6,316,229 B1 | 11/2001 | Lizardi et al. | 435/91.1 |
| 6,323,009 B1 * | 11/2001 | Lasken et al. | 435/91.1 |
| 6,329,150 B1 | 12/2001 | Lizardi et al. | |
| 6,344,329 B1 | 2/2002 | Lizardi | |
| 6,361,940 B1 | 3/2002 | Van Ness et al. | |
| 6,479,235 B1 | 11/2002 | Schumm et al. | 435/6 |
| 6,617,137 B2 | 9/2003 | Dean et al. | |
| 6,632,609 B2 | 10/2003 | Lizardi | |
| 6,642,034 B2 | 11/2003 | Lizardi | |
| 6,703,228 B1 | 3/2004 | Landers et al. | 435/91.2 |
| 6,706,519 B1 | 3/2004 | Kellogg et al. | 435/287.2 |
| 6,797,474 B2 | 9/2004 | Lizard | 435/6 |
| 6,830,884 B1 | 12/2004 | Hafner et al. | 435/6 |
| 6,977,148 B2 | 12/2005 | Dean et al. | 435/6 |
| 7,074,600 B2 | 7/2006 | Dean et al. | 435/91.2 |
| 7,297,485 B2 | 11/2007 | Bornarth et al. | 435/6 |
| 7,358,047 B2 | 4/2008 | Hafner et al. | 435/6 |
| 7,618,776 B2 | 11/2009 | Lizard | 435/6 |
| 2002/0192649 A1 | 12/2002 | Lizardi | |
| 2003/0008313 A1 | 1/2003 | Wiltshire | |
| 2003/0152932 A1 | 8/2003 | Kumar | |
| 2003/0175788 A1 | 9/2003 | Alsmadi | |
| 2003/0207267 A1 | 11/2003 | Lasken | |
| 2003/0235849 A1 | 12/2003 | Lizardi | |
| 2004/0063144 A1 | 4/2004 | Lizardi | |
| 2004/0091857 A1 | 5/2004 | Nallur | |
| 2004/0121338 A1 | 6/2004 | Alsmadi | |
| 2004/0126764 A1 | 7/2004 | Lasken | |
| 2004/0191784 A1 | 9/2004 | Abarzua | |
| 2004/0248103 A1 | 12/2004 | Feaver | |
| 2004/0265897 A1 | 12/2004 | Lizardi | |
| 2005/0025773 A1 | 2/2005 | Shao | |
| 2006/0166227 A1 | 7/2006 | Kingsmore | |
| 2006/0188893 A1 | 8/2006 | Kumar | |
| 2007/0015182 A1 | 1/2007 | Abarzua | |
| 2008/0057543 A1 | 3/2008 | Korfhage | |
| 2008/0096258 A1 | 4/2008 | Korfhage | |
| 2008/0128298 A1 | 6/2008 | Bornarth | |

FOREIGN PATENT DOCUMENTS

| | | |
|---|---|---|
| AU | 5850996 | 11/1996 |
| AU | 97915/98 | 10/1998 |
| AU | 27819/00 | 12/1999 |
| AU | 200253328 | 6/2000 |
| AU | 18040/01 | 11/2000 |
| AU | 2001/251359 | 4/2001 |
| AU | 2001255331 | 4/2001 |
| AU | 2001268725 | 6/2001 |
| AU | 2001269944 | 6/2001 |
| AU | 2001271722 | 7/2001 |
| AU | 2002/239809 | 1/2002 |
| AU | 2002362874 | 10/2002 |
| AU | 2003297891 | 12/2003 |
| BE | 96940601.6 | 11/1996 |
| CA | 2236161 | 11/1996 |
| CA | 2308004 | 10/1998 |
| CA | 2394800 | 12/1999 |
| CA | 2360342 | 11/2000 |
| CA | 2405456 | 4/2001 |
| CA | 2405687 | 4/2001 |
| CA | 2410951 | 6/2001 |
| CA | 2411838 | 6/2001 |
| CA | 2411794 | 7/2001 |
| CA | PCT/US02/00005 | 1/2002 |
| CA | 2463933 | 10/2002 |
| CA | 2512196 | 12/2003 |
| CH | 96940601.6 | 11/1996 |
| CN | 01811542 | 6/2001 |
| DE | 862656 | 11/1996 |
| DE | 1946712.5 | 6/2001 |
| DE | 1950759.9 | 7/2001 |
| DK | 96940601.6 | 11/1996 |
| EP | 0 070 685 B1 | 7/1982 |
| EP | 0 356 021 | 2/1990 |
| EP | 0 466 520 | 7/1991 |
| EP | 96940601.6 | 11/1996 |
| EP | 0 745 690 | 12/1996 |
| EP | 0 866 071 A2 | 3/1998 |
| EP | 98952147.1 | 10/1998 |
| EP | 99935725.4 | 7/1999 |
| EP | 99969209.8 | 12/1999 |
| EP | 938263.1 | 6/2000 |
| EP | 980827 | 11/2000 |
| EP | 1924731.1 | 4/2001 |
| EP | 1928481.9 | 4/2001 |
| EP | 1946712.5 | 6/2001 |
| EP | 1948505.1 | 6/2001 |
| EP | 1950759.9 | 7/2001 |
| EP | 2705674.6 | 1/2002 |
| EP | 2801776.2 | 10/2002 |
| EP | 3796961.5 | 12/2003 |
| EP | 7118804.9 | 10/2007 |
| FR | 96940601.6 | 11/1996 |
| FR | 1946712.5 | 6/2001 |
| GB | 96940601.6 | 11/1996 |
| GB | 1946712.5 | 6/2001 |
| GB | 1950759.9 | 7/2001 |
| HK | 1100606.5 | 1/2001 |
| IE | 96940601.6 | 11/1996 |
| IL | 153097 | 6/2001 |
| IT | 1946712.5 | 6/2001 |
| JP | 42 262 799 | 9/1992 |
| JP | 0 505 012 | 10/1992 |
| JP | 04 304 900 | 10/1992 |
| JP | 9-519942 | 11/1996 |
| JP | 2000-515033 | 10/1998 |
| JP | 2000-588388 | 12/1999 |
| JP | 469290-19 | 6/2000 |
| JP | 469290-68 | 11/2000 |
| JP | 2001-575244 | 4/2001 |
| JP | 2001-577404 | 4/2001 |
| JP | 2002-503102 | 6/2001 |
| JP | 2002-508032 | 7/2001 |
| JP | 2004-565385 | 12/2003 |
| JP | 2002/506247 | 6/2007 |
| JP | 2007-276942 | 10/2007 |
| LU | 96940601.6 | 11/1996 |
| MC | 96940601.6 | 11/1996 |
| NL | 96940601.6 | 11/1996 |
| SE | 96940601.6 | 11/1996 |
| SG | 200207285-8 | 6/2001 |
| TW | 90114960 | 6/2001 |
| TW | 91102150 | 2/2002 |
| WO | WO 91/08307 | 3/1991 |
| WO | WO 92/01813 | 2/1992 |
| WO | WO 94/24312 | 10/1994 |
| WO | WO 95/03430 | 2/1995 |
| WO | WO 95/03432 | 2/1995 |
| WO | WO 95/22623 | 8/1995 |
| WO | WO 95/25180 | 9/1995 |
| WO | WO9525180 A1 * | 9/1995 |
| WO | WO 9525180 A1 * | 9/1995 |
| WO | WO 96/14406 | 5/1996 |
| WO | PCT/US96/18812 | 11/1996 |
| WO | WO 97/16566 | 5/1997 |
| WO | WO 97/17076 | 5/1997 |
| WO | WO 97/17471 | 5/1997 |
| WO | WO 97/19193 | 5/1997 |
| WO | WO 98/04746 | 2/1998 |
| WO | WO 98/07833 | 2/1998 |
| WO | WO 98/14610 | 4/1998 |
| WO | PCT/US98/21177 | 10/1998 |
| WO | WO 99/18241 | 4/1999 |
| WO | WO 99/31276 | 6/1999 |
| WO | PCT/US99/16373 | 7/1999 |
| WO | WO 99/46392 | 9/1999 |
| WO | PCT/AU99/01110 | 12/1999 |
| WO | WO 00/15849 | 3/2000 |
| WO | PCT/US00/16130 | 6/2000 |
| WO | PCT/US00/32370 | 11/2000 |
| WO | WO 00/71562 | 11/2000 |
| WO | PCT/US01/11151 | 4/2001 |
| WO | PCT/US01/11947 | 4/2001 |
| WO | PCT/US01/20217 | 6/2001 |

| WO | US01/19657 | 6/2001 |
| WO | PCT/US01/20933 | 7/2001 |
| WO | PCT/US02/00005 | 1/2002 |
| WO | PCT/US02/02601 | 1/2002 |
| WO | PCT/US02/15045 | 5/2002 |
| WO | PCT/US02/19443 | 6/2002 |
| WO | PCT/US02/27097 | 8/2002 |
| WO | PCT/US02/33244 | 10/2002 |
| WO | PCT/US03/00678 | 1/2003 |
| WO | WO 03/033724 | 3/2003 |
| WO | PCT/US03/39430 | 12/2003 |

OTHER PUBLICATIONS

Maniatis et al. "Molecular cloning: a laboratory Manual" Cold Spring Harbor Laboratory Press, Cold Spring Harbor, NY. 1982. pp. 89-91.*
Nycz et al. ("Quantitative reverse transcription strand displacement amplification: quantitation of nucleic acids using an isothermal amplification technique" Anal Biochem. Jun. 1, 1998;259(2):226-34.*
Maniatis et al. ("Molecular cloning: a laboratory Manual" Cold Spring Harbor Laboratory Press, Cold Spring Harbor, NY. 1982. pp. 89-91).*
Ibkobashvili et al. (Nucleic Acid Research, 1999, vol. 27, No. 6).*
Aliotta et al. Thermostable Bst DNA Polymerase I lacks a 3'→ 5' proofreading exonuclease activity. Genet. Anal. (Netherlands) 12:185-195 (1996).
Arnold et al. Assay Formats Involving Acridinium-Ester-Labeled DNA Probes. Clin. Chem. 35(8):1588-1594 (1989).
Asseline et al. Solid-Phase Preparation of 5', 3'-Heterobifunctional Oligonucleotides Using Modified Solid Supports. Tetrahedron. 48(7):1233-1254 (1992).
Baner et al. Signal amplification of padlock probes by rolling circle replication. Nucl. Acids Res. 26(22):5073-5078 (1998).
Beaucage et al. Deoxynucleoside phosphoramidites—a new class of key intermediates for deoxypolynucleotide synthesis. Tetrahedron Lett. 22(20):1859-1862 (1981).
Beigelman et al. Synthesis of 1-Deoxy-D-Ribofuranose phosphoramidite and the incorporation of abasic nucleotides in stem-loop II of a hammerhead ribozyme. Bioorganic & Medicinal Chemistry Letters 4(14):1715-1720 (1994).
Biragyn et al. Mediators of Innate Immunity That Target Immature, But Not Mature, Dendritic Cells Induce Antitumor Immunity When Genetically Fused with Nonimmunogenic Tumor Antigens. J. Immunol. 167:6644-6653 (2001).
Birkenmeyer et al. DNA probe amplification methods. J. Virol. Meth. 35:117-126 (1991).
Blanco et al. Highly efficient DNA synthesis by the phage ø29 DNA polymerase. J. Biol. Chem. 264(15):8935-8940 (May 25, 1989).
Bloch et al. α-anomeric DNA: β-RNA hybrids as new synthetic inhibitors of Escherichia coli RNase H, Drosophila embryo RNase H and M-MLV reverse transcriptase. Gene. 72:349-360 (1988).
Boehmer and Lehman. Herpes simplex virus type 1 ICP8: helix-destabilizing properties. J. Virol. 67(2):711-715 (Feb. 1993).
Brownie et al. The elimination of primer-dimer accumulation in PCR. Nucl. Acids Res. 25(16):3235-3241 (1997).
Brownstein et al. Modulation of non-templated nucleotide addition by Taq DNA polymerase: primer modifications that facilitate genotyping. Biotechniques 20(6):1004-1010 (1996).
Buchanan et al. Long DOP-PCR of rare archival anthropological samples. Hum. Biol. 72(6):911-925 (2000).
Chatterjee et al. Cloning and overexpression of the gene encoding bacteriophage T5 DNA polymerase. Gene 97:13-19 (1991).
Cheung and Nelson. Whole genome amplification using a degenerate oligonucleotide primer allows hundreds of genotypes to be performed on less than one nanogram of genomic DNA. Proc Natl Acad Sci USA 93:14676-14679 (Dec. 1996).
Cocuzza. A phosphoramidite reagent for automated solid phase synthesis of 5'-biotinylated oligonucleotides. Tetrahedron Lett. 30(46):6287-6290 (1989).
Compton. Nucleic acid sequence-based amplification. Nature 350(6313):91-92 (Mar. 7, 1991).
Connolly et al. Chemical synthesis of oligonucleotides containing a free sulphydryl group and subsequent attachment of thiol specific probes. Nucl. Acids Res. 13(12):4485-4502 (1985).
Connolly. The synthesis of oligonucleotides containing a primary amino group at the 5'-terminus. Nucl. Acids Res. 15(7):3131-3139 (1987).
Craxton et al. Linear amplification sequencing, a powerful method for sequencing DNA. Methods: A Companion in Methods in Enzymology. 3(1):20-26 (1991).
Dolinnaya et al. Oligonucleotide circularization by template-directed chemical ligation. Nucl. Acids Res. 21(23):5403-5407 (1993).
Dreyer and Dervan. Sequence-specific cleavage of single-stranded DNA: oligodeoxynucleotide-EDTA Fe(II). Proc. Natl. Acad. Sci. USA 82:968-972 (Feb. 1985).
Durand et al. Circular dichroism studies of an oligodeoxyribonucleotide containing a hairpin loop made of a hexaethylene glycol chain: conformation and stability. Nucl. Acids Res. 18(21):6353-6359 (1990).
Eckert et al. DNA polymerase fidelity and the polymerase chain reaction. PCR Meth. Appl. 1:17-24 (1991).
Egholm et al. Peptide Nucleic Acids (PNA). Oligonucleotide Analogues with an Achiral Peptide Backbone. J. Am. Chem. Soc. 114:1895-1897 (1992).
Englisch et al. Chemically Modified Oligonucleotides as Probes and Inhibitors. Angewandte Chemie, International Edition in English 30(6):613-629 (Jun. 1991).
Esteban et al. Fidelity of ø29 DNA polymerase. comparison between protein-primed iInitiation and DNA polymerization, J. Biol. Chem. 268(4):2719-2726 (Feb. 5, 1993).
Faruqi et al. High-throughput genotyping of single nucleotide polymorphisms with rolling circle amplification, BMC Genomics 2:4 (2001).
Ferrie et al. Development, multiplexing, and application of ARMS tests for common mutations in the CFTR gene. Am. J. Hum. Genet. 51:251-262 (1992).
Gait. Oligoribonucleotides. Antisense Research and Applications. Crooke et al., eds. . CRC Press. Boca Raton. Chapter 16 pp. 289-301(1993).
Gillespie et al. HLA class II typing of whole genome amplified mouth swab DNA, Tissue Antigens 56:530-538 (2000).
Grzybowski et al. Synthesis and antibody-mediated detection of oligonucleotides containing multiple 2,4-dinitrophenyl reporter groups. Nucl. Acids Res. 21(8):1705-1712 (1993).
Guillier-Gencik et al. Generation of whole-chromosome painting probes specific to each chicken macrochromosome, Cytogenet. Cell Genet. 87:282-285 (1999).
Guo et al. Direct fluorescence snalysis of genetic polymorphisms by hybridization with oligonucleotide arrays on glass supports, Nucl. Acids Res. 22(24):5456-5465 (1994).
Gupta et al. A universal solid support for the synthesis of 3'-thiol group containing oligonucleotides. Tetrahedron Lett. 31(17):2471-2474 (1990).
Gusev et al. Rolling circle amplification: a new approach to increase sensitivity for immunohistochemistry and flow cytometry. American Journal of Pathology 159(1):63-69 (2001).
Hall et al. Mixed Anhydrides as Intermediates in the Synthesis of Dinucleoside Phosphates. J. Chem. Soc. 3291-3296 (1957).
Harper and Wells. Recent advances and future developments in PGD, Prenat. Diagn. 19:1193-1199 (1999).
Henegariu et al. Custom fluorescent-nucleotide synthesis as an alternative method for nucleic acid labeling. Nat. Biotechnol. 18:345-348 (Mar. 2000).
Holton et al. A simple and efficient method for direct cloning of PCR products using ddT-tailed vectors. Nucl. Acids Res. 19(5):1156 (1991).
Hoy et al. Bromodeoxyuridine/DNA analysis of replication in CHO cells after exposure to UV light. Mutat. Res. 290:217-230 (1993).
Huryn and Okabe. AIDS-driven nucleoside chemistry. Chem. Rev. 92:1745-1768 (1992).
Itakura et al. Synthesis and use of synthetic oligonucleotides. Ann. Rev. Biochem. 53:323-356 (1984).

Iyer et al. 3*H*-1, 2-benzodithiole-3-one 1, 1-dioxide as an improved sulfurizing reagent in the solid-phase synthesis of oligodeoxyribonucleoside phosphorothioates. *J. Am. Chem. Soc.* 112:1253-1254 (1990).

Jablonski et al. Preparation of oligodeoxynucleotide-alkaline phosphatase conjugates and their use as hybridization probes. *Nucl. Acids Res.* 14(15):6115-6128 (1986).

Jacobsen et al. The N-Terminal amino-acid sequences of DNA polymerase I from *Escherichia coli* and of the large and the small fragments obtained by a limited proteolysis. *Eur. J. Biochem.* 45:623-627 (1974).

Jones et al. Studies on the alkylation of 2', 3'-*o*-isopropylideneuridine. *J. Carbohydrates, Nucleosides, Nucleotides* 4(5):301-306 (1977).

Jun-Dong et al. Application of Wittig reaction to adenosine derivatives. *Synthesis* 909-911 (Oct. 1990).

Jung et al. Bacteriophage PRD1 DNA polymerases: evolution of DNA polymerases. *Proc. Natl. Acad. Sci. USA* 84:8287-8291 (Dec. 1987).

Kaboord and Benkovicl. Accessory proteins function as matchmakers in the assembly of the T4 DNA polymerase holoenzyme. *Curr. Biol.* 5(2):149-157 (1995).

Kalnik et al. NMR Studies of Abasic Sites in DNA Duplexes: Deoxyadenosine Stacks into the Helix Opposite the Cyclic Analogue of 2-Deoxyribose. *Biochemistry* 27:924-931 (1998).

Kerkhof. A Comparison of Substrates for Quantifying the Signal from a Nonradiolabeied DNA Probe. *Anal. Biochem.* 205:359-364 (1992).

Khrapko et al. Hybridization of DNA with oligonucleotides iimobilized in gel: a convenient method for detecting single base substitutions. *Mol Biol (Mosk) (USSR)* 581-591 (1991).

Kim et al. Whole genome amplification and molecular genetic analysis of DNA from paraffin-embedded prostate adenocarcinoma tumor tissue. *J. Urol.* 162:1512-1518 (Oct. 1999).

Klein et al. Comparative genomic hybridization, loss of heterozygosity, and DNA sequence analysis of single cells, *Proc Natl Acad Sci USA* 96:4494-4499 (Apr. 1999).

Kong et al. Characterization of a DNA polymerase from the hyperthermophile archaea *Thermococcus litoralis*. *J. Biol. Chem.* 268(3):1965-1975 (Jan. 25, 1993).

Kumar et al. A simple method for introducing a thiol group at the 5'-end of synthetic oligonucleotides. *Nucl. Acids Res.* 19(16):4561 (1991).

Kuukasjarvi et al. Optimizing DOP-PCR for universal amplification of small DNA samples in comparative genomic hybridization. *Genes, Chromosomes and Cancer* 18:94-101 (1997).

Landegren et al. A ligase-mediated gene detection technique. *Science* 241:1077-1080 (1988).

Landegren. Molecular mechanics of nucleic acid sequence amplification. *Trends Genetics* 9(6):199-202 (1993).

Langer et al. Enzymatic synthesis of biotin-labeled polynucleotides: Novel nucleic acid affinity probes. *Proc. Natl. Acad. Sci. USA* 78(11):6633-6637 (1981).

Lantz et al. Biotechnical use of polymerase chain reaction for microbiological analysis of biological samples. *Biotechnol. Ann. Rev.* 5:87-130 (2000).

Lesnick and Freier. Relative Thermodynamic Stability of DNA, RNA, and DNA: RNA Hybrid Duplexes: Relationship with Base Composition and Structure. *Biochemistry* 34:10807-10815 (1995).

Letsinger and Lunsford. Synthesis of thymidine oligonucleotides by phosphite triester intermediates. *J. Am. Chem. Soc.* 9:3655-3661 (1976).

Li et al. Enzyme-linked synthetic oligonucleotide probes: non-radioactive detection of enterotoxigenic *Escherichia coli* in faecal specimens. *Nucl. Acids Res.* 15(13):5275-5287 (1987).

Lizardi et al. Mutation detection and single-molecule counting using isothermal rolling-circle amplification. *Nat. Genet.* 19:225-232 (Jul. 1998).

Lockhart et al. Expression monitoring by hybridization to high-density oligonucleotide arrays. *Nature Biotechnology* 14:1675-1680 (Dec. 1996).

MacKellar et al. Synthesis and physical properties of anti-HIV antisense oligonucleotides bearing terminal lipophilic groups. *Nucl. Acids Res.* 20(13):3411-3417 (1992).

Matray and Kool. A specific partner for abasic damage in DNA. *Nature* 399:704-708 (1999).

Matsumoto et al. Primary structure of bacteriophage M2 DNA polymerase: conserved segments within protein-priming DNA polymerases and DNA polymerase I of *Escherichia coli*. *Gene* 84:247-255(1989).

Matteucci and Caruthers. Synthesis of deoxyoligonucleotides on a polymer support. *J. Am. Chem. Soc.* 103:3185-3191 (1981).

McGraw et al. Sequence-Dependent Oligonucleotide-Target Duplex Stabilities: Rules from Empirical Studies with a Set of Twenty-Mers. *Biotechniques* 8(6):674-678 (1990).

Moran et al. Non-hydrogen bonding 'terminator' nucleosides increase the 3'-end homogeneity of enzymatic RNA and DNA synthesis. *Nucl. Acids Res.* 24(11):2044-2052 (1996).

Mullenix et al. Allergen-specific IgE Detection on Microarrays Using Rolling Circle Amplification: Correlation with in Vitro Assays for Serum IgE. *Clin. Chem.* 47(10):1926-1929 (2001).

Narang et al. Chemical Synthesis of Deoxyoligonucleotides by the Modified Triester Method. *Meth. Enzymol.* 65:610-620 (1980).

Nelson et al. Oligonucleotide labeling methods 3. Direct labeling of oligonucleotides employing a novel, on-nucleosidic,2-aminobutyl-1,3-propanediol backbone. *Nucl. Acids Res.* 20(23):6253-6259 (1992).

Nelson. Rapid Detection of Genetic Mutations Using the Chemiluminescent Bydridization Protection Assay (HPA): Overview and Comparison with Other Methods. *Crit. Rev. Clin. Lab. Sci.* 35(5):369-414 (1998).

Nielsen et al. Peptide Nucleic Acid (PNA). A DNA Mimic with a Peptide Backbone. *Bioconjug. Chem.* 5:3-7 (1994).

Nielsen et al. Sequence-Selective Recognition of DNA by Strand Displacement with a Thymine-Substiuted Polyamide. *Science* 254:1497-1500 (Dec. 1991).

Nuovo et al. In Situ Amplification Using Universal Energy Transfer-labeled Primers, The Journalof Histochemistry & Cytochemistry, The Histochemical Society, Inc., New York, New York 43(3):273-279 (1999), XP008002684.

Parker et al. Targeted gene walking polymerase chain reaction. *Nucl. Acids Res.* 19(11):3055-3060 (1991).

Paulson et al. Loss of Heterozygosity Analysis Using Whole Genome Amplification, Cell Sorting, and Fluorescence-Based PCR. *Genome Res.* 9:482-491 (1999).

Paunio et al. Preimplantation diagnosis by whole-genome amplification, PCR amplification, and solid-phase minisequencing of blastomere DNA. *Clin. Chem.* 42(9):1382-1390 (1996).

Pease et al. Light-generated oligonucleotide arrays for rapid DNA sequence analysis. *Proc. Natl. Acad. Sci. USA*, 91:5022-5026 (May 1994).

Pieles et al. Preparation of a novel psoralen containing deoxyadenosine building block for the facile solid phase synthesis of psoralen-modified oligonucleotides for a sequence specific crosslink to a given targe sequence. *Nucl. Acids Res.* 17(22):8967-8978 (1989).

Pieles et al. Psoralen covalently linked to oligodeoxyribonucleotides: synthesis, sequence specific recognition of DNA and photo-cross-linking to pyrimidine residues of DNA. *Nucl. Acids Res.* 17(1):285-299 (1989).

Pless et al. Solid support synthesis of oligothymidylates using phosphorochloridates and 1-alkylimidazoles. *Nucl. Acids Res.* 2(6):773-786 (Jun. 1975).

Pruckler et al. Comparison of *Legionella pneumophila* Isolates by Arbitrarily Primed PCR and Pulsed-Field Gel Electrophoresis: Analysis from Seven Epidemic Investigations. *J. Clin. Microbiol.* 33(11):2872-2875 (Nov. 1995).

Ray and Jaxa-Chamiec. Novel thymidine analogues via reaction of unprotected 5'-Deoxy-5'-iodothymidine with dianions. *Heterocycles* 31(10):1777-1780 (1990).

Rigler and Romano. Differences in the Mechanism of Stimulation of T7 DNA Polymerase by Two Binding Modes of *Escherichia Coli* Single-stranded DNA-binding Protein. *J. Biol. Chem* 270(15):8910-8919 (1995).

Robins and Wouk. Fluorination at C5' of nucleosides, synthesis of the new class of 5'-Fluoro-5'-S-Aryl (Alkyl) thionucleosides from adenosine. *Tetrahedron Lett.* 29(45):5729-5732 (1988).

Rychlik et al. Optimization of the annealing temperature for DNA amplification in vitro. *Nucl. Acids Res.* 18(21):6409-6412 (1990).

Saiki et al. Primer-Directed Enzymatic Amplification of DNA with a Thermostable DNA Polymerase. *Science* 239:487-491 (1988).

Salunkhe et al. Control of Folding and Binding of Oligonucleotides by Use of a Nonnucleotide Linker. *J. Amer. Chem. Soc.* 114:8768-8772 (1992).

Sambrook et al. *Molecular Cloning: A Laboratory Manual*, 2$^{nd}$ Edition (Cold Spring Harbor Laboratory Press, Cold Spring Harbor, NY) Chapters 5, 6 (1989).

Sanghvi. Chapter 15, Heterocyclic base modifications in nucleic acids and their applications in antisense oligonucleotides. *Antisense Res. and Appl.* p. 273-301 (1993).

Sano et al. Detection of heavy methylation in human repetitive DNA subsets by a monoclonal antibody against 5-methylcytosine. *Biochim. Biophys. Acta* 951:157-165 (1988).

Schena et al. Quantitative Monitoring of Gene Expression Patterns with a Complementary DNA Microarray. *Science* 270:467-470 (1995).

Schweitzer et al. Immunoassays with rolling circle DNA amplification: A versatile platform for ultrasensitive antigen detection. *Proc. Natl. Acad. Sci. USA* 97(18):10113-10119 (Aug. 29, 2000).

Schweitzer et al. Multiplexed protein profiling on microarrays by rolling-circle amplification. *Nat. Biotechnol.* 20:359-365 (Apr. 2002).

Sequin. Nucleosides and Nucleotides. Part 7. Four Dithymidine Monophosphates with Different Anomeric Configurations, Their Synthesis and Behaviour Towards Phosphodiesterases. *Helv. Chim. Acta.* 57(1):68-81 (1974).

Siegal et al. A Novel DNA Helicase from Calf Thymus. *J. Biol. Chem.* 267(19):13629-13635 (Jul. 5, 1992).

Sinha and Cook. The preparation and application of functionalized synthetic oligonucleotides: III. Use of H-phosphonate derivatives of protected amino-hexanol and mercapto-propanol or-hexanol. *Nucl. Acids Res.* 16(6):2659-2669 (1988).

Skaliter et al. Rolling circle DNA replication in vitro by a complex of herpes simplex virus Type 1-encoded enzymes. *Proc. Natl. Acad. Sci. USA* 91(22):10665-10669 (Oct. 1994).

Southern. Detection of Specific Sequences Among DNA Fragments Separated by Gel Electrophoresis. *J. Mol. Biol.* 98:503-517 (1975).

Sproat et al. The synthesis of protected 5'-mercapto-2',5'-dideoxyribonucleoside-3'-O-phosphoramidites; uses of 5'-mercapto-oligodeoxyribonucleotides. *Nucl. Acids Res.* 15(12):4837-4848 (1987).

Stein et al. Mode of Action of 5'-Linked Cholesteryl Phosphorothioate Oligodeoxynucleotides in Inhibiting Syncytia Formation and Infection by HIV-1 and HIV-2 in Vitro. *Biochemistry* 30:2439-2444 (1991).

Stimpson et al. Real-time detection of DNA hybridization and melting on oligonucleotide arrays by using optical wave guides. *Proc Natl. Acad. Sci. USA*, 92:6379-6383 (Jul. 1995).

Stump et al. The use of modified primers to eliminate cycle sequencing artifacts. *Nucl. Acids Res.* 27(23):4642-4648 (1999).

Takasugi et al. Sequence-specific photo-induced cross-linking of the two strands of double-helical DNA by a psoralen covalently linked to a triple helix-forming oligonucleotide. *Proc. Natl. Acad. Sci. USA* 88:5602-5606 (Jul. 1991).

Takeshita et al. Oligodeoxynucleotides containing synthetic abasic sites. Model substrates for DNA polymerases and apurinic/apyrimidinic endonucleases. *J. Biol. Chem.* 262(21):10171-10179 (Jul. 1987).

Tanaka et al. Cleavage of a nucleosidic oxetane with carbanions: synthesis of a highly promising candidate for anti-HIV agents: a phosphokate isosters O AZT 5'-phosphate. *Tetrahedron Lett.* 30(19):2567-2570 (1989).

Tani et al. Defensins act as potent adjuvants that promote cellular and humoral immune responses in mice to a lymphoma idiotype and carrier antigens. *International Immunology* 12(5):691-700 (2000).

Telenius et al. Degenerate Oligonucleotide-Primed PCR: General Amplification of Target DNA by a Single Degenerate Primer. *Genomics* 13:718-725 (1992).

Tenover et al. Comparison of Traditional and Molecular Methods of Typing Isolates of *Staphylococcus aureus*. *J. Clin. Microbiol.* 32(2):407-415 (Feb. 1994).

Thomas et al. Amplification of Padlock Probes for DNA Diagnostics by Cascade Rolling Circle Amplification or the Polymerase Chain Reaction. *Arch. Pathol. Lab. Med.* 123(12):1170-1176 (Dec. 1999).

Thoung et al. Solid phase synthesis of oligo-α and oligo-β-deoxynucleotides. *Tetrahedron Lett.* 29(46):5905-5908 (1988).

Tsurumi et al. Functional Interaction Between Epstein-Barr Virus DNA Polymerase Catalytic Subunit and Its Accessory Subunit In Vitro. *J. Virol.* 67(12):7648-7653 (Dec. 1993).

Tyagi and Kramer. Molecular Beacons: Probes that Fluoresce upon Hybridization. *Nat. Biotech.* 14:303-308 (Mar. 1996).

Villemain and Giedroc. The N-Terminal B-Domain of T4 Gene 32 Protein Modulates the Lifetime of Cooperatively Bound Gp32-ss Nucleic Acid Complexes. *Biochemistry* 35:14395-14404 (1996).

Walker and Linn. Detection of *Mycobacterium tuberculosis* DNA with thermophilic strand displacement amplification and fluorescence polarization. *Clin. Chem.* 42(10):1604-1608 (1996).

Walker et al. Isothermal in vitro amplification of DNA by a restriction enzyme/DNA polymerase system. *Proc. Natl. Acad. Sci. USA.* 89:392-396 (Jan. 1992).

Walker et al. Strand displacement amplification—an isothermal, in vitro DNA amplification technique. *Nucl. Acids Res.* 20(7):1691-1696 (1992).

Wansink et al. Flourescent Labeling of Nascent RNA Reveals Transcription by RNA Polymerase II in Domains Scattered Throughout the Nucleus. *J. Cell Biol.* 122(2):283-293 (1993).

Wells et al. Comprehensive chromosomal analysis of human preimplantation embryos using whole genome amplification and single cell comparative genomic hybridization. *Mol. Hurn. Reprod.* 6(11):1055-1062 (2000).

Wells et al. Detailed chromosomal and molecular genetic analysis of single cells by whole genome amplification and comparative genomic hybridization. *Nucl. Acids Res.* 27(4):1214-1218 (1999).

Will et al. The synthesis of oligonucleotides that contain 2,4-dinitrophenyl reporter groups. *Carbohydr. Res.* 216:315-322 (1991).

Yu et al. Cyanine dye dUTP analogs for enzymatic labeling of DNA probes. *Nucl. Acids Res.* 22(15):3226-3232 (1994).

Zhang et al. Amplification of target-specific, ligation-dependent circular probe. *Gene* 211:277-285 (1998).

Zhang et al. Whole genome amplification from a single cell: implications for genetic analysis. *Proc. Natl. Acad. Sci. USA* 89:5847-5851 (Jul. 1992).

Zhu and Ito. Purification and characterization of PRD1 DNA polymerase. *Biochim. Biophys. Acta* 1219:267-276 (1994).

Zijderveld et al. Helix-Destabilizing Properties of the Adenovirus DNA-Binding Protein. *J. Virol.* 68(2):1158-1164 (Feb. 1994).

Zuckerman et al. Efficient methods for attachment of thiol specific probes to the 3'-ends of synthetic oligodeoxyribonucleotides. *Nucl. Acids Res.* 15(13):5305-5321 (1987).

Iakobashvili R, Lapidot A. (1999) Low temperature cycled PCR protocol for Klenow fragment of DNA polymerase I in the presence of proline. Nucleic Acids Res. 27(6): 1566-1568.

Kuchel PW, Ralston GB (Eds.) Schaum's Outline—Biochemistry (2$^{nd}$ Ed.), McGraw-Hill: USA (1998).

Ling MM, Robinson BH. (1997) Approaches to DNA mutagenesis: an overview. Anal Biochem. 254(2): 157-178.

Pan X, Urban AE, Palejev D, Schulz V, Grubert F, Hu Y, Snyder M, Weissman SM. (2008) A procedure for highly specific, sensitive, and unbiased whole-genome amplification. Proc Natl Acad Sci USA. 105(40): 15499-15504.

U.S. Appl. 11/887,678, filed Mar. 27, 2006, Korfhage, C.
U.S. Appl. 11/991,434, filed May 4, 2007, Korfhage, C.
U.S. Appl. No. 09/803,713, filed Mar. 9, 2001, Alsmadi, O.A.
U.S. Appl. No. 10/325,490, filed Dec. 19, 2002, Alsmadi, O.A.
U.S. Appl. No. 10/404,944, filed Mar. 31, 2003, Alsmadi, O.A.
U.S. Appl. No. 09/547,757, filed Apr. 12, 2000, Faruqi, A.F.
U.S. Appl. No. 09/597,836, filed Jun. 20, 2000, Kingsmore, S.
U.S. Appl. No. 10/341,287, filed Jan. 13, 2003, Kingsmore, S.

U.S. Appl. No. 11/187,537, filed Jul. 22, 2005, Kingsmore, S.
U.S. Appl. No. 09/897,259, filed Jul. 2, 2001, Ward, D.C.
U.S. Appl. No. 09/910,383, filed Jul. 20, 2001, Nallur, G.
U.S. Appl. No. 09/977,868, filed Oct. 15, 2001, Bornarth, C.
U.S. Appl. No. 09/982,212, filed Oct. 18, 2001, Bornarth, C.
U.S. Appl. No. 10/272,465, filed Oct. 15, 2002, Bornarth, C.
U.S. Appl. No. 10/429,229, filed May 2, 2003, Bornarth, C.
U.S. Appl. No. 11/871,707, filed Oct. 12, 2007, Bornarth, C.
U.S. Appl. No. 08/754,681, filed Nov. 21, 1996, Lizardi, P.
U.S. Appl. No. 09/602,428, filed Jun. 23, 2000, Lizardi, P.
U.S. Appl. No. 09/841,513, filed Apr. 24, 2001, Lizardi, P.
U.S. Appl. No. 10/413,041, filed Apr. 10, 2003, Lizardi, P.
U.S. Appl. No. 10/072,666, filed Feb. 8, 2002, Kumar, G.
U.S. Appl. No. 09/460,078, filed Dec. 14, 1999, Hafner, G.
U.S. Appl. No. 10/917,580, filed Aug. 13, 2004, Hafner, G.
U.S. Appl. No. 10/325,665, filed Dec. 19, 2002, Alsmadi, O.
U.S. Appl. No. 10/335,573, filed Dec. 31, 2002, Kumar, G.
U.S. Appl. No. 11/201,339, filed Aug. 10, 2005, Kumar, G.
U.S. Appl. No. 10/327,602, filed Dec. 20, 2002, Lasken, R.
U.S. Appl. No. 10/405,822, filed Mar. 31, 2003, Abarzua, P.
U.S. Appl. No. 10/454,946, filed Jun. 4, 2003, Feaver, W.J.
U.S. Appl. No. 09/605,192, filed Jun. 28, 2000, Lasken, R.
U.S. Appl. No. 09/920,571, filed Jul. 31, 2001, Lasken, R.
U.S. Appl. No. 09/577,444, filed May 24, 2000, Kingsmore, S.
U.S. Appl. No. 09/897,665, filed Jul. 2, 2001, Kingsmore, S.
U.S. Appl. No. 09/910,372, filed Jul. 20, 2001, Bandaru, R.
U.S. Appl. No. 10/465,759, filed Jun. 19, 2003, Bandaru, R.
U.S. Appl. No. 09/723,685, filed Nov. 28, 2000, Abarzua, P.
U.S. Appl. No. 10/196,539, filed Jul. 16, 2002, Abarzua, P.
U.S. Appl. No. 11/429,549, filed May 5, 2006, Abarzua, P.
U.S. Appl. No. 09/827,289, filed Apr. 5, 2001, Abarzua, P.
U.S. Appl. No. 10/177,629, filed Jun. 19, 2002, Wiltshire, S.
U.S. Appl. No. 09/931,736, filed Aug. 17, 2001, Shao, W.
U.S. Appl. No. 10/931,015, filed Aug. 31, 2004, Shao, W.
U.S. Appl. No. 11/870,715, filed Oct. 11, 2007, Korfhage, C.
U.S. Appl. No. 11/744,553, filed May 4, 2007, Korfhage, C.
U.S. Appl. No. 11/887,678, Korthage, C.
U.S. Appl. No. 11/991,435, Korfhage, C.
U.S. Appl. No. 08/563,912, filed Nov. 21, 1995, Lizardi, P.
U.S. Appl. No. 09/132,553, filed Aug. 11, 1998, Lizardi, P.
U.S. Appl. No. 09/644,723, filed Aug. 23, 2000, Lizardi, P.
U.S. Appl. No. 09/132,552, filed Aug. 11, 1998, Lizardi, P.
U.S. Appl. No. 10/038,718, filed Jan. 2, 2002, Lizardi, P.
U.S. Appl. No. 10/896,513, filed Jul. 22, 2004, Lizardi, P.
U.S. Appl. No. 08/946,732, filed Oct. 8, 1997, Lizardi, P.
U.S. Appl. No. 09/397,915, filed Sep. 17, 1999, Lizardi, P.
U.S. Appl. No. 09/911,226, filed Jul. 23, 2001, Lizardi, P.
U.S. Appl. No. 10/700,018, filed Nov. 3, 2003, Lizardi, P.
U.S. Appl. No. 09/357,487, filed Jul. 20, 1999, Lizardi, P.
"Polymerase from NEB," printed information from New England BioLabs, http://www.neb.com/nebecommitech_reference/polymerases/polymerase_from_neb.asp (3 total pages, retrieved on Jul. 26, 2007).
Alsmadi O, Alkayal F, Monies D, Meyer BF. (2009) Specific and complete human genome amplification with improved yield achieved by phi29 DNA polymerase and a novel primer at elevated temperature. BMC Res Notes. 2:48.
Andras SC, Power JB, Cocking. EC, Davey MR. (2001) Strategies for signal amplification in nucleic acid detection. Mol Biotechnol. 19(1):29-44.
Chandler DP. (1998) Redefining relativity: quantitative PCR at low template concentrations for industrial and environmental microbiology. J. Indust. Microbiol. Biotech. 21:128-140.
Dean FB, Hosono S, Fang L, Wu X, Faruqi AF, Bray-Ward P, Sun Z, Zong Q, Du Y, Du J, Driscoll M, Song W, Kingsmore SF, Egholm M, Lasken RS. (2002) Comprehensive human genome amplification using multiple displacement amplification. Proc Natl Acad Sci USA 99(8):5261-66.
Detter JC, Jett JM, Lucas SM, Dalin E, Arellano AR, Wang M, Nelson JR, Chapman J, Lou Y, Rokhsar D, Hawkins TI, Richardson PM. (2002) Isothermal amplification applications for high-throughput genomics. Genomics. 80(6):691-98.

Biomagnetic techniques in molecular biology. 1. Solid-Phase DNA Sequencing. Dynal A.S. (2nd Edition, 1995).
Galli DM, Leblanc DJ. (1995) Transcriptional analysis of rolling circle replicating plasmid pVT736-1: evidence for replication control by antisense RNA. J Bacteriol. 177(15):4474-80.
Jiang SW, Trujillo MA, Eberhardt NL. (1996) An efficient method for generation and subcloning of tandemly repeated DNA sequences with defined length, orientation and spacing. Nucleic Acids Res. 24(16):3278-79.
Laval M, Azou Y, Miassod R. (1989) Structural organization and expression of amplified chromosomal sequences, which include the rudimentary gene, in cultured Drosophila cells resistant to N-(phosphonacetyl)-L-aspartate. Mol Gen Genet. 220(1):102-12.
Lizardi PM, Huang X, Zhu Z, Bray-Ward P, Thomas DC, Ward DC. (1998) Mutation detection and single-molecule counting using isothermal rolling-circle amplification. Nat Genet. 19(3):225-32.
Nilsson M, Malmgren H, Samiotaki M, Kwiatkowski M, Chowdhary BP, Landegren U. (1994) Padlock probes: circularizing oligonucleotides for localized DNA detection. Science. 265(5181):2085-88.
Rudbeck L, Dissing J. (1998) Rapid, simple alkaline extraction of human genomic DNA from whole blood, buccal epithelial cells, semen and forensic stains for PCR. Biotechniques. 25(4):588-90, 592.
Schweitzer B, Kingsmore S. (2001) Combining nucleic acid amplification and detection. Curr Opin Biotechnol. 12(1):21-27.
Shumaker JM, Metspalu A, Caskey CT. (1996) Mutation detection by solid phase primer extension. Hum Mutat. 7(4):346-54.
Stratagene Catalog, Gene Characterization Kit, p. 39, Year 1988.
Voisey J, Hafner Gj, Morris CP, van Daal A, Giffard PM. (2001) Interrogation of multimeric DNA amplification products by competitive primer extension using bst DNA polymerase (large fragment). Biotechniques. 31(5):1122-4, 1126, 1128-29.
Walker GT, Nadeau JG, Spears PA, Schram JL, Nycz CM, Shank DD. (1994) Multiplex strand displacement amplification (SDA) and detection of DNA sequences from Mycobacterium tuberculosis and other mycobacteria. Nucleic Acids Res. 22(13):2670-77.
Warnecke PM, Stirzaker C, Melki JR, Millar DS, Paul CL, Clark SJ. (1997) Detection and measurement of PCR bias in quantitative methylation analysis of bisulphite-treated DNA. Nucleic Acids Res. 25(21):4422-26.
Communication pursuant to Article 114(2) EPC issued Oct. 23, 2009 for European Patent Application No. 2801776.2 filed on Oct. 15, 2002 (Applicant: Molecular Staging, Inc.).
Written Opinion issued Feb. 24, 2004 for PCT/US2002/033244 filed on Oct. 15, 2002, which published as WO 2003/033724 on Apr. 24, 2003 (Applicant: Molecular Staging, Inc.).
Petition for Withdrawal of Holding of Abandonment filed Feb. 13, 2004 for U.S. Appl. No. 09/977,886 filed on Oct. 15, 2001 (Inventors: Dean et al).
Notice of Abandonment issued May 25, 2010 for U.S. Appl. No. 11/871,707 filed on Oct. 12, 2007 (Inventors : Bornarth et al.).
Final Rejection issued Oct. 29, 2009 for U.S. Appl. No. 11/871,707 filed on Oct. 12, 2007 (Inventors : Bornarth et al.).
Response after Non-Final Rejection filed Jun. 22, 2009 for U.S. Appl. No. 11/871,707 filed on Oct. 12, 2007 (Inventors : Bornarth et al.).
Non-Final Rejection issued Jan. 28, 2009 for U.S. Appl. No. 11/871,707 filed on Oct. 12, 2007 (Inventors: Bornarth et al.).
Communication regarding Expiry of Opposition Time Period issued Jan. 15, 2002 for European Patent Application No. 0862652 filed on Nov. 21, 1996 (Applicant: Yale University).
Restriction Requirement issued Jun. 17, 1997 for U.S. Appl. No. 08/754,681 filed on Nov. 21, 1996 (Inventors: Lizardi et al.).
Decision on Petition issued Jul. 3, 2003 for U.S. Appl. No. 10/413,041 filed on Apr. 10, 2003 (Inventors: Lizardi et al.).
Petition to Correct Filing Date filed May 8, 2003 for U.S. Appl. No. 10/413,041 filed on Apr. 10, 2003 (Inventors: Lizardi et al.).
Preliminary Amendment filed Apr. 10, 2003 for U.S. Appl. No. 10/413,041 filed on Apr. 10, 2003 (Inventors: Lizardi et al.).
Examination Report issued Jan. 8, 2008 for Japanese Patent Application No. 2000588388 filed Dec. 14, 1999 (Applicant: Molecular Staging, Inc.).

International Preliminary Examination Report issued Oct. 4, 2000 for PCT/AU1999/001110 filed on Dec. 14, 1999, which published as WO 2000/036141 on Jun. 22, 2000 (Applicant: Diatech Pty. Ltd.).
Written Opinion issued Oct. 4, 2000 for PCT/AU1999/001110 filed on Dec. 14, 1999, which published as WO 2000/036141 on Jun. 22, 2000 (Applicant: Diatech Pty. Ltd.).
Notice of Abandonment issued Feb. 13, 2008 for Canadian Patent Application No. 2510587 filed on Dec. 19, 2003 (Applicant: Qiagen GmBH).
Reply to Rule 124(4) Communication issued Dec. 21, 2010 for European Patent Application No. 03799976 filed on Dec. 19, 2003 (Applicant: Qiagen GmBH).
Minutes of Oral Proceedings issued Oct. 18, 2010 for European Patent Application No. 03799976 filed on Dec. 19, 2003 (Applicant: Qiagen GmBH).
Brief Communication issued Sep. 10, 2010 for European Patent Application No. 03799976 filed on Dec. 19, 2003 (Applicant: Qiagen GmBH).
Written Submissions including 1st-4th Auxiliary Requests filed Aug. 23, 2010 for European Patent Application No. 03799976 filed on Dec. 19, 2003 (Applicant: Qiagen GmBH).
Summons to Attend Oral Proceedings issued May 6, 2010 for European Patent Application No. 03799976 filed on Dec. 19, 2003 (Applicant: Qiagen GmBH).
Response to Art. 94(3) EPC Communication filed Aug. 13, 2009 for European Patent Application No. 03799976 filed on Dec. 19, 2003 (Applicant: Qiagen GmBH).
Art. 94(3) EPC Communication issued May 14, 2009 for European Patent Application No. 03799976 filed on Dec. 19, 2003 (Applicant: Qiagen GmBH).
Response to Art. 94(3) EPC Communication filed Jun. 2, 2008 for European Patent Application No. 03799976 filed on Dec. 19, 2003 (Applicant: Qiagen GmBH).
Art. 94(3) EPC Communication issued Apr. 18, 2008 for European Patent Application No. 03799976 filed on Dec. 19, 2003 (Applicant: Qiagen GmBH).
Response to Art. 96(2) EPC Communication filed Dec. 17, 2007 for European Patent Application No. 03799976 filed on Dec. 19, 2003 (Applicant: Qiagen GmBH).
Art. 96(2) EPC Communication issued Aug. 22, 2007 for European Patent Application No. 03799976 filed on Dec. 19, 2003 (Applicant: Qiagen GmBH).
Response to Art. 96(1) Communication filed Jun. 29, 2007 for European Patent Application No. 03799976 filed on Dec. 19, 2003 (Applicant: Qiagen GmBH).
Art. 96(1) EPC Communication issued May 7, 2007 for European Patent Application No. 03799976 filed on Dec. 19, 2003 (Applicant: Qiagen GmBH).
Supplementary EPO Search Report issued Apr. 18, 2007 for European Patent. Application No. 03799976 filed on Dec. 19, 2003 (Applicant: Qiagen GmBH).
Claim Set filed Sep. 22, 2010 for European Patent Application No. 10178502 filed Dec. 19, 2003 (Applicant: Qiagen GmBH).
Examination Report issued Mar. 23, 2010 for Japanese Patent Application No. 2005510007 filed on Dec. 19, 2003 (Applicant: Qiagen GmBH).
Amended Set of Claims filed Feb. 26, 2010 for Japanese Patent Application No. 2005510007 filed on Dec. 19, 2003 (Applicant: Qiagen GmBH).
Examination Report issued an Examination Report Nov. 4, 2009 for Japanese Patent Application No. 2005510007 filed on Dec. 19, 2003 (Applicant: Qiagen GmBH).
Claim Set filed Feb. 26, 2010 for Japanese Patent Application No. 2010042086 filed on Dec. 19, 2003 (Applicant: Qiagen GmBH).
International Search Report issued Apr. 4, 2005 for PCT/US2003/040364 filed Dec. 19, 2003, which published as WO 2004/058987 on Jul. 15, 2004 (Applicant: Qiagen GmBH).
Response to Office Action filed May 26, 2010 for U.S. Appl. No. 10/327,602 filed on Dec. 20, 2002 (Inventors: Lasken et al.).
Notice of Appeal filed Apr. 27, 2010 for U.S. Appl. No. 10/327,602 filed on Dec. 20, 2002 (Inventors: Lasken et al.).
Interview Summary issued Dec. 24, 2009 for U.S. Appl. No. 10/327,602 filed on Dec. 20, 2002 (Inventors: Lasken et al.).
Supplemental Non-Final Rejection filed Oct. 27, 2009 for U.S. Appl. No. 10/327,602 filed on Dec. 20, 2002 (Inventors: Lasken et al.).
Non-Final Rejection issued Oct. 15, 2009 for U.S. Appl. No. 10/327,602 filed on Dec. 20, 2002 (Inventors: Lasken et al.).
Amendment and Response to Final Office Action filed Sep. 10, 2009 for U.S. Appl. No. 10/327,602 filed on Dec. 20, 2002 (Inventors: Lasken et al.).
Final Rejection issued Jun. 10, 2009 for U.S. Appl. No. 10/327,602 filed on Dec. 20, 2002 (Inventors: Lasken et al.).
Amendment and Response filed Mar. 31, 2009 for U.S. Appl. No. 10/327,602 filed on Dec. 20, 2002 (Inventors: Lasken et al.).
Preliminary Amendment filed Aug. 11, 1998 for U.S. Appl. No. 09/132,553 filed on Aug. 11, 1998 (Inventors: Lizardi et al.).
Preliminary Amendment filed Aug. 23, 2000 for U.S. Appl. No. 09/644,723 filed on Aug. 23, 2000 (Inventors:. Lizardi et al.).
Preliminary Amendment filed Aug. 11, 1998 for U.S. Appl. No. 09/132,552 filed on Aug. 11, 1998 (Inventors: Lizardi et al.).
Preliminary Amendment filed Jan. 2, 2002 for U.S. Appl. No. 10/038,718 filed on Jan. 2, 2002 (Inventors: Lizardi et al.).
Certificate of Correction issued Oct. 26, 2010 for U.S. Appl. No. 10/896,513 filed on Jul. 22, 2004 (Inventors: Lizardi et al.).
Issue Notification issued Oct. 28, 2009 for U.S. Appl. No. 10/896,513 filed on Jul. 22, 2004 (Inventors: Lizardi et al.).
Notice of Allowance issued Jul. 9, 2009 for U.S. Appl. No. 10/896,513 filed on Jul. 22, 2004 (Inventors: Lizardi et al.).
Amendment and Response filed Mar. 26, 2009 for U.S. Appl. No. 10/896,513 filed on Jul. 22, 2004 (Inventors: Lizardi et al.).
Interview Summary issued Mar. 12, 2009 for U.S. Appl. No. 10/896,513 filed on Jul. 22, 2004 (Inventors: Lizardi et al.).
Interview Summary issued Jun. 13, 2008 for U.S. Appl. No. 10/896,513 filed on Jul. 22, 2004 (Inventors: Lizardi et al.).
Preliminary Amendment filed Jan. 25, 2005 for U.S. Appl. No. 10/896,513 filed on Jul. 22, 2004 (Inventors: Lizardi et al.).
Communication regarding Expiry of Opposition Time Period issued Nov. 15, 2008 for European Patent Application No. 98952147.1 filed on Oct. 8, 1998 (Applicant: Yale University).
Brief Communication re: Request for Amendment of Application issued Nov. 2, 2007 for European Patent Application No. 98952147.1 filed on Oct. 8, 1998 (Applicant: Yale University).
Response to Written Opinion filed. Oct. 18, 1999 for PCT/US1998/021177 filed on Oct. 8, 1998, which published as WO 1999/018241 on Apr. 15, 1999 (Applicant: Yale University).
Written Opinion issued Jul. 20, 1999 for PCT/US1998/021177 filed on Oct. 8, 1998, which published as WO 1999/018241 on Apr. 15, 1999 (Applicant: Yale University).
Office Communication issued May 3, 2000 for U.S. Appl. No. 08/946,732 filed on Oct. 8, 1997 (Inventors: Lizardi et al.).
Preliminary Amendment filed Sep. 17, .1999 for U.S. Appl. No. 09/397,915 filed on Sep. 17, 1999 (Inventors: Lizardi et al.).
Preliminary Amendment filed Jul. 23, 2001 for U.S. Appl. No. 09/911,226 filed on Jul. 23, 2001 (Inventors: Lizardi et al.).
Notice of Abandonment issued Oct. 28, 2009 for U.S. Appl. No. 10/700,018 filed on Nov. 3, 2003 (Inventors: Lizardi et al.).
Advisory Action issued Apr. 2, 2009 for U.S. Appl. No. 10/700,018 filed on Nov. 3, 2003 (Inventors: Lizardi et al.).
Notice of Appeal filed Mar. 13, 2009 for U.S. Appl. No. 10/700,018 filed on Nov. 3, 2003 (Inventors: Lizardi et al.).
Amendment after Final Rejection filed Jan. 27, 2009 for U.S. Appl. No. 10/700,018 filed on Nov. 3, 2003 (Inventors: Lizardi et al.).

* cited by examiner

METHOD OF WHOLE GENOME AMPLIFICATION WITH REDUCED ARTIFACT PRODUCTION

FIELD OF THE INVENTION

The disclosed invention is generally in the field of nucleic acid amplification and more specifically involves reduced artifact production in nucleic acid amplification reactions.

BACKGROUND OF THE INVENTION

MDA of genomic DNA or circularized bacterial or plasmid DNA can be carried out using random primers at a temperature which is optimal for the DNA polymerase. Generally, this is in a lower temperature range, such as 30-34° C. The DNA to be amplified can be referred to as, for example, the target sequence, template, specific template, input DNA, template DNA, and specific input DNA. The goal of MDA is to amply this input DNA. However, DNA polymerase also can produce undesirable artifacts during these MDA reactions. Such artifacts produced by DNA polymerase and random primers at temperatures that are optimal for the DNA polymerase activity are also observed in other amplification techniques, such as rolling circle amplification (RCA) (examples include multiply-primed RCA, multiply-primed RCA of circular DNA circularized cDNA in isothermal total transcript amplification (ITTA) and multiply-primed RCA of circularized dsDNA using random hexamer and sequence specific primers). The defining characteristic of the artifact DNA is that it does not represent the specific sequence of the input DNA. In fact, the artifact DNA can be produced in the absence of any input DNA (as in the case of control reactions). This is problematic since control reactions lacking input DNA are often carried out with the expectation that no product DNA will be synthesized. Therefore, it would be advantageous to reduce or eliminate the artifact synthesis. Artifact DNA is generally of high molecular weight and therefore is often indistinguishable from the desired specific amplified DNA based on size. In the case where specific input DNA is present, the artifact DNA product can be generated and interferes with the desired use of the specific DNA product, and again, reduction or elimination of artifact production would be beneficial.

In contrast to the low molecular weight artifacts generated during polymerase chain reaction (PCR), referred to as primer dimers, the MDA artifacts are of high molecular weight with lengths ranging from several hundred basepairs to greater than 20 kb. Similar high molecular weight artifacts have also been described for other isothermal amplification systems such as ERCA (PCT/AU99/01110 (Hafner)). Contaminating nucleic acids in DNA polymerase preparations are one of the possible source of undesired template for the generation of these artifacts.

BRIEF SUMMARY OF THE INVENTION

Disclosed are compositions and methods for amplification of nucleic acid sequences of interest with greater efficiency and fidelity. The disclosed method relates to isothermal amplification techniques, such as Multiple Displacement Amplification (MDA), where the generation of DNA artifacts is decreased or eliminated. Generally, this can be accomplished by carrying out the reaction at elevated temperature. In particularly useful embodiments of the method, sugars and/or other additives can be used to stabilized the polymerase at high temperature.

It has been discovered that generation of high molecular weight artifacts, in an isothermal amplification procedure, is substantially reduced or eliminated while still allowing the desired amplification of input DNA by carrying out the reaction at a higher temperature and, optionally, in the presence of one or more additives. For example, the amplification reaction can be carried out in the presence of sugars at a temperature that is higher then the normal optimal temperature for the DNA polymerase being used. It also has been discovered that isothermal amplification reactions can produce amplification products of high quality, such as low amplification bias, if performed at a higher temperature and, optionally, in the presence of one or more additives.

The disclosed method fundamentally differs from techniques designed to eliminate the generation of primer dimer artifacts in PCR. In the case of PCR, an increase in elongation or primer annealing temperature produces less primer dimers relative to priming of specific input DNA template. In contrast, artifacts addressed by the disclosed method are believed to be derived from minute amounts of contaminating DNA, such as plasmid cloning vectors known to be present in recombinant proteins, such as DNA polymerases, or from trace contaminating DNA present in typical molecular biology laboratories in aerosol form or on equipment or in reagents. This complicates efforts to distinguish contaminant template from specific input template. It has been discovered that artifactual DNA synthesis can be reduced or eliminated by performing isothermal amplification reactions, such as MDA reactions, at elevated reaction temperatures, such that amplification of the specific input template is favored over amplification of contaminating template.

As an illustrative example, MDA of genomic DNA or circularized bacterial or plasmid DNA can be carried out using random hexamer primers and Phi29 DNA polymerase at a temperature which is optimal for Phi29 DNA polymerase activity (30-34° C.). DNA templates (input DNA), such as genomic DNA, are added to the reaction for amplification. However, Phi29 DNA polymerase also can produce undesirable artifacts during these MDA reactions. Generation of such artifacts by Phi29 DNA polymerase and random hexamer primers at temperatures that are optimal for Phi29 DNA polymerase activity (30-34° C.) are also observed in other isothermal amplification reactions, such as multiply-primed RCA of circularized cDNA in isothermal total transcript amplification (ITTA) and multiply-primed RCA of circularized dsDNA using random hexamer and sequence specific primers. The disclosed method and compositions can be used in MDA reactions with hexamer primers and Phi29 DNA polymerase to produce amplification products with reduced or undetectable levels of artifactual DNA.

Some forms of the methods are based on strand displacement replication of the nucleic acid sequences by multiple primers. Such forms of the disclosed method generally involve incubating nucleic acids comprising target sequences at an elevated temperature in the presence of a thermolabile nucleic acid polymerase having strand displacement activity, an additive, and a set of primers, under conditions promoting replication of the nucleic acids. Replication of the nucleic acids results in replicated strands. During replication at least one of the replicated nucleic acid strands is displaced by strand displacement replication of another replicated strand. Formation of replicated strands from the target sequences is favored over formation of replicated strands from non-target sequences.

Disclosed is a method of amplifying nucleic acids, the method comprising incubating nucleic acids comprising target sequences at an elevated temperature in the presence of a thermolabile nucleic acid polymerase having strand displacement activity, an additive, and a set of primers, under conditions promoting replication of the nucleic acids. Replication of the nucleic acids results in replicated strands. During replication at least one of the replicated nucleic acid strands is displaced by strand displacement replication of another replicated strand. Formation of replicated strands from the target sequences is favored over formation of replicated strands from non-target sequences.

Also disclosed is a method of amplifying a whole genome, the method comprising exposing cells to alkaline conditions to form a cell lysate, reducing the pH of the cell lysate to form a stabilized cell lysate, and incubating stabilized cell lysate at an elevated temperature in the presence of a thermolabile nucleic acid polymerase having strand displacement activity, an additive, and a set of primers, under conditions promoting replication of the nucleic acids. Replication of the nucleic acids results in replicated strands. During replication at least one of the replicated nucleic acid strands is displaced by strand displacement replication of another replicated strand. Formation of replicated strands from the target sequence is favored over formation of replicated strands from non-target sequences. The cell lysate comprises a whole genome.

Also disclosed is a method of performing strand displacement nucleic acid synthesis at an elevated temperature, the method comprising mixing thermolabile nucleic acid polymerase having strand-displacement activity, nucleic acids comprising target sequences, a set of primers, and an additive, and incubating at an elevated temperature and under conditions favoring hybridization of the primers to the target sequences and extension of the primers by the addition of nucleotides sequentially to the 3' end of the primer in a template-dependent manner, wherein the extension results in replication of the target sequences.

Also disclosed is a method of amplifying a whole genome, the method comprising exposing cells to alkaline conditions to form a cell lysate, wherein the cell lysate comprises a whole genome, reducing the pH of the cell lysate to form a stabilized cell lysate, and incubating stabilized cell lysate at an elevated temperature in the presence of a thermolabile nucleic acid polymerase having strand displacement activity, an additive, a set of primers, and deoxyribonucleotide triphosphates under conditions promoting replication of nucleic acids. During replication at least one of the replicated nucleic acid strands is displaced by strand displacement replication of another replicated strand. Formation of template-dependent extension products in the replication reaction is favored over formation of non-templated product.

Also disclosed is a method of performing strand displacement nucleic acid synthesis at an elevated temperature, the method comprising mixing thermolabile nucleic acid polymerase having strand-displacement activity, single-stranded template nucleic acid, a set of primers, deoxyribonucleotide triphosphates and an additive, and incubating at an elevated temperature and under conditions favoring hybridization of primer to template nucleic acid and extension of primer by the addition of nucleotides sequentially to the 3' end of the primer in a template-dependent manner, wherein said polymerization results in replication of said template nucleic acid.

Also disclosed is a method of amplifying nucleic acids, the method comprising incubating nucleic acids at an elevated temperature in the presence of a thermolabile nucleic acid polymerase having strand displacement activity, an additive, a set of primers, and deoxyribonucleotide triphosphates under conditions promoting replication of nucleic acids. During replication at least one of the replicated nucleic acid strands is displaced by strand displacement replication of another replicated strand. Formation of template-dependent extension products in the replication reaction is favored over formation of non-templated product.

Also disclosed is a kit for amplifying nucleic acids, the kit comprising a thermolabile nucleic acid polymerase having strand displacement activity, an additive, and a set of primers, wherein incubating nucleic acids comprising target sequences at an elevated temperature in the presence of the thermolabile nucleic acid polymerase, the additive, and the set of primers under conditions promoting replication of the nucleic acids results in replicated strands and in formation of replicated strands from the target sequences in favor of formation of replicated strands from non-target sequences.

The disclosed methods can be performed on any desired samples. For example, the disclosed methods can be performed using samples that contain or are suspected of containing nucleic acids. Some forms of the disclosed methods do not require knowledge of any sequence present in a sample in order to amplify nucleic acids in the sample. Accordingly, some forms of the disclosed methods can be used to determine if a sample contains nucleic acids. If amplification products are produced when the method is performed, the sample contains nucleic acids. The disclosed methods can be performed on cells and on nucleic acid samples, including crude nucleic acid samples, partially purified nucleic acid sample, and purified nucleic acid samples.

In some forms of the disclosed method, the primers can be hexamer primers, the DNA polymerase can be φ29 DNA polymerase, or both. Such short primers are easier to produce as a complete set of primers of random sequence (random primers) than longer primers because there are fewer separate species of primers in a pool of shorter primers. The above features are especially useful in whole genome strand displacement amplification (WGSDA).

In some forms of the disclosed method, the method includes labeling of the replicated strands (that is, the strands produced in multiple displacement amplification) using terminal deoxynucleotidyl transferase. The replicated strands can be labeled by, for example, the addition of modified nucleotides, such as biotinylated nucleotides, fluorescent nucleotides, 5 methyl dCTP, bromodeoxyuridine triphosphate (BrdUTP), or 5-(3-aminoallyl)-2'-deoxyuridine 5'-triphosphates, to the 3' ends of the replicated strands. The replicated strands can also be labeled by incorporating modified nucleotides during replication. Probes replicated in this manner are particularly useful for hybridization, including use in microarray formats.

Following amplification, the amplified sequences can be used for any purpose, such as uses known and established for PCR amplified sequences. For example, amplified sequences can be detected using any of the conventional detection systems for nucleic acids such as detection of fluorescent labels, enzyme-linked detection systems, antibody-mediated label detection, and detection of radioactive labels. A preferred form of labeling involves labeling of the replicated strands (that is, the strands produced in multiple displacement amplification) using terminal deoxynucleotidyl transferase. The replicated strands can be labeled by, for example, the addition of modified nucleotides, such as biotinylated nucleotides, fluorescent nucleotides, 5 methyl dCTP, BrdUTP, or 5-(3-aminoallyl)-2'-deoxyuridine 5'-triphosphates, to the 3' ends of the replicated strands.

It is an object of the disclosed invention to provide a method and kits for improving specific input template-dependent synthesis over artifact DNA synthesis.

It is another object of the disclosed invention to provide a method and kits that produce amplification products with reduced or undetectable levels of artifactual nucleic acids.

It is an object of the disclosed invention to provide a method of amplifying a target nucleic acid sequence in a continuous, isothermal reaction with reduced or undetectable levels of artifactual nucleic acids.

It is another object of the disclosed invention to provide a method of amplifying an entire genome or other highly complex nucleic acid sample in a continuous, isothermal reaction with reduced or undetectable levels of artifactual nucleic acids.

DETAILED DESCRIPTION OF THE INVENTION

Figure 1:
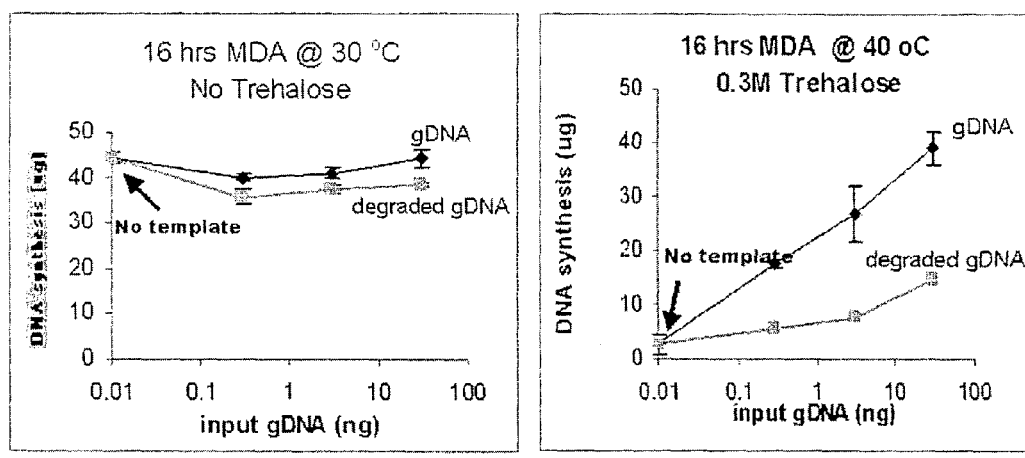
FIG. 1 is a graph of DNA synthesis by MDA reaction carried out for 16 hrs. using varying amounts (0, 0.3 ng, 3 ng and 30 ng) of intact genomic DNA (gDNA) or genomic DNA that was degraded by heating at 85° C. for 10 minutes (degraded gDNA) as the input template. The MDA reaction was either carried out at 30° C. in the absence of 0.3 M Trehalose or at 40° C. in the presence of 0.3 M Trehalose.

The disclosed method makes use of certain materials and procedures which allow amplification of target nucleic acid sequences and whole genomes or other highly complex nucleic acid samples. These materials and procedures are described in detail below.

Materials

A. Additives

Additives for use in the disclosed amplification method are any compound, composition, or combination that can allow a thermolabile nucleic acid polymerase to perform template-dependent polymerization at an elevated temperature. Additives generally have a thermostabilizing effect on the nucleic acid polymerase. Additives allow a thermolabile nucleic acid polymerase to be used at temperature above the normal active range of the polymerase. Useful additives include sugars, chaperones, proteins, saccharides, amino acids, polyalcohols and their derivatives, and other osmolytes. Useful sugars include trehalose, glucose and sucrose. Useful saccharides include oligosaccharides and monosaccharides such as trehalose, maltose, glucose, sucrose, lactose, xylobiose, agarobiose, cellobiose, levanbiose, quitobiose, 2-β-glucuronosyl-glucuronic acid, allose, altrose, galactose, gulose, idose, mannose, talose, sorbitol, levulose, xylitol, arabitol, and polyalcohols such as glycerol, ethylene glycol, polyethylene glycol. Useful amino acids and derivatives thereof include $N^e$-acetyl-β-lysine, alanine, γ-aminobutyric acid, betaine, $N^\alpha$-carbamoyl-L-glutamine 1-amide, choline, dimethylthetine, ecotine (1,4,5,6-tetrahydro-2-methyl-4-pirymidine carboxilic acid), glutamate, β-glutammine, glycine, octopine, proline, sarcosine, taurine and trymethylamine N-oxide (TMAO). Useful chaperone proteins include chaperone proteins of Thermophilic bacteria and heat shock proteins such as HSP 90, HSP 70 and HSP 60. Other useful additives include sorbitol, mannosylglycerate, diglycerol phosphate, and cyclic-2,3-diphosphoglycerate. Combinations of compounds and compositions can be used as additives.

As used herein, an elevated temperature is a temperature at or above which a given nucleic acid polymerase is notably inactivated in the absence of an additive, dNTPs, and template nucleic acid. Thus, what constitutes an elevated temperature depends on the particular nucleic acid polymerase. As used herein, notable inactivation refers to a reduction in activity of 40% or more. Substantial inactivation refers to a reduction in activity of 60% or more. Significant inactivation refers to a reduction in activity of 80% or more.

As used herein, a thermolabile nucleic acid polymerase is a nucleic acid polymerase that is notably inactivated at the temperature at which an amplification reaction is carried out in the absence of an additive, dNTPs, and template nucleic acid. Thus, whether a nucleic acid polymerase is thermolabile depends on the temperature at which an amplification reaction is carried out. Note that as used herein, thermolability does not require denaturation or irreversible inactivation of a polymerase. All that is required is that the polymerase be notably incapable of performing template-dependent polymerization at the temperature at which an amplification reaction is carried out in the absence of an additive.

B. Primers

Primers for use in the disclosed amplification method are oligonucleotides having sequence complementary to target sequences. This sequence is referred to as the complementary portion of the primer. The complementary portion of a primer can be any length that supports specific and stable hybridization between the primer and the target sequence under the reaction conditions. Generally, for reactions at 40° C., this can be 12 to 35 nucleotides long or 18 to 24 nucleotides long. For whole genome amplification, the primers can be from 5 to 60 nucleotides long, and in particular, can be 5, 6, 7, 8, 9, 10, 11, 12, 13, 14, 15, 16, 17, 18, 19, and/or 20 nucleotides long.

For some forms of the disclosed method, such as those using primers or random or degenerate sequence (that is, use of a collection of primers having a variety of sequences), primer hybridization need not be specific. In such cases the primers need only be effective in priming synthesis. For example, in whole genome amplification specificity of priming is not essential since the goal generally is to amplify all sequences equally. Sets of random or degenerate primers can be composed of primers 5, 6, 7, 8, 9, 10, 11, 12, 13, 14, 15, 16, 17, 18, 19, and/or 20 nucleotides long or more. Primers six nucleotides long are referred to as hexamer primers. Preferred primers for whole genome amplification are random hexamer primers, for example, random hexamer primers where every possible six nucleotide sequence is represented in the set of primers. Similarly, sets of random primers of other particular lengths, or of a mixture of lengths preferably contain every possible sequence the length of the primer, or, in particular, the length of the complementary portion of the primer. Use of random primers is described in U.S. Pat. No. 5,043,272 and U.S. Pat. No. 6,214,587.

The disclosed primers can have one or more modified nucleotides. Such primers are referred to herein as modified primers. Modified primers have several advantages. First, some forms of modified primers, such as RNA/2'-O-methyl RNA chimeric primers, have a higher melting temperature (Tm) than DNA primers. This increases the stability of primer hybridization and will increase strand invasion by the primers. This will lead to more efficient priming. Also, since the primers are made of RNA, they will be exonuclease resistant. Such primers, if tagged with minor groove binders at their 5' end, will also have better strand invasion of the template dsDNA.

Chimeric primers can also be used. Chimeric primers are primers having at least two types of nucleotides, such as both deoxyribonucleotides and ribonucleotides, ribonucleotides and modified nucleotides, or two different types of modified nucleotides. One form of chimeric primer is peptide nucleic acid/nucleic acid primers. For example, 5'-PNA-DNA-3' or 5'-PNA-RNA-3' primers may be used for more efficient strand invasion and polymerization invasion. The DNA and RNA portions of such primers can have random or degenerate sequences. Other forms of chimeric primers are, for example, 5'-(2'-O-Methyl) RNA-RNA-3' or 5'-(2'-O-Methyl) RNA-DNA-3'.

Many modified nucleotides (nucleotide analogs) are known and can be used in oligonucleotides. A nucleotide analog is a nucleotide which contains some type of modification to either the base, sugar, or phosphate moieties. Modifications to the base moiety would include natural and synthetic modifications of A, C, G, and T/U as well as different purine or pyrimidine bases, such as uracil-5-yl, hypoxanthin-9-yl (I), and 2-aminoadenin-9-yl. A modified base includes but is not limited to 5-methylcytosine (5-me-C), 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Additional base modifications can be found for example in U.S. Pat. No. 3,687,808, Englisch et al., Angewandte Chemie, International Edition, 1991, 30, 613, and Sanghvi, Y. S., Chapter 15, Antisense Research and Applications, pages 289-302, Crooke, S. T. and Lebleu, B. ed., CRC Press, 1993. Certain nucleotide analogs, such as 5-substituted pyrimidines, 6-azapyrimidines and N-2, N-6 and O-6 substituted purines, including 2-aminopropyladenine, 5-propynyluracil and 5-propynylcytosine. 5-methylcytosine can increase the stability of duplex formation. Other modified bases are those that function as universal bases. Universal bases include 3-nitropyrrole and 5-nitroindole. Universal bases substitute for the normal bases but have no bias in base pairing. That is, universal bases can base pair with any other base. Primers composed, either in whole or in part, of nucleotides with universal bases are useful for reducing or eliminating amplification bias against repeated sequences in a target sample. This would be useful, for example, where a loss of sequence complexity in the amplified products is undesirable. Base modifications often can be combined with for example a sugar modification, such as 2'-O-methoxyethyl, to achieve unique properties such as increased duplex stability. There are numerous U.S. Pat. Nos. 4,845,205; 5,130,302; 5,134,066; 5,175,273; 5,367,066; 5,432,272; 5,457,187; 5,459,255; 5,484,908; 5,502,177; 5,525,711; 5,552,540; 5,587,469; 5,594,121, 5,596,091; 5,614,617; and 5,681,941, which detail and describe a range of base modifications. Each of these patents is herein incorporated by reference.

Nucleotide analogs can also include modifications of the sugar moiety. Modifications to the sugar moiety would include natural modifications of the ribose and deoxyribose as well as synthetic modifications. Sugar modifications include but are not limited to the following modifications at the 2' position: OH; F; O-, S-, or N-alkyl; O-, S-, or N-alkenyl; O-, S- or N-alkynyl; or O-alkyl-O-alkyl, wherein the alkyl, alkenyl and alkynyl may be substituted or unsubstituted C1 to C10, alkyl or C2 to C10 alkenyl and alkynyl. 2' sugar modifications also include but are not limited to —O[(CH$_2$)n O]m CH$_3$, —O(CH$_2$)n OCH$_3$, —O(CH$_2$)n NH$_2$, —O(CH$_2$)n CH$_3$, —O(CH$_2$)n —ONH$_2$, and —O(CH$_2$)nON[(CH$_2$)n CH$_3$)]$_2$, where n and m are from 1 to about 10.

Other modifications at the 2' position include but are not limited to: C1 to C10 lower alkyl, substituted lower alkyl, alkaryl, aralkyl, O-alkaryl or O-aralkyl, SH, SCH$_3$, OCN, Cl, Br, CN, CF$_3$, OCF$_3$, SOCH$_3$, SO$_2$ CH$_3$, ONO$_2$, NO$_2$, N$_3$, NH$_2$, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. Similar modifications may also be made at other positions on the sugar, particularly the 3' position of the sugar on the 3' terminal nucleotide or in 2'-5' linked oligonucleotides and the 5' position of 5' terminal nucleotide. Modified sugars would also include those that contain modifications at the bridging ring oxygen, such as CH$_2$ and S. Nucleotide sugar analogs may also have sugar mimetics such as cyclobutyl moieties in place of the pentofuranosyl sugar. There are numerous United States patents that teach the preparation of such modified sugar structures such as U.S. Pat. Nos. 4,981,957; 5,118,800; 5,319,080; 5,359,044; 5,393,878; 5,446,137; 5,466,786; 5,514,785; 5,519,134; 5,567,811; 5,576,427; 5,591,722; 5,597,909; 5,610,300; 5,627,053; 5,639,873; 5,646,265; 5,658,873; 5,670,633; and 5,700,920, each of which is herein incorporated by reference in its entirety.

Nucleotide analogs can also be modified at the phosphate moiety. Modified phosphate moieties include but are not limited to those that can be modified so that the linkage between two nucleotides contains a phosphorothioate, chiral phosphorothioate, phosphorodithioate, phosphotriester, aminoalkylphosphotriester, methyl and other alkyl phosphonates including 3'-alkylene phosphonate and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates. It is understood that these phosphate or modified phosphate linkages between two nucleotides can be through a 3'-5' linkage or a 2'-5' linkage, and the linkage can contain inverted polarity such as 3'-5' to 5'-3' or 2'-5' to 5'-2'. Various salts, mixed salts and free acid forms are also included. Numerous United States patents teach how to make and use nucleotides containing modified phosphates and include but are not limited to, U.S. Pat. Nos. 3,687,808; 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050, each of which is herein incorporated by reference.

It is understood that nucleotide analogs need only contain a single modification, but may also contain multiple modifications within one of the moieties or between different moieties.

Nucleotide substitutes are molecules having similar functional properties to nucleotides, but which do not contain a phosphate moiety, such as peptide nucleic acid (PNA). Nucleotide substitutes are molecules that will recognize and hybridize to complementary nucleic acids in a Watson-Crick or Hoogsteen manner, but which are linked together through a moiety other than a phosphate moiety. Nucleotide substitutes are able to conform to a double helix type structure when interacting with the appropriate target nucleic acid.

Nucleotide substitutes are nucleotides or nucleotide analogs that have had the phosphate moiety and/or sugar moieties replaced. Nucleotide substitutes do not contain a standard phosphorus atom. Substitutes for the phosphate can be for example, short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts. Numerous United States patents disclose how to make and use these types of phosphate replacements and include but are not limited to U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439, each of which is herein incorporated by reference.

It is also understood in a nucleotide substitute that both the sugar and the phosphate moieties of the nucleotide can be replaced, by for example an amide type linkage (aminoethylglycine) (PNA). U.S. Pat. Nos. 5,539,082; 5,714,331; and 5,719,262 teach how to make and use PNA molecules, each of which is herein incorporated by reference. (See also Nielsen et al., Science 254:1497-1500 (1991)).

Primers can be comprised of nucleotides and can be made up of different types of nucleotides or the same type of nucleotides. For example, one or more of the nucleotides in a primer can be ribonucleotides, 2'-O-methyl ribonucleotides, or a mixture of ribonucleotides and 2'-O-methyl ribonucleotides; about 10% to about 50% of the nucleotides can be ribonucleotides, 2'-O-methyl ribonucleotides, or a mixture of ribonucleotides and 2'-O-methyl ribonucleotides; about 50% or more of the nucleotides can be ribonucleotides, 2'-O-methyl ribonucleotides, or a mixture of ribonucleotides and 2'-O-methyl ribonucleotides; or all of the nucleotides are ribonucleotides, methyl ribonucleotides, or a mixture of ribonucleotides and 2'-O-methyl ribonucleotides. The nucleotides can be comprised of bases (that is, the base portion of the nucleotide) and can (and normally will) comprise different types of bases. For example, one or more of the bases can be universal bases, such as 3-nitropyrrole or 5-nitroindole; about 10% to about 50% of the bases can be universal bases; about 50% or more of the bases can be universal bases; or all of the bases can be universal bases.

Primers may, but need not, also contain additional sequence at the 5' end of the primer that is not complementary to the target sequence. This sequence is referred to as the non-complementary portion of the primer. The non-complementary portion of the primer, if present, serves to facilitate strand displacement during DNA replication. The non-complementary portion of the primer can also include a functional sequence such as a promoter for an RNA polymerase. The non-complementary portion of a primer may be any length, but is generally 1 to 100 nucleotides long, and preferably 4 to 8 nucleotides long. The use of a non-complementary portion is not preferred when random or partially random primers are used for whole genome amplification.

In the case of whole genome strand displacement amplification, it is preferred that a set of primers having random or partially random nucleotide sequences be used. In a nucleic acid sample of significant or substantial complexity, which is the preferred target sequence for WGSDA, specific nucleic acid sequences present in the sample need not be known and the primers need not be designed to be complementary to any particular sequence. Rather, the complexity of the nucleic acid sample results in a large number of different hybridization target sequences in the sample which will be complementary to various primers of random or partially random sequence. The complementary portion of primers for use in WGSDA can be fully randomized, have only a portion that is randomized, or be otherwise selectively randomized. Sets of primers having random or partially random sequences can be synthesized using standard techniques by allowing the addition of any nucleotide at each position to be randomized. It is also preferred that the sets of primers are composed of primers of similar length and/or hybridization characteristics.

A set of primers can include any desired number of primers of different nucleotide sequence. It is preferred that a set of primers include a plurality of primers. It is more preferred that a set of primers include 3 or more primers. It is still more preferred that a set of primers include 4 or more, 5 or more, 6 or more, or 7 or more primers. In general, the more primers used, the greater the level of amplification that will be obtained. There is no fundamental upper limit to the number of primers that a set of primers can have. However, for a given target sequence, the number of primers in a set of primers will generally be limited to the number of hybridization sites available in the target sequence. For example, if the target sequence is a 10,000 nucleotide DNA molecule and 20 nucleotide primers are used, there are 500 non-overlapping 20 nucleotide sites in the target sequence. Even more primers than this could be used if overlapping sites are either desired or acceptable. It is preferred that a set of primers include no more than about 300 primers. It is preferred that a set of primers include no more than about 200 primers. It is still more preferred that a set of primers include no more than about 100 primers. It is more preferred that a set of primers include no more than about 50 primers. It is most preferred that a set of primers include from 7 to about 50 primers. Any combination of the preferred upper and lower limits for the number of primers in a set of primers described above are specifically contemplated, including all intermediate ranges.

1. Detection Tags

The non-complementary portion of a primer can include sequences to be used to further manipulate or analyze amplified sequences. An example of such a sequence is a detection tag, which is a specific nucleotide sequence present in the non-complementary portion of a primer. Detection tags have sequences complementary to detection probes. Detection tags can be detected using their cognate detection probes. Detection tags become incorporated at the ends of amplified strands. The result is amplified DNA having detection tag sequences that are complementary to the complementary portion of detection probes. If present, there may be one, two, three, or more than three detection tags on a primer. It is preferred that a primer have one, two, three or four detection tags. Most preferably, a primer will have one detection tag. Generally, it is preferred that a primer have 10 detection tags or less. There is no fundamental limit to the number of detection tags that can be present on a primer except the size of the primer. When there are multiple detection tags, they may have the same sequence or they may have different sequences, with each different sequence complementary to a different detection probe. It is preferred that a primer contain detection tags that have the same sequence such that they are all complementary to a single detection probe. For some multiplex detection methods, it is preferable that primers contain up to six detection tags and that the detection tag portions have different sequences such that each of the detection tag portions is complementary to a different detection probe. A similar effect can be achieved by using a set of primers where each has a single different detection tag. The detection tags can each be any length that supports specific and stable hybridization between the detection tags and the detection probe. For this purpose, a length of 10 to 35 nucleotides is preferred, with a detection tag portion 15 to 20 nucleotides long being most preferred.

2. Address Tag

Another example of a sequence that can be included in the non-complementary portion of a primer is an address tag. An address tag has a sequence complementary to an address probe. Address tags become incorporated at the ends of amplified strands. The result is amplified DNA having address tag sequences that are complementary to the complementary portion of address probes. If present, there may be one, or more than one, address tag on a primer. It is preferred that a primer have one or two address tags. Most preferably, a primer will have one address tag. Generally, it is preferred that a primer have 10 address tags or less. There is no fundamental limit to the number of address tags that can be present on a primer except the size of the primer. When there are multiple address tags, they may have the same sequence or they may have different sequences, with each different sequence complementary to a different address probe. It is preferred that a primer contain address tags that have the same sequence such that they are all complementary to a single address probe. The address tag portion can be any length that supports specific and stable hybridization between the address tag and the address probe. For this purpose, a length between 10 and 35 nucleotides long is preferred, with an address tag portion 15 to 20 nucleotides long being most preferred.

C. Nucleic Acid Polymerases

Nucleic acid polymerases useful in multiple displacement amplification must be capable of displacing, either alone or in combination with a compatible strand displacement factor, a hybridized strand encountered during replication. Such polymerases are referred to herein as strand displacement nucleic acid polymerases and can be said to have strand displacement activity. It is preferred that a strand displacement nucleic acid polymerase lack a 5' to 3' exonuclease activity. Strand displacement is necessary to result in synthesis of multiple copies of a target sequence. A 5' to 3' exonuclease activity, if present, might result in the destruction of a synthesized strand. It is also preferred that nucleic acid polymerases for use in the disclosed method are highly processive. The suitability of a nucleic acid polymerase for use in the disclosed method can be readily determined by assessing its ability to carry out strand displacement replication. Useful nucleic acid polymerases for use in the disclosed method are DNA polymerases.

As used herein, a thermolabile nucleic acid polymerase is a nucleic acid polymerase that is notably inactivated at the temperature at which an amplification reaction is carried out in the absence of an additive, dNTPs, and template nucleic acid. Thus, whether a nucleic acid polymerase is thermolabile depends on the temperature at which an amplification reaction is carried out. Note that as used herein, thermolability does not require denaturation or irreversible inactivation of a polymerase. All that is required is that the polymerase be notably incapable of performing template-dependent polymerization at the temperature at which an amplification reaction is carried out in the absence of an additive.

As used herein, an elevated temperature is a temperature at or above which a given nucleic acid polymerase is notably inactivated in the absence of an additive, dNTPs, and template nucleic acid. Thus, what constitutes an elevated temperature depends on the particular nucleic acid polymerase. As used herein, notable inactivation refers to a reduction in activity of 40% or more. Substantial inactivation refers to a reduction in activity of 60% or more. Significant inactivation refers to a reduction in activity of 80% or more.

Useful thermolabile strand displacement DNA polymerases are bacteriophage φ29 DNA polymerase (U.S. Pat. Nos. 5,198,543 and 5,001,050 to Blanco et al.), Bst large fragment DNA polymerase (Exo(−) Bst; Aliotta et al., *Genet. Anal. (Netherlands)* 12:185-195 (1996)) and exo(−)Bca DNA polymerase (Walker and Linn, *Clinical Chemistry* 42:1604-1608 (1996)). Other useful thermolabile strand displacement polymerases include phage M2 DNA polymerase (Matsumoto et al., *Gene* 84:247 (1989)), phage φPRD1 DNA polymerase (Jung et al., *Proc. Natl. Acad. Sci. USA* 84:8287 (1987)), Klenow fragment of DNA polymerase I (Jacobsen et al., *Eur. J. Biochem.* 45:623-627 (1974)), T5 DNA polymerase (Chatterjee et al., *Gene* 97:13-19 (1991)), Sequenase (U.S. Biochemicals), PRD1 DNA polymerase (Zhu and Ito, *Biochim. Biophys. Acta.* 1219:267-276 (1994)), and T4 DNA polymerase holoenzyme (Kaboord and Benkovic, *Curr. Biol.* 5:149-157 (1995)). φ29 DNA polymerase is most preferred. Useful strand displacement DNA polymerases are bacteriophage φ29 DNA polymerase, Bst large fragment DNA polymerase and exo(−)Bca DNA polymerase. Other useful strand displacement polymerases include phage M2 DNA polymerase, phage φPRD1 DNA polymerase, exo(−)VENT DNA polymerase, Klenow fragment of DNA polymerase I, T5 DNA polymerase, Sequenase, and T4 DNA polymerase holoenzyme. φ29 DNA polymerase is most preferred.

Strand displacement can be facilitated through the use of a strand displacement factor, such as helicase. It is considered that any DNA polymerase that can perform strand displacement replication in the presence of a strand displacement factor is suitable for use in the disclosed method, even if the DNA polymerase does not perform strand displacement replication in the absence of such a factor. In particular, a nucleic acid polymerase that has strand displacement activity when used with a strand displacement factor is considered a nucleic acid polymerase with strand displacement activity when used with the strand displacement factor. Strand displacement factors useful in strand displacement replication include BMRF1 polymerase accessory subunit (Tsurumi et al., *J. Virology* 67(12):7648-7653 (1993)), adenovirus DNA-binding protein (Zijderveld and van der Vliet, *J. Virology* 68(2):1158-1164 (1994)), herpes simplex viral protein ICP8 (Boehmer and Lehman, *J. Virology* 67(2):711-715 (1993); Skaliter and Lehman, *Proc. Natl. Acad. Sci. USA* 91(22):10665-10669 (1994)); single-stranded DNA binding proteins (SSB; Rigler and Romano, *J. Biol. Chem.* 270:8910-8919 (1995)); phage T4 gene 32 protein (Villemain and Giedroc, *Biochemistry* 35:14395-14404 (1996); and calf thymus helicase (Siegel et al., *J. Biol. Chem.* 267:13629-13635 (1992)).

The ability of a polymerase to carry out strand displacement replication can be determined by using the polymerase in a strand displacement replication assay such as those described in Examples 1 and 5 of International Application No. WO 03/033724, which is hereby incorporated by reference. The assay in the examples can be modified as appropriate. For example, a helicase can be used instead of SSB. Such assays should be performed at a temperature suitable for optimal activity for the enzyme being used, for example, 32° C. for φ29 DNA polymerase, from 46° C. to 64° C. for exo(−) Bst DNA polymerase, or from about 60° C. to 70° C. for an enzyme from a hyperthermophylic organism. For assays from 60° C. to 70° C., primer length may be increased to provide a melting temperature appropriate for the assay temperature. Another useful assay for selecting a polymerase is the primer-block assay described in Kong et al., *J. Biol. Chem.* 268:1965-1975 (1993). The assay consists of a primer extension assay using an M13 ssDNA template in the presence or absence of an oligonucleotide that is hybridized upstream of the extending primer to block its progress. Enzymes able to displace the blocking primer in this assay are expected to be useful for the disclosed method.

D. Target Sequence

The target sequence, which is the object of amplification, can be any nucleic acid. The target sequence can include multiple nucleic acid molecules, such as in the case of whole genome amplification, multiple sites in a nucleic acid molecule, or a single region of a nucleic acid molecule. For multiple strand displacement amplification, generally the target sequence is a single region in a nucleic acid molecule or nucleic acid sample. For whole genome amplification, the target sequence is the entire genome or nucleic acid sample. A target sequence can be in any nucleic acid sample of interest. The source, identity, and preparation of many such nucleic acid samples are known. It is preferred that nucleic acid samples known or identified for use in amplification or detection methods be used for the method described herein. The nucleic acid sample can be, for example, a nucleic acid sample from one or more cells, tissue, or bodily fluids such as blood, urine, semen, lymphatic fluid, cerebrospinal fluid, or amniotic fluid, or other biological samples, such as tissue culture cells, buccal swabs, mouthwash, stool, tissues slices, biopsy aspiration, and archeological samples such as bone or mummified tissue. Target samples can be derived from any source including, but not limited to, eukaryotes, plants, animals, vertebrates, fish, mammals, humans, non-humans, bacteria, microbes, viruses, biological sources, serum, plasma, blood, urine, semen, lymphatic fluid, cerebrospinal fluid, amniotic fluid, biopsies, needle aspiration biopsies, cancers, tumors, tissues, cells, cell lysates, crude cell lysates, tissue lysates, tissue culture cells, buccal swabs, mouthwash, stool, mummified tissue, forensic sources, autopsies, archeological sources, infections, nosocomial infections, production sources, drug preparations, biological molecule productions, protein preparations, lipid preparations, carbohydrate preparations, inanimate objects, air, soil, sap, metal, fossils, excavated materials, and/or other terrestrial or extra-terrestrial materials and sources. The sample may also contain mixtures of material from one or more different sources. For example, nucleic acids of an infecting bacterium or virus can be amplified along with human nucleic acids when nucleic acids from such infected cells or tissues are amplified using the disclosed methods. Types of useful target samples include eukaryotic samples, plant samples, animal samples, vertebrate samples, fish samples, mammalian samples, human samples, non-human samples, bacterial samples, microbial samples, viral samples, biological samples, serum samples, plasma samples, blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, crude cell lysate samples, tissue lysate samples, tissue culture cell samples, buccal swab samples, mouthwash samples, stool samples, mummified tissue samples, forensic samples, autopsy samples, archeological samples, infection samples, nosocomial infection samples, production samples, drug preparation samples, biological molecule production samples, protein preparation samples, lipid preparation samples, carbohydrate preparation samples, inanimate object samples, air samples, soil samples, sap samples, metal samples, fossil samples, excavated material samples, and/or other terrestrial or extra-terrestrial samples.

For multiple strand displacement amplification, preferred target sequences are those which are difficult to amplify using PCR due to, for example, length or composition. For whole genome amplification, preferred target sequences are nucleic acid samples from a single cell. For multiple strand displacement amplification of concatenated DNA the target is the concatenated DNA. The target sequence can be either one or both strands of cDNA. The target sequences for use in the disclosed method are preferably part of nucleic acid molecules or samples that are complex and non-repetitive (with the exception of the linkers in linker-concatenated DNA and sections of repetitive DNA in genomic DNA).

Target nucleic acids can include damaged DNA and damaged DNA samples. For example, preparation of genomic DNA samples can result in damage to the genomic DNA (for example, degradation and fragmentation). This can make amplification of the genome or sequences in it both more difficult and provide less reliable results (by, for example, resulting in amplification of many partial and fragmented genomic sequences. Damaged DNA and damaged DNA samples are thus useful for the disclosed method of amplifying damaged DNA. Any degraded, fragmented or otherwise damaged DNA or sample containing such DNA can be used in the disclosed method.

E. Samples

Nucleic acid molecules, which are the object of amplification, can be any nucleic acid from any source. In general, the disclosed method is performed using a sample that contains (or is suspected of containing) nucleic acid molecules to be amplified. Samples containing, or suspected of containing, nucleic acid molecules can also be referred to as nucleic acid samples. Samples, such as nucleic acid samples can comprise target sequences. Cell and tissue samples are a form of nucleic acid sample. Samples for use in the disclosed methods can also be samples that are to be tested for the presence of nucleic acids (that is, samples that may or may not contain nucleic acids). For whole genome amplification, the sample can be all or a substantial portion of an entire genome. As used herein, a substantial portion of a genome refers to the presence of 90% or more of the sequences present in the entire genome. A sample, such as a nucleic acid sample or genomic nucleic acid sample, including or comprising a substantial portion of a genome refers to a sample including 90% or more of the sequences present in the entire genome. A genomic nucleic acid sample refers to any sample derived from genomic nucleic acids and including or comprising a notable portion of the entire genome. As used herein, a notable portion of a genome refers to the presence of 20% or more of the sequences present in the entire genome. A sample, such as a nucleic acid sample or genomic nucleic acid sample, including or comprising a notable portion of a genome refers to a sample including 20% or more of the sequences present in the entire genome. As used herein, a significant portion of a genome refers to the presence of 50% or more of the sequences present in the entire genome. A sample, such as a nucleic acid sample or genomic nucleic acid sample, including or comprising a significant portion of a genome refers to a sample including 50% or more of the sequences present in the entire genome. A genomic nucleic acid sample is a form of nucleic acid sample and a form of sample. Reference herein to a sample encompasses nucleic acid samples and genomic samples unless the context clearly indicates otherwise. Reference herein to a nucleic acid sample encompasses genomic nucleic acid samples unless the context clearly indicates otherwise.

A sample can comprise a genome, and the genome can comprise any fraction of the nucleic acids in the sample. The genome can comprise, for example, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99% of the nucleic acids in the sample.

The nucleic acids in a sample need not be pure to be amplified in the disclosed methods. Some forms of the disclosed methods are useful for amplifying impure nucleic acid samples, such as crude cell lysates. The nucleic acids in a sample or in a stabilized or neutralized sample can be, for example, less than 0.01% pure, less than 0.5% pure, less than 0.1% pure, less than 0.2% pure, less than 0.4% pure, less than 0.6% pure, less than 0.8% pure, less than 1% pure, less than 2% pure, less than 3% pure, less than 4% pure, less than 5% pure, less than 6% pure, less than 8% pure, less than 10% pure, less than 15% pure, less than 20% pure, less than 25% pure, less than 30% pure, less than 40% pure, or less than 50% pure by weight excluding water.

A nucleic acid sample can be any nucleic acid sample of interest. The source, identity, and preparation of many such nucleic acid samples are known. It is preferred that nucleic acid samples known or identified for use in amplification or detection methods be used for the method described herein. The nucleic acid sample can be, for example, a nucleic acid sample comprising or derived from one or more eukaryotes, plants, animals, vertebrates, fish, mammals, humans, non-humans, bacteria, microbes, viruses, biological sources, serum, plasma, blood, urine, semen, lymphatic fluid, cerebrospinal fluid, amniotic fluid, biopsies, needle aspiration biopsies, cancers, tumors, tissues, cells, cell lysates, crude cell lysates, tissue lysates, tissue culture cells, buccal swabs, mouthwash, stool, mummified tissue, forensic sources, autopsies, archeological sources, infections, nosocomial infections, production sources, drug preparations, biological molecule productions, protein preparations, lipid preparations, carbohydrate preparations, inanimate objects, air, soil, sap, metal, fossils, excavated materials, and/or other terrestrial or extra-terrestrial materials and sources. Types of useful nucleic acid samples include eukaryotic samples, plant samples, animal samples, vertebrate samples, fish samples, mammalian samples, human samples, non-human samples, bacterial samples, microbial samples, viral samples, biological samples, serum samples, plasma samples, blood samples, urine samples, semen samples, lymphatic fluid samples, cerebrospinal fluid samples, amniotic fluid samples, biopsy samples, needle aspiration biopsy samples, cancer samples, tumor samples, tissue samples, cell samples, cell lysate samples, crude cell lysate samples, tissue lysate samples, tissue culture cell samples, buccal swab samples, mouthwash samples, stool samples, mummified tissue samples, forensic samples, autopsy samples, archeological samples, infection samples, nosocomial infection samples, production samples, drug preparation samples, biological molecule production samples, protein preparation samples, lipid preparation samples, carbohydrate preparation samples, inanimate object samples, air samples, soil samples, sap samples, metal samples, fossil samples, excavated material samples, and/or other terrestrial or extra-terrestrial samples.

It has been discovered that it is unnecessary to have prior knowledge of whether or not a sample contains amplifiable nucleic acids. Some forms of the disclosed methods can be employed to test whether or not a sample suspected of containing nucleic acids actually does contain nucleic acids. Production of amplified DNA from such samples using the disclosed method is evidence that the sample contained nucleic acids. More generally, practice of the disclosed methods does not require any knowledge of any nucleic acid sequence in a sample. Thus, the disclosed methods can be used to amplify nucleic acids from any source, regardless of a lack of specific sequence information. This is in contrast to other amplification methods, such as PCR, where it is necessary to have prior information of at least a portion of the nucleic acid sequences believed to be present in the sample in order to perform the amplification. In this instance, the PCR amplification reaction will fail if the nucleic acids present in the sample are different from the expected sample nucleic acids. If a sample contains a mixture of nucleic acids, then nucleic acids of the appropriate type alone will be amplified in a PCR reaction, but not the other types of nucleic acids. In contrast, the disclosed methods provide for amplification of most or all of the nucleic acids present in the sample. The disclosed methods are equally adaptable to using samples that conventionally are not expected or believed to contain nucleic acids. For instance, serum or plasma from humans or other higher animals were believed to not contain free host nucleic acids. However, it was discovered that the disclosed methods could amplify nucleic acids present in such samples.

For whole genome amplification, preferred nucleic acid samples are nucleic acid samples from a single cell. The nucleic acid samples for use in some forms of the disclosed method are preferably nucleic acid molecules and samples that are complex and non-repetitive. Where the nucleic acid sample is a genomic nucleic acid sample, the genome can be the genome from any organism of interest. For example, the genome can be a viral genome, a bacterial genome, a eubacterial genome, an archae bacterial genome, a fungal genome, a microbial genome, a eukaryotic genome, a plant genome, an animal genome, a vertebrate genome, an invertebrate genome, an insect genome, a mammalian genome, or a human genome. The target genome is preferably pure or substantially pure, but this is not required. For example, an genomic sample from an animal source may include nucleic acid from contaminating or infecting organisms.

The nucleic acid sample can be, or can be derived from, for example, one or more whole genomes from the same or different organisms, tissues, cells or a combination; one or more partial genomes from the same or different organisms, tissues, cells or a combination; one or more whole chromosomes from the same or different organisms, tissues, cells or a combination; one or more partial chromosomes from the same or different organisms, tissues, cells or a combination; one or more chromosome fragments from the same or different organisms, tissues, cells or a combination; one or more artificial chromosomes; one or more yeast artificial chromosomes; one or more bacterial artificial chromosomes; one or more cosmids; or any combination of these.

Where the nucleic acid sample is a nucleic acid sample of high complexity, the nucleic acid molecules in the sample can be from any source or combination of sources that result in a highly complex sample. By high complexity or high sequence complexity is meant that the nucleic acid sample has a large number of unique (that is, non-repeated) sequences. The total number of nucleotides in the unique sequences is the sequence complexity of the nucleic acid sample. For example, the human genome has approximately $3 \times 10^9$ unique sequences and so has a sequence complexity of approximately $3 \times 10^9$ nucleotides. A nucleic acid sample of high sequence complexity has a sequence complexity of at least $1 \times 10^6$ nucleotides. Thus, a nucleic acid sample of high sequence complexity can have, for example, a sequence complexity of at least $1 \times 10^6$ nucleotides, a sequence complexity of at least $1 \times 10^7$ nucleotides, a sequence complexity of at least $1 \times 10^8$ nucleotides, or a sequence complexity of at least $1 \times 10^9$ nucleotides.

The nucleic acid sample can also be a nucleic acid sample of significant complexity. By significant complexity or significant sequence complexity is meant that the nucleic acid sample has a significant number of unique (that is, non-repeated) sequences. A nucleic acid sample of significant sequence complexity has a sequence complexity of at least $1 \times 10^5$ nucleotides. Thus, a nucleic acid sample of significant sequence complexity can have, for example, a sequence complexity of at least $1 \times 10^5$ nucleotides, a sequence complexity of at least $1 \times 10^6$ nucleotides, a sequence complexity of at least $1 \times 10^7$ nucleotides, a sequence complexity of at least $1 \times 10^8$ nucleotides, or a sequence complexity of at least $1 \times 10^9$ nucleotides. The nucleic acid sample can also be a nucleic acid sample of notable complexity. By notable complexity or notable sequence complexity is meant that the nucleic acid sample has a notable number of unique (that is, non-repeated) sequences. A nucleic acid sample of notable sequence complexity has a sequence complexity of at least $1 \times 10^4$ nucleotides. Thus, a nucleic acid sample of significant sequence complexity can have, for example, a sequence complexity of at least $1 \times 10^4$ nucleotides, a sequence complexity of at least $1 \times 10^5$ nucleotides, a sequence complexity of at least $1 \times 10^6$ nucleotides, a sequence complexity of at least $1 \times 10^7$ nucleotides, a sequence complexity of at least $1 \times 10^8$ nucleotides, or a sequence complexity of at least $1 \times 10^9$ nucleotides.

Nucleic acid samples and genomic nucleic acid samples can have, for example, a sequence complexity of at least $1 \times 10^3$ nucleotides, a sequence complexity of at least $1 \times 10^4$ nucleotides, a sequence complexity of at least $1 \times 10^5$ nucleotides, a sequence complexity of at least $1 \times 10^6$ nucleotides, a sequence complexity of at least $1 \times 10^7$ nucleotides, a sequence complexity of at least $1 \times 10^8$ nucleotides, or a sequence complexity of at least $1 \times 10^9$ nucleotides.

Samples can be used and manipulated in the disclosed methods. For example, a sample can be exposed to alkaline conditions or brought into contact or mixed with a lysis solution or denaturing solution. As used herein, the term sample refers both to source samples, samples used in the disclosed methods in whole, and to portions of source samples used in the disclosed methods. Thus, for example, a portion of a source sample that is exposed to alkaline conditions is considered to be a sample itself. All or a portion of a sample can be exposed to alkaline conditions or brought into contact or mixed with a lysis solution or denaturing solution. Similarly, the pH of all or a portion of a sample exposed to alkaline conditions or brought into contact or mixed with a lysis solution or denaturing solution can be reduced, or all or a portion of a sample exposed to alkaline conditions or brought into contact with a lysis solution or denaturing solution can be brought into contact or mixed with a stabilization solution. All or a portion of the resulting stabilized or neutralized sample can be incubated under conditions that promote replication of nucleic acids. An amplification mixture can comprise all or a portion of a stabilized or neutralized sample. An amplification mixture is the reaction solution where nucleic acids are amplified.

F. Lysis Solution

In the disclosed method, the cells can be exposed to alkaline conditions by mixing the cells with a lysis solution. A lysis solution is generally a solution that can raise the pH of a cell solution sufficiently to cause cell lysis. Denaturing solutions can be used as lysis solutions so long as the denaturing solution can have the effects required of lysis solutions. In some embodiments, the lysis solution can comprises a base, such as an aqueous base. Useful bases include potassium hydroxide, sodium hydroxide, potassium acetate, sodium acetate, ammonium hydroxide, lithium hydroxide, calcium hydroxide, magnesium hydroxide, sodium carbonate, sodium bicarbonate, calcium carbonate, ammonia, aniline, benzylamine, n-butylamine, diethylamine, dimethylamine, diphenylamine, ethylamine, ethylenediamine, methylamine, N-methylaniline, morpholine, pyridine, triethylamine, trimethylamine, aluminum hydroxide, rubidium hydroxide, cesium hydroxide, strontium hydroxide, barium hydroxide, and DBU (1,8-diazobicyclo[5,4,0]undec-7-ene). Useful formulations of lysis solution include lysis solution comprising 400 mM KOH, lysis solution comprising 400 mM KOH and 10 mM EDTA, lysis solution comprising 400 mM KOH, 100 mM dithiothreitol, and 10 mM EDTA, and lysis solution consisting of 400 mM KOH, 100 mM dithiothreitol, and 10 mM EDTA. Other useful formulations of lysis solution include lysis solution comprising 100 mM KOH, lysis solution comprising 100 mM KOH and 2.5 mM EDTA, lysis solution comprising 100 mM KOH, 25 mM dithiothreitol, and 2.5 mM EDTA, and lysis solution consisting of 100 mM KOH, 25 mM dithiothreitol, and 2.5 mM EDTA. Useful lysis solutions can have a pH of 8. Lysis solutions can be diluted prior to use. In such cases, the amount of lysis solution added to a reaction generally could be increased proportionally.

In some embodiments, the lysis solution can comprise a plurality of basic agents. As used herein, a basic agent is a compound, composition or solution that results in alkaline conditions. In some embodiments, the lysis solution can comprise a buffer. Useful buffers include phosphate buffers, "Good" buffers (such as BES, BICINE, CAPS, EPPS, HEPES, MES, MOPS, PIPES, TAPS, TES, and TRICINE), sodium cacodylate, sodium citrate, triethylammonium acetate, triethylammonium bicarbonate, Tris, Bis-tris, and Bis-tris propane. The lysis solution can comprise a plurality of buffering agents. As used herein, a buffering agent is a compound, composition or solution that acts as a buffer. An alkaline buffering agent is a buffering agent that results in alkaline conditions. In some embodiments, the lysis solution can comprise a combination of one or more bases, basic agents, buffers and buffering agents.

The amount of lysis solution mixed with the cells can be that amount that causes a substantial number of cells to lyse or those that cause a sufficient number of cells to lyse. Generally, this volume will be a function of the pH of the cell/lysis solution mixture. Thus, the amount of lysis solution to mix with cells can be determined generally from the volume of the cells and the alkaline concentration of the lysis buffer. For example, a smaller volume of a lysis solution with a stronger base and/or higher concentration of base would be needed to create sufficient alkaline conditions than the volume needed of a lysis solution with a weaker base and/or lower concentration of base. The lysis solution can be formulated such that the cells are mixed with an equal volume of the lysis solution (to produce the desired alkaline conditions).

For example, lysis solutions can be solutions that have a pH of from about 8.0 to about 13.0, from about 8.5 to about 13.0, from about 9.0 to about 13.0, from about 9.5 to about 13.0, from about 10.0 to about 13.0, from about 10.5 to about 13.0, from about 11.0 to about 13.0, from about 11.5 to about 13.0, from about 12.0 to about 13.0, from about 8.0 to about 12.0, from about 8.5 to about 12.0, from about 9.0 to about 12.0, from about 9.5 to about 12.0, from about 10.0 to about 12.0, from about 10.5 to about 12.0, from about 11.0 to about 12.0, from about 11.5 to about 12.0, from about 8.0 to about 11.5, from about 8.5 to about 11.5, from about 9.0 to about 11.5, from about 9.5 to about 11.5, from about 10.0 to about 11.5, from about 10.5 to about 11.5, from about 11.0 to about 11.5, from about 8.0 to about 11.0, from about 8.5 to about 11.0, from about 9.0 to about 11.0, from about 9.5 to about 11.0, from about 10.0 to about 11.0, from about 10.5 to about 11.0, from about 8.0 to about 10.5, from about 8.5 to about 10.5, from about 9.0 to about 10.5, from about 9.5 to about 10.5, from about 10.0 to about 10.5, from about 8.0 to about 10.0, from about 8.5 to about 10.0, from about 9.0 to about 10.0, from about 9.5 to about 10.0, from about 8.0 to about 9.5, from about 8.5 to about 9.5, from about 9.0 to about 9.5, about 8.0, about 8.5, about 9.0, about 9.5, about 10.0, about 10.5, about 11.0, about 11.5, about 12.0, about 12.5, or about 13.0.

Lysis solutions can have, for example, component concentrations of from about 10 mM to about 1 M, from about 10 mM to about 900 mM, from about 10 mM to about 800 mM, from about 10 mM to about 700 mM, from about 10 mM to about 600 mM, from about 10 mM to about 500 mM, from about 10 mM to about 400 mM, from about 10 mM to about 300 mM, from about 10 mM to about 200 mM, from about 10 mM to about 100 mM, from about 10 mM to about 90 mM, from about 10 mM to about 80 mM, from about 10 mM to about 70 mM, from about 10 mM to about 60 mM, from about 10 mM to about 50 mM, from about 10 mM to about 40 mM, from about 10 mM to about 30 mM, from about 10 mM to about 20 mM, from about 20 mM to about 1 M, from about 20 mM to about 900 mM, from about 20 mM to about 800 mM, from about 20 mM to about 700 mM, from about 20 mM to about 600 mM, from about 20 mM to about 500 mM, from about 20 mM to about 400 mM, from about 20 mM to about 300 mM, from about 20 mM to about 200 mM, from about 20 mM to about 100 mM, from about 20 mM to about 90 mM, from about 20 mM to about 80 mM, from about 20 mM to about 70 mM, from about 20 mM to about 60 mM, from about 20 mM to about 50 mM, from about 20 mM to about 40 mM, from about 20 mM to about 30 mM, from about 30 mM to about 1 M, from about 30 mM to about 900 mM, from about 30 mM to about 800 mM, from about 30 mM to about 700 mM, from about 30 mM to about 600 mM, from about 30 mM to about 500 mM, from about 30 mM to about 400 mM, from about 30 mM to about 300 mM, from about 30 mM to about 200 mM, from about 30 mM to about 100 mM, from about 30 mM to about 90 mM, from about 30 mM to about 80 mM, from about 30 mM to about 70 mM, from about 30 mM to about 60 mM, from about 30 mM to about 50 mM, from about 30 mM to about 40 mM, from about 40 mM to about 1 M, from about 40 mM to about 900 mM, from about 40 mM to about 800 mM, from about 40 mM to about 700 mM, from about 40 mM to about 600 mM, from about 40 mM to about 500 mM, from about 40 mM to about 400 mM, from about 40 mM to about 300 mM, from about 40 mM to about 200 mM, from about 40 mM to about 100 mM, from about 40 mM to about 90 mM, from about 40 mM to about 80 mM, from about 40 mM to about 70 mM, from about 40 mM to about 60 mM, from about 40 mM to about 50 mM, from about 50 mM to about 1 M, from about 50 mM to about 900 mM, from about 50 mM to about 800 mM, from about 50 mM to about 700 mM, from about 50 mM to about 600 mM, from about 50 mM to about 500 mM, from about 50 mM to about 400 mM, from about 50 mM to about 300 mM, from about 50 mM to about 200 mM, from about 50 mM to about 100 mM, from about 50 mM to about 90 mM, from about 50 mM to about 80 mM, from about 50 mM to about 70 mM, from about 50 mM to about 60 mM, from about 60 mM to about 1 M, from about 60 mM to about 900 mM, from about 60 mM to about 800 mM, from about 60 mM to about 700 mM, from about 60 mM to about 600 mM, from about 60 mM to about 500 mM, from about 60 mM to about 400 mM, from about 60 mM to about 300 mM, from about 60 mM to about 200 mM, from about 60 mM to about 100 mM, from about 60 mM to about 90 mM, from about 60 mM to about 80 mM, from about 60 mM to about 70 mM, from about 70 mM to about 1 M, from about 70 mM to about 900 mM, from about 70 mM to about 800 mM, from about 70 mM to about 700 mM, from about 70 mM to about 600 mM, from about 70 mM to about 500 mM, from about 70 mM to about 400 mM, from about 70 mM to about 300 mM, from about 70 mM to about 200 mM, from about 70 mM to about 100 mM, from about 70 mM to about 90 mM, from about 70 mM to about 80 mM, from about 80 mM to about 1 M, from about 80 mM to about 900 mM, from about 80 mM to about 800 mM, from about 80 mM to about 700 mM, from about 80 mM to about 600 mM, from about 80 mM to about 500 mM, from about 80 mM to about 400 mM, from about 80 mM to about 300 mM, from about 80 mM to about 200 mM, from about 80 mM to about 100 mM, from about 80 mM to about 90 mM, from about 90 mM to about 1 M, from about 90 mM to about 900 mM, from about 90 mM to about 800 mM, from about 90 mM to about 700 mM, from about 90 mM to about 600 mM, from about 90 mM to about 500 mM, from about 90 mM to about 400 mM, from about 90 mM to about 300 mM, from about 90 mM to about 200 mM, from about 90 mM to about 100 mM, from about 100 mM to about 1 M, from about 100 mM to about 900 mM, from about 100 mM to about 800 mM, from about 100 mM to about 700 mM, from about 100 mM to about 600 mM, from about 100 mM to about 500 mM, from about 100 mM to about 400 mM, from about 100 mM to about 300 mM, from about 100 mM to about 200 mM, from about 200 mM to about 1 M, from about 200 mM to about 900 mM, from about 200 mM to about 800 mM, from about 200 mM to about 700 mM, from about 200 mM to about 600 mM, from about 200 mM to about 500 mM, from about 200 mM to about 400 mM, from about 200 mM to about 300 mM, from about 300 mM to about 1 M, from about 300 mM to about 900 mM, from about 300 mM to about 800 mM, from about 300 mM to about 700 mM, from about 300 mM to about 600 mM, from about 300 mM to about 500 mM, from about 300 mM to about 400 mM, from about 400 mM to about 1 M, from about 400 mM to about 900 mM, from about 400 mM to about 800 mM, from about 400 mM to about 700 mM, from about 400 mM to about 600 mM, from about 400 mM to about 500 mM, from about 500 mM to about 1 M, from about 500 mM to about 900 mM, from about 500 mM to about 800 mM, from about 500 mM to about 700 mM, from about 500 mM to about 600 mM, from about 600 mM to about 1 M, from about 600 mM to about 900 mM, from about 600 mM to about 800 mM, from about 600 mM to about 700 mM, from about 700 mM to about 1 M, from about 700 mM to about 900 mM, from about 700 mM to about 800 mM, from about 800 mM to about 1 M, from about 800 mM to about 900 mM; from about 900 mM to about 1 M, about 10 mM, about 20 mM, about 30 mM, about 40 mM, about 50 mM, about 60 mM, about 70 mM, about 80 mM, about 90 mM, about 100 mM, about 200 mM, about 300 mM, about 400 mM, about 500 mM, about 600 mM, about 700 mM, about 800 mM, about 900 mM, or about 1 M.

Final concentrations of lysis solution components (after mixing with samples) can be, for example, from about 10 mM to about 1 M, from about 10 mM to about 900, mM, from about 10 mM to about 800 mM, from about 10 mM to about 700 mM, from about 10 mM to about 600 mM, from about 10 mM to about 500 mM, from about 10 mM to about 400 mM, from about 10 mM to about 300 mM, from about 10 mM to about 200 mM, from about 10 mM to about 100 mM, from about 10 mM to about 90 mM, from about 10 mM to about 80 mM, from about 10 mM to about 70 mM, from about 10 mM to about 60 mM, from about 10 mM to about 50 mM, from about 10 mM to about 40 mM, from about 10 mM to about 30 mM, from about 10 mM to about 20 mM, from about 20 mM to about 1 M, from about 20 mM to about 900 mM, from about 20 mM to about 800 mM, from about 20 mM to about 700 mM, from about 20 mM to about 600 mM, from about 20 mM to about 500 mM, from about 20 mM to about 400 mM, from about 20 mM to about 300 mM, from about 20 mM to about 200 mM, from about 20 mM to about 100 mM, from about 20 mM to about 90 mM, from about 20 mM to about 80 mM, from about 20 mM to about 70 mM, from about 20 mM to about 60 mM, from about 20 mM to about 50 mM, from about 20 mM to about 40 mM, from about 20 mM to about 30 mM, from about 30 mM to about 1 M, from about 30 mM to about 900 mM, from about 30 mM to about 800 mM, from about 30 mM to about 700 mM, from about 30 mM to about 600 mM, from about 30 mM to about 500 mM, from about 30 mM to about 400 mM, from about 30 mM to about 300 mM, from about 30 mM to about 200 mM, from about 30 mM to about 100 mM, from about 30 mM to about 90 mM, from about 30 mM to about 80 mM, from about 30 mM to about 70 mM, from about 30 mM to about 60 mM, from about 30 mM to about 50 mM, from about 30 mM to about 40 mM, from about 40 mM to about 1 M, from about 40 mM to about 900 mM, from about 40 mM to about 800 mM, from about 40 mM to about 700 mM, from about 40 mM to about 600 mM, from about 40 mM to about 500 mM, from about 40 mM to about 400 mM, from about 40 mM to about 300 mM, from about 40 mM to about 200 mM, from about 40 mM to about 100 mM, from about 40 mM to about 90 mM, from about 40 mM to about 80 mM, from about 40 mM to about 70 mM, from about 40 mM to about 60 mM, from about 40 mM to about 50 mM, from about 50 mM to about 1 M, from about 50 mM to about 900 mM, from about 50 mM to about 800 mM, from about 50 mM to about 700 mM, from about 50 mM to about 600 mM, from about 50 mM to about 500 mM, from about 50 mM to about 400 mM, from about 50 mM to about 300 mM, from about 50 mM to about 200 mM, from about 50 mM to about 100 mM, from about 50 mM to about 90 mM, from about 50 mM to about 80 mM, from about 50 mM to about 70 mM, from about 50 mM to about 60 mM, from about 60 mM to about 1 M, from about 60 mM to about 900 mM, from about 60 mM to about 800 mM, from about 60 mM to about 700 mM, from about 60 mM to about 600 mM, from about 60 mM to about 500 mM, from about 60 mM to about 400 mM, from about 60 mM to about 300 mM, from about 60 mM to about 200 mM, from about 60 mM to about 100 mM, from about 60 mM to about 90 mM, from about 60 mM to about 80 mM, from about 60 mM to about 70 mM, from about 70 mM to about 1 M, from about 70 mM to about 900 mM, from about 70 mM to about 800 mM, from about 70 mM to about 700 mM, from about 70 mM to about 600 mM, from about 70 mM to about 500 mM, from about 70 mM to about 400 mM, from about 70 mM to about 300 mM, from about 70 mM to about 200 mM, from about 70 mM to about 100 mM, from about 70 mM to about 90 mM, from about 70 mM to about 80 mM, from about 80 mM to about 1 M, from about 80 mM to about 900 mM, from about 80 mM to about 800 mM, from about 80 mM to about 700 mM, from about 80 mM to about 600 mM, from about 80 mM to about 500 mM, from about 80 mM to about 400 mM, from about 80 mM to about 300 mM, from about 80 mM to about 200 mM, from about 80 mM to about 100 mM, from about 80 mM to about 90 mM, from about 90 mM to about 1 M, from about 90 mM to about 900 mM, from about 90 mM to about 800 mM, from about 90 mM to about 700 mM, from about 90 mM to about 600 mM, from about 90 mM to about 500 mM, from about 90 mM to about 400 mM, from about 90 mM to about 300 mM, from about 90 mM to about 200 mM, from about 90 mM to about 100 mM, from about 100 mM to about 1 M, from about 100 mM to about 900 mM, from about 100 mM to about 800 mM, from about 100 mM to about 700 mM, from about 100 mM to about 600 mM, from about 100 mM to about 500 mM, from about 100 mM to about 400 mM, from about 100 mM to about 300 mM, from about 100 mM to about 200 mM, from about 200 mM to about 1 M, from about 200 mM to about 900 mM, from about 200 mM to about 800 mM, from about 200 mM to about 700 mM, from about 200 mM to about 600 mM, from about 200 mM to about 500 mM, from about 200 mM to about 400 mM, from about 200 mM to about 300 mM, from about 300 mM to about 1 M, from about 300 mM to about 900 mM, from about 300 mM to about 800 mM, from about 300 mM to about 700 mM, from about 300 mM to about 600 mM, from about 300 mM to about 500 mM, from about 300 mM to about 400 mM, from about 400 mM to about 1 M, from about 400 mM to about 900 mM, from about 400 mM to about 800 mM, from about 400 mM to about 700 mM, from about 400 mM to about 600 mM, from about 400 mM to about 500 mM, from about 500 mM to about 1 M, from about 500 mM to about 900 mM, from about 500 mM to about 800 mM, from about 500 mM to about 700 mM, from about 500 mM to about 600 mM, from about 600 mM to about 1 M, from about 600 mM to about 900 mM, from about 600 mM to about 800 mM, from about 600 mM to about 700 mM, from about 700 mM to about 1 M, from about 700 mM to about 900 mM, from about 700 mM to about 800 mM, from about 800 mM to about 1 M, from about 800 mM to about 900 mM, from about 900 mM to about 1 M, about 10 mM, about 20 mM, about 30 mM, about 40 mM, about 50 mM, about 60 mM, about 70 mM, about 80 mM, about 90 mM, about 100 mM, about 200 mM, about 300 mM, about 400 mM, about 500 mM, about 600 mM, about 700 mM, about 800 mM, about 900 mM, or about 1 M.

The lysis solution can be composed of multiple solutions and/or components that can be added to cells separately or combined in different combinations prior to addition to cells. Thus, for example, a solution of 400 mM KOH and 10 mM EDTA and a solution of 100 mM dithiothreitol can be added to the cells separately. Similarly, the disclosed kits can be composed of multiple solutions and/or components to be combined to form a lysis solution prior to addition to cells or for separate addition to cells. Stock lysis solutions can be diluted to form final lysis solutions for use in the disclosed method. Stock lysis solutions can have any concentration described herein for lysis solutions or any concentration that is more concentrated than any lysis solution or lysis solution concentration described herein. The final concentration of lysis solution components (after mixing with samples) can be any concentration described herein for lysis solutions. Useful final concentrations of lysis solution components can be 50 mM KOH, 12.5 mM dithiothreitol, and 1.25 mM EDTA.

G. Stabilization Solution

In the disclosed method, the pH of the cell lysate or sample can be reduced to form a stabilized or neutralized cell lysate or stabilized or neutralized sample. A stabilization solution is generally a solution that can reduce the pH of a cell lysate or sample exposed to alkaline conditions as described elsewhere herein. In some embodiments, the stabilization solution can comprise an acid. Useful acids include hydrochloric acid, sulfuric acid, phosphoric acid, acetic acid, acetylsalicylic acid, ascorbic acid, carbonic acid, citric acid, formic acid, nitric acid, perchloric acid, HF, HBr, HI, $H_2S$, HCN, HSCN, HClO, monochloroacetic acid, dichloroacetic acid, trichloroacetic acid, and any carboxylic acid (ethanoic, propanoic, butanoic, etc., including both linear or branched chain carboxylic acids). In some embodiments, the stabilization solution can comprise a buffer. Useful buffers include Tris-HCl, HEPES, "Good" buffers (such as BES, BICINE, CAPS, EPPS, HEPES, MES, MOPS, PIPES, TAPS, TES, and TRICINE), sodium cacodylate, sodium citrate, triethylammonium acetate, triethylammonium bicarbonate, Tris, Bis-tris, and Bis-tris propane. Useful formulations of stabilization solutions include stabilization solution comprising 800 mM Tris-HCl; stabilization solution comprising 800 mM Tris-HCl at pH 4.1, and stabilization solution consisting of 800 mM Tris-HCl, pH 4.1. Useful formulations of stabilization solutions include stabilization solution comprising 800 mM Tris-HCl at pH 4, and stabilization solution consisting of 800 mM Tris-HCl, pH 4. Other useful formulations of stabilization solutions include stabilization solution comprising 160 mM Tris-HCl; stabilization solution comprising 160 mM Tris-HCl at pH 4.1, and stabilization solution consisting of 160 mM Tris-HCl, pH 4.1. Other useful formulations of stabilization solutions include stabilization solution comprising 160 mM Tris-HCl; stabilization solution comprising 160 mM Tris-HCl at pH 4, and stabilization solution consisting of 160 mM Tris-HCl, pH 4. Stabilization solutions can be diluted prior to use. In such cases, the amount of stabilization solution added to a reaction generally could be increased proportionally.

In some embodiments, the stabilization solution can comprise a plurality of acidic agents. As used herein, an acidic agent is a compound, composition or solution that forms an acid in solution. In some embodiments, the stabilization solution can comprise a plurality of buffering agents. An acidic buffering agent is a buffering agent that forms an acid in solution. In some embodiments, the stabilization solution can comprise a combination of one or more acids, acidic agents, buffers and buffering agents.

A stabilized cell lysate or stabilized samples is a cell lysate or sample the pH of which is in the neutral range (from about pH 6.0 to about pH 9.0). Useful stabilized cell lysates and samples have a pH that allows replication of nucleic acids in the cell lysate. For example, the pH of the stabilized cell lysate or sample is usefully at a pH at which the DNA polymerase can function. The pH of the cell lysate or sample can be reduced by mixing the cell lysate or sample with a stabilization solution.

The amount of stabilization solution mixed with the cell lysate or sample can be that amount that causes a reduction in pH to the neutral range (or other desired pH value). Generally, this volume will be a function of the pH of the cell lysate/stabilization solution mixture or of the sample/stabilization solution mixture. Thus, the amount of stabilization solution to mix with the cell lysate or sample can be determined generally from the volume of the cell lysate or sample, its pH and buffering capacity, and the acidic concentration of the stabilization buffer. For example, a smaller volume of a stabilization solution with a stronger acid and/or higher concentration of acid would be needed to reduce the pH sufficiently than the volume needed of a stabilization solution with a weaker acid and/or lower concentration of acid. The stabilization solution can be formulated such that the cell lysate or sample is mixed with an equal volume of the stabilization solution (to produce the desired pH).

For example, stabilization solutions can be solutions that have a pH of from about 1.0 to about 6.0, from about 2.0 to about 6.0, from about 3.0 to about 6.0, from about 3.5 to about 6.0, from about 4.0 to about 6.0, from about 4.5 to about 6.0, from about 5.0 to about 6.0, from about 5.5 to about 6.0, from about 1.0 to about 5.5, from about 2.0 to about 5.5, from about 3.0 to about 5.5, from about 3.5 to about 5.5, from about 4.0 to about 5.5, from about 4.5 to about 5.5, from about 5.0 to about 5.5, from about 1.0 to about 5.0, from about 2.0 to about 5.0, from about 3.0 to about 5.0, from about 3.5 to about 5.0, from about 4.0 to about 5.0, from about 4.5 to about 5.0, from about 1.0 to about 4.5, from about 2.0 to about 4.5, from about 3.0 to about 4.5, from about 3.5 to about 4.5, from about 4.0 to about 4.5, from about 1.0 to about 4.0, from about 2.0 to about 4.0, from about 3.0 to about 4.0, from about 3.5 to about 4.0, from about 1.0 to about 3.5, from about 2.0 to about 3.5, from about 3.0 to about 3.5, from about 1.0 to about 3.0, from about 2.0 to about 3.0, from about 1.0 to about 2.5, from about 2.0 to about 2.5, from about 1.0 to about 2.0, about 1.0, about 2.0, about 2.5, about 3.0, about 3.5, about 4.0, about 4.5, about 5.0, about 5.5, or about 6.0.

Stabilization solutions can have, for example, component concentrations of from about 100 mM to about 1 M, from about 100 mM to about 900 mM, from about 100 mM to about 800 mM, from about 100 mM to about 700 mM, from about 100 mM to about 600 mM, from about 100 mM to about 500 mM, from about 100 mM to about 400 mM, from about 100 mM to about 300 mM, from about 100 mM to about 200 mM, from about 200 mM to about 1 M, from about 200 mM to about 900 mM, from about 200 mM to about 800 mM, from about 200 mM to about 700 mM, from about 200 mM to about 600 mM, from about 200 mM to about 500 mM, from about 200 mM to about 400 mM, from about 200 mM to about 300 mM, from about 300 mM to about 1 M, from about 300 mM to about 900 mM, from about 300 mM to about 800 mM, from about 300 mM to about 700 mM, from about 300 mM to about 600 mM, from about 300 mM to about 500 mM, from about 300 mM to about 400 mM, from about 400 mM to about 1 M, from about 400 mM to about 900 mM, from about 400 mM to about 800 mM, from about 400 mM to about 700 mM, from about 400 mM to about 600 mM, from about 400 mM to about 500 mM, from about 500 mM to about 1 M, from about 500 mM to about 900 mM, from about 500 mM to about 800 mM, from about 500 mM to about 700 mM, from about 500 mM to about 600 mM, from about 600 mM to about 1 M, from about 600 mM to about 900 mM, from about 600 mM to about 800 mM, from about 600 mM to about 700 mM, from about 700 mM to about 1 M, from about 700 mM to about 900 mM, from about 700 mM to about 800 mM, from about 800 mM to about 1 M, from about 800 mM to about 900 mM, from about 900 mM to about 1 M, about 100 mM, about 200 mM, about 300 mM, about 400 mM, about 500 mM, about 600 mM, about 700 mM, about 800 mM, about 900 mM, or about 1 M.

Final concentrations of stabilization solution components can be, for example, from about 100 mM to about 1 M, from about 100 mM to about 900 mM, from about 100 mM to about 800 mM, from about 100 mM to about 700 mM, from about 100 mM to about 600 mM, from about 100 mM to about 500 mM, from about 100 mM to about 400 mM, from about 100 mM to about 300 mM, from about 100 mM to about 200 mM, from about 200 mM to about 1 M, from about 200 mM to about 900 mM, from about 200 mM to about 800 mM, from about 200 mM to about 700 mM, from about 200 mM to about 600 mM, from about 200 mM to about 500 mM, from about 200 mM to about 400 mM, from about 200 mM to about 300 mM, from about 300 mM to about 1 M, from about 300 mM to about 900 mM, from about 300 mM to about 800 mM, from about 300 mM to about 700 mM, from about 300 mM to about 600 mM, from about 300 mM to about 500 mM, from about 300 mM to about 400 mM, from about 400 mM to about 1 M, from about 400 mM to about 900 mM, from about 400 mM to about 800 mM, from about 400 mM to about 700 mM, from about 400 mM to about 600 mM, from about 400 mM to about 500 mM, from about 500 mM to about 1 M, from about 500 mM to about 900 mM, from about 500 mM to about 800 mM, from about 500 mM to about 700 mM, from about 500 mM to about 600 mM, from about 600 mM to about 1 M, from about 600 mM to about 900 mM, from about 600 mM to about 800 mM, from about 600 mM to about 700 mM, from about 700 mM to about 1 M, from about 700 mM to about 900 mM, from about 700 mM to about 800 mM, from about 800 mM to about 1 M, from about 800 mM to about 900 mM, from about 900 mM to about 1 M, about 100 mM, about 200 mM, about 300 mM, about 400 mM, about 500 mM, about 600 mM, about 700 mM, about 800 mM, about 900 mM, or about 1 M.

The stabilization solution can be composed of multiple solutions and/or components that can be added to cell lysates and samples separately or combined in different combinations prior to addition to cell lysates and samples. Thus, for example, a solution of a buffer and a solution of an acid can be added to the cells separately. Similarly, the disclosed kits can be composed of multiple solutions and/or components to be combined to form a stabilization solution prior to addition to cell lysates or samples or for separate addition to cell lysates or samples. Stock stablization solutions can be diluted to form final stabilization solutions for use in the disclosed method. Stock stabilization solutions can have any concentration described herein for stabilization solutions or any concentration that is more concentrated than any stabilization solution or stabilization solution concentration described herein. The final concentration of stabilization solution components (after mixing with samples) can be any concentration described herein for stabilization solutions. Useful final concentrations of lysis solution components can be 80 mM Tris-HCl.

As used herein, a neutralization solution is a form of stabilization solution. Reference to neutralized cell lysates, neutralized sample, and other neutralized components or solutions is considered the equivalent of a stabilized cell lysate, stabilized sample, or other stabilized component or solution.

H. Denaturing Solution

In some forms of the disclosed method, the DNA samples can be exposed to denaturing conditions by mixing the sample with a denaturing solution. A denaturing solution is generally a solution that can raise the pH of a sample sufficiently to cause, in combination with other conditions such as heating, substantial denaturation of DNA in the DNA sample. Substantial denaturation refers to denaturation of 90% or more of the nucleotides in 90% or more of the DNA molecules in a sample. In this context, denaturation of nucleotides refers to unpaired nucleotides whether physically denatured by treatment or already unpaired in the sample. Lysis solutions can be used as denaturing solutions so long as the lysis solution has the effects required of denaturing solutions.

In some embodiments, the denaturing solution can comprises a base, such as an aqueous base. Useful bases include potassium hydroxide, sodium hydroxide, potassium acetate, sodium acetate, ammonium hydroxide, lithium hydroxide, calcium hydroxide, magnesium hydroxide, sodium carbonate, sodium bicarbonate, calcium carbonate, ammonia, aniline, benzylamine, n-butylamine, diethylamine, dimethylamine, diphenylamine, ethylamine, ethylenediamine, methylamine, N-methylaniline, morpholine, pyridine, triethylamine, trimethylamine, aluminum hydroxide, rubidium hydroxide, cesium hydroxide, strontium hydroxide, barium hydroxide, and DBU (1,8-diazobicyclo[5,4,0]undec-7-ene). Useful formulations of denaturing solution include denaturing solution comprising about 150 mM to about 500 mM NaOH, denaturing solution comprising about 150 mM to about 500 mM NaOH, and denaturing solution consisting of about 150 mM to about 500 mM NaOH. Denaturing solutions can be diluted prior to use. In such cases, the amount of denaturing solution added to a reaction generally could be increased proportionally.

In some embodiments, the denaturing solution can comprise a plurality of basic agents. As used herein, a basic agent is a compound, composition or solution that results in denaturing conditions. In some embodiments, the denaturing solution can comprise a buffer. Useful buffers include phosphate buffers, "Good" buffers (such as BES, BICINE, CAPS, EPPS, HEPES, MES, MOPS, PIPES, TAPS, TES, and TRICINE), sodium cacodylate, sodium citrate, triethylammonium acetate, triethylammonium bicarbonate, Tris, Bis-tris, and Bis-tris propane. The denaturing solution can comprise a plurality of buffering agents. As used herein, a buffering agent is a compound, composition or solution that acts as a buffer. An alkaline buffering agent is a buffering agent that results in alkaline conditions. In some embodiments, the denaturing solution can comprise a combination of one or more bases, basic agents, buffers and buffering agents.

The amount of denaturing solution mixed with the DNA samples can be that amount that causes, in combination with other conditions such as heating, substantial denaturation of DNA in the DNA sample. Generally, this volume will be a function of the pH, ionic strength, and temperature of the sample/denaturing solution mixture. Thus, the amount of denaturing solution to mix with DNA samples can be determined generally from the volume of the DNA sample, the alkaline concentration of the denaturing buffer, and the temperature to which the resulting mixture will be heated. For example, at a given temperature, a smaller volume of a denaturing solution with a stronger base and/or higher concentration of base would be needed to create sufficient denaturing conditions than the volume needed of a denaturing solution with a weaker base and/or lower concentration of base. The denaturing solution can be formulated such that the DNA samples are mixed with, for example, one tenth volume of the denaturing solution (to produce the desired denaturing conditions).

For example, denaturing solutions can be solutions that have a pH of from about 9.0 to about 13.0, from about 9.5 to about 13.0, from about 10.0 to about 13.0, from about 10.5 to about 13.0, from about 11.0 to about 13.0, from about 11.5 to about 13.0, from about 12.0 to about 13.0, from about 9.0 to about 12.0, from about 9.5 to about 12.0, from about 10.0 to about 12.0, from about 10.5 to about 12.0, from about 11.0 to about 12.0, from about 11.5 to about 12.0, from about 9.0 to about 11.5, from about 9.5 to about 11.5, from about 10.0 to about 11.5, from about 10.5 to about 11.5, from about 11.0 to about 11.5, from about 9.0 to about 11.0, from about 9.5 to about 11.0, from about 10.0 to about 11.0, from about 10.5 to about 11.0, from about 9.0 to about 10.5, from about 9.5 to about 10.5, from about 10.0 to about 10.5, from about 9.0 to about 10.0, from about 9.5 to about 10.0, from about 9.0 to about 9.5, about 9.0, about 9.5, about 10.0, about 10.5, about 11.0, about 11.5, about 12.0, about 12.5, or about 13.0.

Denaturing solutions can have, for example, component concentrations of from about 10 mM to about 1 M, from about 10 mM to about 900 mM, from about 10 mM to about 800 mM, from about 10 mM to about 700 mM, from about 10 mM to about 600 mM, from about 10 mM to about 500 mM, from about 10 mM to about 400 mM, from about 10 mM to about 300 mM, from about 10 mM to about 200 mM, from about 10 mM to about 100 mM, from about 10 mM to about 90 mM, from about 10 mM to about 80 mM, from about 10 mM to about 70 mM, from about 10 mM to about 60 mM, from about 10 mM to about 50 mM, from about 10 mM to about 40 mM, from about 10 mM to about 30 mM, from about 10 mM to about 20 mM, from about 20 mM to about 1 M, from about 20 mM to about 900 mM, from about 20 mM to about 800 mM, from about 20 mM to about 700 mM, from about 20 mM to about 600 mM, from about 20 mM to about 500 mM, from about 20 mM to about 400 mM, from about 20 mM to about 300 mM, from about 20 mM to about 200 mM, from about 20 mM to about 100 mM, from about 20 mM to about 90 mM, from about 20 mM to about 80 mM, from about 20 mM to about 70 mM, from about 20 mM to about 60 mM, from about 20 mM to about 50 mM, from about 20 mM to about 40 mM, from about 20 mM to about 30 mM, from about 30 mM to about 1 M, from about 30 mM to about 900 mM, from about 30 mM to about 800 mM, from about 30 mM to about 700 mM, from about 30 mM to about 600 mM, from about 30 mM to about 500 mM, from about 30 mM to about 400 mM, from about 30 mM to about 300 mM, from about 30 mM to about 200 mM, from about 30 mM to about 100 mM, from about 30 mM to about 90 mM, from about 30 mM to about 80 mM, from about 30 mM to about 70 mM, from about 30 mM to about 60 mM, from about 30 mM to about 50 mM, from about 30 mM to about 40 mM, from about 40 mM to about 1 M, from about 40 mM to about 900 mM, from about 40 mM to about 800 mM, from about 40 mM to about 700 mM, from about 40 mM to about 600 mM, from about 40 mM to about 500 mM, from about 40 mM to about 400 mM, from about 40 mM to about 300 mM, from about 40 mM to about 200 mM, from about 40 mM to about 100 mM, from about 40 mM to about 90 mM, from about 40 mM to about 80 mM, from about 40 mM to about 70 mM, from about 40 mM to about 60 mM, from about 40 mM to about 50 mM, from about 50 mM to about 1 M, from about 50 mM to about 900 mM, from about 50 mM to about 800 mM, from about 50 mM to about 700 mM, from about 50 mM to about 600 mM, from about 50 mM to about 500 mM, from about 50 mM to about 400 mM, from about 50 mM to about 300 mM, from about 50 mM to about 200 mM, from about 50 mM to about 100 mM, from about 50 mM to about 90 mM, from about 50 mM to about 80 mM, from about 50 mM to about 70 mM, from about 50 mM to about 60 mM, from about 60 mM to about 1 M, from about 60 mM to about 900 mM, from about 60 mM to about 800 mM, from about 60 mM to about 700 mM, from about 60 mM to about 600 mM, from about 60 mM to about 500 mM, from about 60 mM to about 400 mM, from about 60 mM to about 300 mM, from about 60 mM to about 200 mM, from about 60 mM to about 100 mM, from about 60 mM to about 90 mM, from about 60 mM to about 80 mM, from about 60 mM to about 70 mM, from about 70 mM to about 1 M, from about 70 mM to about 900 mM, from about 70 mM to about 800 mM, from about 70 mM to about 700 mM, from about 70 mM to about 600 mM, from about 70 mM to about 500 mM, from about 70 mM to about 400 mM, from about 70 mM to about 300 mM, from about 70 mM to about 200 mM, from about 70 mM to about 100 mM, from about 70 mM to about 90 mM, from about 70 mM to about 80 mM, from about 80 mM to about 1 M, from about 80 mM to about 900 mM, from about 80 mM to about 800 mM, from about 80 mM to about 700 mM, from about 80 mM to about 600 mM, from about 80 mM to about 500 mM, from about 80 mM to about 400 mM, from about 80 mM to about 300 mM, from about 80 mM to about 200 mM, from about 80 mM to about 100 mM, from about 80 mM to about 90 mM, from about 90 mM to about 1 M, from about 90 mM to about 900 mM, from about 90 mM to about 800 mM, from about 90 mM to about 700 mM, from about 90 mM to about 600 mM, from about 90 mM to about 500 mM, from about 90 mM to about 400 mM, from about 90 mM to about 300 mM, from about 90 mM to about 200 mM, from about 90 mM to about 100 mM, from about 100 mM to about 1 M, from about 100 mM to about 900 mM, from about 100 mM to about 800 mM, from about 100 mM to about 700 mM, from about 100 mM to about 600 mM, from about 100 mM to about 500 mM, from about 100 mM to about 400 mM, from about 100 mM to about 300 mM, from about 100 mM to about 200 mM, from about 200 mM to about 1 M, from about 200 mM to about 900 mM, from about 200 mM to about 800 mM, from about 200 mM to about 700 mM, from about 200 mM to about 600 mM, from about 200 mM to about 500 mM, from about 200 mM to about 400 mM, from about 200 mM to about 300 mM, from about 300 mM to about 1 M, from about 300 mM to about 900 mM, from about 300 mM to about 800 mM, from about 300 mM to about 700 mM, from about 300 mM to about 600 mM, from about 300 mM to about 500 mM, from about 300 mM to about 400 mM, from about 400 mM to about 1 M, from about 400 mM to about 900 mM, from about 400 mM to about 800 mM, from about 400 mM to about 700 mM, from about 400 mM to about 600 mM, from about 400 mM to about 500 mM, from about 500 mM to about 1 M, from about 500 mM to about 900 mM, from about 500 mM to about 800 mM, from about 500 mM to about 700 mM, from about 500 mM to about 600 mM, from about 600 mM to about 1 M, from about 600 mM to about 900 mM, from about 600 mM to about 800 mM, from about 600 mM to about 700 mM, from about 700 mM to about 1 M, from about 700 mM to about 900 mM, from about 700 mM to about 800 mM, from about 800 mM to about 1 M, from about 800 mM to about 900 mM, from about 900 mM to about 1 M, about 10 mM, about 20 mM, about 30 mM, about 40 mM, about 50 mM, about 60 mM, about 70 mM, about 80 mM, about 90 mM, about 100 mM, about 200 mM, about 300 mM, about 400 mM, about 500 mM, about 600 mM, about 700 mM, about 800 mM, about 900 mM, or about 1 M.

The denaturing solution can be composed of multiple solutions and/or components that can be added to DNA samples separately or combined in different combinations prior to addition to DNA samples. Thus, for example, a solution of a buffer and a solution of a base can be added to the samples separately. Similarly, the disclosed kits can be composed of multiple solutions and/or components to be combined to form a denaturing solution prior to addition to DNA samples or for separate addition to samples. Stock denaturing solutions can be diluted to form final denaturing solutions for use in the disclosed method. Stock denaturing solutions can have any concentration described herein for denaturing solutions or any concentration that is more concentrated than any denaturing solution or denaturing solution concentration described herein. The final concentration of denaturing solution components (after mixing with samples) can be any concentration described herein for denaturing solutions.

I. Nucleic Acid Fingerprints

The disclosed method can be used to produce replicated strands that serve as a nucleic acid fingerprint of a complex sample of nucleic acid. Such a nucleic acid fingerprint can be compared with other, similarly prepared nucleic acid fingerprints of other nucleic acid samples to allow convenient detection of differences between the samples. The nucleic acid fingerprints can be used both for detection of related nucleic acid samples and comparison of nucleic acid samples. For example, the presence or identity of specific organisms can be detected by producing a nucleic acid fingerprint of the test organism and comparing the resulting nucleic acid fingerprint with reference nucleic acid fingerprints prepared from known organisms. Changes and differences in gene expression patterns can also be detected by preparing nucleic acid fingerprints of mRNA from different cell samples and comparing the nucleic acid fingerprints. The replicated strands can also be used to produce a set of probes or primers that is specific for the source of a nucleic acid sample. The replicated strands can also be used as a library of nucleic acid sequences present in a sample. Nucleic acid fingerprints can be made up of, or derived from, whole genome amplification of a sample such that the entire relevant nucleic acid content of the sample is substantially represented, or from multiple strand displacement amplification of selected target sequences within a sample.

Nucleic acid fingerprints can be stored or archived for later use. For example, replicated strands produced in the disclosed method can be physically stored, either in solution, frozen, or attached or adhered to a solid-state substrate such as an array. Storage in an array is useful for providing an archived probe set derived from the nucleic acids in any sample of interest. As another example, informational content of, or derived from, nucleic acid fingerprints can also be stored. Such information can be stored, for example, in or as computer readable media. Examples of informational content of nucleic acid fingerprints include nucleic acid sequence information (complete or partial); differential nucleic acid sequence information such as sequences present in one sample but not another; hybridization patterns of replicated strands to, for example, nucleic acid arrays, sets, chips, or other replicated strands. Numerous other data that is or can be derived from nucleic acid fingerprints and replicated strands produced in the disclosed method can also be collected, used, saved, stored, and/or archived.

Nucleic acid fingerprints can also contain or be made up of other information derived from the information generated in the disclosed method, and can be combined with information obtained or generated from any other source. The informational nature of nucleic acid fingerprints produced using the disclosed method lends itself to combination and/or analysis using known bioinformatics systems and methods.

Nucleic acid fingerprints of nucleic acid samples can be compared to a similar nucleic acid fingerprint derived from any other sample to detect similarities and differences in the samples (which is indicative of similarities and differences in the nucleic acids in the samples). For example, a nucleic acid fingerprint of a first nucleic acid sample can be compared to a nucleic acid fingerprint of a sample from the same type of organism as the first nucleic acid sample, a sample from the same type of tissue as the first nucleic acid sample, a sample from the same organism as the first nucleic acid sample, a sample obtained from the same source but at time different from that of the first nucleic acid sample, a sample from an organism different from that of the first nucleic acid sample, a sample from a type of tissue different from that of the first nucleic acid sample, a sample from a strain of organism different from that of the first nucleic acid sample, a sample from a species of organism different from that of the first nucleic acid sample, or a sample from a type of organism different from that of the first nucleic acid sample.

The same type of tissue is tissue of the same type such as liver tissue, muscle tissue, or skin (which may be from the same or a different organism or type of organism). The same organism refers to the same individual, animal, or cell. For example, two samples taken from a patient are from the same organism. The same source is similar but broader, referring to samples from, for example, the same organism, the same tissue from the same organism, the same DNA molecule, or the same DNA library. Samples from the same source that are to be compared can be collected at different times (thus allowing for potential changes over time to be detected). This is especially useful when the effect of a treatment or change in condition is to be assessed. Samples from the same source that have undergone different treatments can also be collected and compared using the disclosed method. A different organism refers to a different individual organism, such as a different patient, a different individual animal. Different organism includes a different organism of the same type or organisms of different types. A different type of organism refers to organisms of different types such as a dog and cat, a human and a mouse, or *E. coli* and *Salmonella*. A different type of tissue refers to tissues of different types such as liver and kidney, or skin and brain. A different strain or species of organism refers to organisms differing in their species or strain designation as those terms are understood in the art.

J. Detection Labels

To aid in detection and quantitation of nucleic acids amplified using the disclosed method, detection labels can be directly incorporated into amplified nucleic acids or can be coupled to detection molecules. As used herein, a detection label is any molecule that can be associated with amplified nucleic acid, directly or indirectly, and which results in a measurable, detectable signal, either directly or indirectly. Many such labels for incorporation into nucleic acids or coupling to nucleic acid probes are known to those of skill in the art. Examples of detection labels suitable for use in the disclosed method are radioactive isotopes, fluorescent molecules, phosphorescent molecules, enzymes, antibodies, and ligands.

Examples of suitable fluorescent labels include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrrometheneboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Preferred fluorescent labels are fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1, 4-hexachlorofluorescein (HEX), 2',7'-dimethoxy-4',5'-dichloro-6-carboxyrhodamine (JOE), 2'-chloro-5'-fluoro-7, 8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio.

Additional labels of interest include those that provide for signal only when the probe with which they are associated is specifically bound to a target molecule, where such labels include: "molecular beacons" as described in Tyagi & Kramer, Nature Biotechnology (1996) 14:303 and EP 0 070 685 B1. Other labels of interest include those described in U.S. Pat. No. 5,563,037; WO 97/17471 and WO 97/17076.

Labeled nucleotides are a preferred form of detection label since they can be directly incorporated into the amplification products during synthesis. Examples of detection labels that can be incorporated into amplified nucleic acids include nucleotide analogs such as BrdUrd (5-bromodeoxyuridine, Hoy and Schimke, *Mutation Research* 290:217-230 (1993)), aminoallyldeoxyuridine (Henegariu et al., *Nature Biotechnology* 18:345-348 (2000)), 5-methylcytosine (Sano et al., *Biochim. Biophys. Acta* 951:157-165 (1988)), bromouridine (Wansick et al., *J. Cell Biology* 122:283-293 (1993)) and nucleotides modified with biotin (Langer et al., *Proc. Natl. Acad. Sci. USA* 78:6633 (1981)) or with suitable haptens such as digoxygenin (Kerkhof, *Anal. Biochem.* 205:359-364 (1992)). Suitable fluorescence-labeled nucleotides are Fluorescein-isothiocyanate-dUTP, Cyanine-3-dUTP and Cyanine-5-dUTP (Yu et al., *Nucleic Acids Res.*, 22:3226-3232 (1994)). A preferred nucleotide analog detection label for DNA is BrdUrd (bromodeoxyuridine, BrdUrd, BrdU, BUdR, Sigma-Aldrich Co). Other preferred nucleotide analogs for incorporation of detection label into DNA are AA-dUTP (aminoallyl-deoxyuridine triphosphate, Sigma-Aldrich Co.), and 5-methyl-dCTP (Roche Molecular Biochemicals). A preferred nucleotide analog for incorporation of detection label into RNA is biotin-16-UTP (biotin-16-uridine-5'-triphosphate, Roche Molecular Biochemicals). Fluorescein, Cy3, and Cy5 can be linked to dUTP for direct labelling. Cy3.5 and Cy7 are available as avidin or anti-digoxygenin conjugates for secondary detection of biotin- or digoxygenin-labelled probes.

Detection labels that are incorporated into amplified nucleic acid, such as biotin, can be subsequently detected using sensitive methods well-known in the art. For example, biotin can be detected using streptavidin-alkaline phosphatase conjugate (Tropix, Inc.), which is bound to the biotin and subsequently detected by chemiluminescence of suitable substrates (for example, chemiluminescent substrate CSPD: disodium, 3-(4-methoxyspiro-[1,2,-dioxetane-3-2'-(5'-chloro)tricyclo[3.3.1.1$^{3,7}$]decane]-4-yl) phenyl phosphate; Tropix, Inc.). Labels can also be enzymes, such as alkaline phosphatase, soybean peroxidase, horseradish peroxidase and polymerases, that can be detected, for example, with chemical signal amplification or by using a substrate to the enzyme which produces light (for example, a chemiluminescent 1,2-dioxetane substrate) or fluorescent signal.

Molecules that combine two or more of these detection labels are also considered detection labels. Any of the known detection labels can be used with the disclosed probes, tags, and method to label and detect nucleic acid amplified using the disclosed method. Methods for detecting and measuring signals generated by detection labels are also known to those of skill in the art. For example, radioactive isotopes can be detected by scintillation counting or direct visualization; fluorescent molecules can be detected with fluorescent spectrophotometers; phosphorescent molecules can be detected with a spectrophotometer or directly visualized with a camera; enzymes can be detected by detection or visualization of the product of a reaction catalyzed by the enzyme; antibodies can be detected by detecting a secondary detection label coupled to the antibody. As used herein, detection molecules are molecules which interact with amplified nucleic acid and to which one or more detection labels are coupled.

K. Detection Probes

Detection probes are labeled oligonucleotides having sequence complementary to detection tags on amplified nucleic acids. The complementary portion of a detection probe can be any length that supports specific and stable hybridization between the detection probe and the detection tag. For this purpose, a length of 10 to 35 nucleotides is preferred, with a complementary portion of a detection probe 16 to 20 nucleotides long being most preferred. Detection probes can contain any of the detection labels described above. Preferred labels are biotin and fluorescent molecules. A particularly preferred detection probe is a molecular beacon. Molecular beacons are detection probes labeled with fluorescent moieties where the fluorescent moieties fluoresce only when the detection probe is hybridized (Tyagi and Kramer, *Nature Biotechnol.* 14:303-309 (1995)). The use of such probes eliminates the need for removal of unhybridized probes prior to label detection because the unhybridized detection probes will not produce a signal. This is especially useful in multiplex assays.

L. Address Probes

An address probe is an oligonucleotide having a sequence complementary to address tags on primers. The complementary portion of an address probe can be any length that supports specific and stable hybridization between the address probe and the address tag. For this purpose, a length of 10 to 35 nucleotides is preferred, with a complementary portion of an address probe 12 to 18 nucleotides long being most preferred. An address probe can contain a single complementary portion or multiple complementary portions. Preferably, address probes are coupled, either directly or via a spacer molecule, to a solid-state support. Such a combination of address probe and solid-state support are a preferred form of solid-state detector.

M. Oligonucleotide Synthesis

Primers, detection probes, address probes, and any other oligonucleotides can be synthesized using established oligonucleotide synthesis methods. Methods to produce or synthesize oligonucleotides are well known in the art. Such methods can range from standard enzymatic digestion followed by nucleotide fragment isolation (see for example, Sambrook et al., *Molecular Cloning: A Laboratory Manual,* 2nd Edition (Cold Spring Harbor Laboratory Press, Cold Spring Harbor, N.Y., 1989) Chapters 5, 6) to purely synthetic methods, for example, by the cyanoethyl phosphoramidite method. Solid phase chemical synthesis of DNA fragments is routinely performed using protected nucleoside cyanoethyl phosphoramidites (S. L. Beaucage et al. (1981) Tetrahedron Lett. 22:1859). In this approach, the 3'-hydroxyl group of an initial 5'-protected nucleoside is first covalently attached to the polymer support (R. C. Pless et al. (1975) Nucleic Acids Res. 2:773 (1975)). Synthesis of the oligonucleotide then proceeds by deprotection of the 5'-hydroxyl group of the attached nucleoside, followed by coupling of an incoming nucleoside-3'-phosphoramidite to the deprotected hydroxyl group (M. D. Matteucci et al. (1981) J. Am. Chem. Soc. 103:3185). The resulting phosphite triester is finally oxidized to a phosphorotriester to complete the internucleotide bond (R. L. Letsinger et al. (1976) J. Am. Chem. Soc. 9:3655). Alternatively, the synthesis of phosphorothioate linkages can be carried out by sulfurization of the phosphite triester. Several chemicals can be used to perform this reaction, among them 3H-1,2-benzodithiole-3-one, 1,1-dioxide (R. P. Iyer, W. Egan, J. B. Regan, and S. L. Beaucage, J. Am. Chem. Soc., 1990, 112, 1253-1254). The steps of deprotection, coupling and oxidation are repeated until an oligonucleotide of the desired length and sequence is obtained. Other methods exist to generate oligonucleotides such as the H-phosphonate method (Hall et al, (1957) J. Chem. Soc., 3291-3296) or the phosphotriester method as described by Ikuta et al., *Ann. Rev. Biochem.* 53:323-356 (1984), (phosphotriester and phosphite-triester methods), and Narang et al., *Methods Enzymol.,* 65:610-620 (1980), (phosphotriester method). Protein nucleic acid molecules can be made using known methods such as those described by Nielsen et al., *Bioconjug. Chem.* 5:3-7 (1994). Other forms of oligonucleotide synthesis are described in U.S. Pat. No. 6,294,664 and U.S. Pat. No. 6,291, 669.

The nucleotide sequence of an oligonucleotide is generally determined by the sequential order in which subunits of subunit blocks are added to the oligonucleotide chain during synthesis. Each round of addition can involve a different, specific nucleotide precursor, or a mixture of one or more different nucleotide precursors. In general, degenerate or random positions in an oligonucleotide can be produced by using a mixture of nucleotide precursors representing the range of nucleotides that can be present at that position. Thus, precursors for A and T can be included in the reaction for a particular position in an oligonucleotide if that position is to be degenerate for A and T. Precursors for all four nucleotides can be included for a fully degenerate or random position. Completely random oligonucleotides can be made by including all four nucleotide precursors in every round of synthesis. Degenerate oligonucleotides can also be made having different proportions of different nucleotides. Such oligonucleotides can be made, for example, by using different nucleotide precursors, in the desired proportions, in the reaction.

Many of the oligonucleotides described herein are designed to be complementary to certain portions of other oligonucleotides or nucleic acids such that stable hybrids can be formed between them. The stability of these hybrids can be calculated using known methods such as those described in Lesnick and Freier, *Biochemistry* 34:10807-10815 (1995), McGraw et al., *Biotechniques* 8:674-678 (1990), and Rychlik et al., *Nucleic Acids Res.* 18:6409-6412 (1990).

Hexamer oligonucleotides were synthesized on a Perseptive Biosystems 8909 Expedite Nucleic Acid Synthesis system using standard β-cyanoethyl phosphoramidite coupling chemistry on mixed dA+dC+dG+dT synthesis columns (Glen Research, Sterling, Va.). The four phosphoramidites were mixed in equal proportions to randomize the bases at each position in the oligonucleotide. Oxidation of the newly formed phosphites were carried out using the sulfurizing reagent 3H-1,2-benzothiole-3-one-1,1-idoxide (Glen Research) instead of the standard oxidizing reagent after the first and second phosphoramidite addition steps. The thiophosphitylated oligonucleotides were deprotected using 30% ammonium hydroxide (3.0 ml) in water at 55° C. for 16 hours, concentrated in an OP 120 Savant Oligo Prep deprotection unit for 2 hours, and desalted with PD10 Sephadex columns using the protocol provided by the manufacturer.

N. Kits

The materials described above can be packaged together in any suitable combination as a kit useful for performing the disclosed method. Kit components in a given kit can be designed and adapted for use together in the disclosed method. For example, disclosed are kits for amplifying nucleic acids a thermolabile nucleic acid polymerase having strand displacement activity, an additive, and a set of primers. Incubating nucleic acids comprising target sequences at an elevated temperature in the presence of the thermolabile nucleic acid polymerase, the additive, and the set of primers under conditions promoting replication of the nucleic acids results in replicated strands and in formation of replicated strands from the target sequences in favor of formation of replicated strands from non-target sequences.

The nucleic acid polymerase can be Phi29 DNA polymerase. The additive can be a sugar, a chaperone, a protein, trehalose, glucose, sucrose, or a combination. The additive can comprise trehalose, the set of primers can comprise exonuclease-resistant random hexamer primers, and the nucleic acid polymerase can comprise Phi29 DNA polymerase. The kit can further comprise one or more components that, when mixed in appropriate amounts, produce a reaction mixture having final concentrations of 10 mM $MgCl_2$, 37.5 mM Tris-HCl, pH 7, 50 mM KCl, 20 mM Ammonium Sulfate, and 1 mM dNTPs. The kit can further comprise any one or a combination of a stabilization solution, a lysis solution, a reaction mix that comprises the set of primers, dithiotheitol, Phosphate-Buffered Saline, and control DNA template. The stabilization solution can comprise 800 mM Tris-HCl, pH 4; the lysis solution can comprise 400 mM KOH, 100 mM dithiothreitol, and 10 mM EDTA; the reaction mix can comprise 150 mM Tris-HCl, 200 mM KCl, 40 mM $MgCl_2$, 20 mM $(NH_4)_2SO_4$, 4 mM deoxynucleotide triphosphates, and 0.2 mM random hexamer primers; the dithiothreitol can comprise 1M dithiotheitol; and the Phosphate-Buffered Saline can comprise 1× Phosphate-Buffered Saline, pH 7.5. The components of such kits are described elsewhere herein.

Any of the components that can be present in a kit that can be used together can be combined in a single component of the kit. Thus, a reaction mix can include, for example, buffers, deoxynucleotide triphosphates and primers. Similarly, components and solutions can be divided into constituent parts or sub-solutions. The kits can be used for any purpose, generally for nucleic acid amplification. In some forms, the kit can be designed to detect nucleic acid sequences of interest in a genome or other nucleic acid sample. In some forms, the kit can be designed to assess a disease, condition or predisposition of an individual based on a nucleic acid sequences of interest.

O. Mixtures

Disclosed are mixtures formed by performing, or formed during the course of performing, any form of the disclosed method. For example, disclosed are mixtures comprising, for example, a thermolabile nucleic acid polymerase having strand displacement activity, an additive, and a set of primers; a thermolabile nucleic acid polymerase having strand displacement activity, an additive, a set of primers, cells and lysis solution; a thermolabile nucleic acid polymerase having strand displacement activity, an additive, a set of primers, cell lysate and stabilization solution; a thermolabile nucleic acid polymerase having strand displacement activity, an additive, a set of primers, and stabilized cell lysate; a thermolabile nucleic acid polymerase having strand displacement activity, an additive, a set of primers, stabilized cell lysate and replicated strands; a thermolabile nucleic acid polymerase having strand displacement activity, an additive, a set of primers, stabilized cell lysate and one or more detection probes; a thermolabile nucleic acid polymerase having strand displacement activity, an additive, a set of primers, sample and stabilization solution.

Whenever the method involves mixing or bringing into contact, for example, compositions or components or reagents, performing the method creates a number of different mixtures. For example, if the method includes three mixing steps, after each one of these steps a unique mixture is formed if the steps are performed sequentially. In addition, a mixture is formed at the completion of all of the steps regardless of how the steps were performed. The present disclosure contemplates these mixtures, obtained by the performance of the disclosed method as well as mixtures containing any disclosed reagent, composition, or component, for example, disclosed herein.

Uses

The disclosed methods and compositions are applicable to numerous areas including, but not limited to, analysis of nucleic acids present in cells (for example, analysis of genomic DNA in cells), disease detection, mutation detection, gene discovery, gene mapping (molecular haplotyping), and agricultural research. Particularly useful is whole genome amplification. Other uses include, for example, detection of nucleic acids in cells and on genomic DNA arrays; molecular haplotyping; mutation detection; detection of inherited diseases such as cystic fibrosis, muscular dystrophy, diabetes, hemophilia, sickle cell anemia; assessment of predisposition for cancers such as prostate cancer, breast cancer, lung cancer, colon cancer, ovarian cancer, testicular cancer, pancreatic cancer.

Method

Disclosed are methods for amplification of nucleic acid sequences of interest with greater efficiency and fidelity. The disclosed method relates to isothermal amplification techniques, such as Multiple Displacement Amplification (MDA), where the generation of DNA artifacts is decreased or eliminated. Generally, this can be accomplished by carrying out the reaction at elevated temperature. In particularly useful embodiments of the method, sugars and/or other additives can be used to stabilized the polymerase at high temperature.

It has been discovered that generation of high molecular weight artifacts, in an isothermal amplification procedure, is substantially reduced or eliminated while still allowing the desired amplification of input DNA by carrying out the reaction at a higher temperature and, optionally, in the presence of one or more additives. For example, the amplification reaction can be carried out in the presence of sugars at a temperature that is higher then the normal optimal temperature for the DNA polymerase being used. It also has been discovered that isothermal amplification reactions can produce amplification products of high quality, such as low amplification bias, if performed at a higher temperature and, optionally, in the presence of one or more additives.

Disclosed is a method of amplifying nucleic acids, the method comprising incubating nucleic acids comprising target sequences at an elevated temperature in the presence of a thermolabile nucleic acid polymerase having strand displacement activity, an additive, and a set of primers, under conditions promoting replication of the nucleic acids. Replication of the nucleic acids results in replicated strands. During replication at least one of the replicated nucleic acid strands is displaced by strand displacement replication of another replicated strand. Formation of replicated strands from the target sequences is favored over formation of replicated strands from non-target sequences. Such favored formation can involve any suitable measure of replicated strand formation, such as relative rates of formation, relative amounts of replicated strands formed, amounts of replicated strands formed in comparison to the proportion of the template sequences in the reaction. As one measure, formation of replicated strands from target sequences is favored over formation of replicated strands from non-target sequences when more replicated strands from the target sequences are formed than replicated strands from non-target sequences relative to the proportions of target sequences to non-target sequences present in the reaction. As another measure, formation of replicated strands from target sequences is favored over formation of replicated strands from non-target sequences when the ratio of replicated strands formed from the target sequences to replicated strands formed from non-target sequences increases relative to a standard or control ratio (such as the ratio of the replicated strands observed at non-elevated temperatures).

Also disclosed is a method of amplifying a whole genome, the method comprising exposing cells to alkaline conditions to form a cell lysate, reducing the pH of the cell lysate to form a stabilized cell lysate, and incubating stabilized cell lysate at an elevated temperature in the presence of a thermolabile nucleic acid polymerase having strand displacement activity, an additive, and a set of primers, under conditions promoting replication of the nucleic acids. Replication of the nucleic acids results in replicated strands. During replication at least one of the replicated nucleic acid strands is displaced by strand displacement replication of another replicated strand. Formation of replicated strands from the target sequence is favored over formation of replicated strands from non-target sequences. The cell lysate comprises a whole genome.

Also disclosed is a method of performing strand displacement nucleic acid synthesis at an elevated temperature, the method comprising mixing thermolabile nucleic acid polymerase having strand-displacement activity, nucleic acids comprising target sequences, a set of primers, and an additive, and incubating at an elevated temperature and under conditions favoring hybridization of the primers to the target sequences and extension of the primers by the addition of nucleotides sequentially to the 3' end of the primer in a template-dependent manner, wherein the extension results in replication of the target sequences.

Also disclosed is a method of amplifying a whole genome, the method comprising exposing cells to alkaline conditions to form a cell lysate, wherein the cell lysate comprises a whole genome, reducing the pH of the cell lysate to form a stabilized cell lysate, and incubating stabilized cell lysate at an elevated temperature in the presence of a thermolabile nucleic acid polymerase having strand displacement activity, an additive, a set of primers, and deoxyribonucleotide triphosphates under conditions promoting replication of nucleic acids. During replication at least one of the replicated nucleic acid strands is displaced by strand displacement replication of another replicated strand. Formation of template-dependent extension products in the replication reaction is favored over formation of non-templated product.

Also disclosed is a method of performing strand displacement nucleic acid synthesis at an elevated temperature, the method comprising mixing thermolabile nucleic acid polymerase having strand-displacement activity, single-stranded template nucleic acid, a set of primers, deoxyribonucleotide triphosphates and an additive, and incubating at an elevated temperature and under conditions favoring hybridization of primer to template nucleic acid and extension of primer by the addition of nucleotides sequentially to the 3' end of the primer in a template-dependent manner, wherein said polymerization results in replication of said template nucleic acid.

Also disclosed is a method of amplifying nucleic acids, the method comprising incubating nucleic acids at an elevated temperature in the presence of a thermolabile nucleic acid polymerase having strand displacement activity, an additive, a set of primers, and deoxyribonucleotide triphosphates under conditions promoting replication of nucleic acids. During replication at least one of the replicated nucleic acid strands is displaced by strand displacement replication of another replicated strand. Formation of template-dependent extension products in the replication reaction is favored over formation of non-templated product.

In some forms of the disclosed method, a genomic sample is prepared by exposing the sample to alkaline conditions to denature the nucleic acids in the sample; reducing the pH of the sample to make the pH of the sample compatible with DNA replication; and incubating the sample at an elevated temperature in the presence of a thermolabile nucleic acid polymerase having strand displacement activity, an additive, and a set of primers, under conditions promoting replication of the nucleic acids. Replication of the nucleic acids results in replicated strands. During replication at least one of the replicated nucleic acid strands is displaced by strand displacement replication of another replicated strand. Formation of replicated strands from the target sequences is favored over formation of replicated strands from non-target sequences.

The disclosed methods can be performed on any desired samples. For example, the disclosed methods can be performed using samples that contain or are suspected of containing nucleic acids. Some forms of the disclosed methods do not require knowledge of any sequence present in a sample in order to amplify nucleic acids in the sample. Accordingly, some forms of the disclosed methods can be used to determine if a sample contains nucleic acids. If amplification products are produced when the method is performed, the sample contains nucleic acids. The disclosed methods can be performed on cells and on nucleic acid samples, including crude nucleic acid samples, partially purified nucleic acid sample, and purified nucleic acid samples. Exposing any cell or nucleic acid sample to alkaline conditions and then reducing the pH of the sample can produce a stabilized sample suitable for amplification or replication.

The disclosed method is based on strand displacement replication of the nucleic acid sequences by multiple primers. The method can be used to amplify one or more specific sequences (multiple strand displacement amplification), an entire genome or other DNA of high complexity (whole genome strand displacement amplification), or concatenated DNA (multiple strand displacement amplification of concatenated DNA). The disclosed method generally involves hybridization of primers to a target nucleic acid sequence and replication of the target sequence primed by the hybridized primers such that replication of the target sequence results in replicated strands complementary to the target sequence. During replication, the growing replicated strands displace other replicated strands from the target sequence (or from another replicated strand) via strand displacement replication. As used herein, a replicated strand is a nucleic acid strand resulting from elongation of a primer hybridized to a target sequence or to another replicated strand. Strand displacement replication refers to DNA replication where a growing end of a replicated strand encounters and displaces another strand from the template strand (or from another replicated strand). Displacement of replicated strands by other replicated strands is a hallmark of the disclosed method which allows multiple copies of a target sequence to be made in a single, isothermic reaction.

The disclosed method can accurately and evenly amplify the various sequences in highly complex nucleic acid samples. This result can be quantified by references to, for example, percent representation, sequence representation, sequence representation bias, percent sequence representation, locus representation, locus representation bias, percent locus representation, and/or amplification bias. For example, the replicated nucleic acid molecules produced in the disclosed method can have a sequence representation or sequence representation bias of at least 50% for at least 10 different target sequences. The amplification bias can be less than 10% for at least 10 different target sequences.

Nucleic acids for amplification are often obtained from cellular samples. This generally requires disruption of the cell (to make the nucleic acid accessible) and purification of the nucleic acids prior to amplification. It also generally requires the inactivation of protein factors such as nucleases that could degrade the DNA, or of factors such as histones that could bind to DNA strands and impede their use as a template for DNA synthesis by a polymerase. There are a variety of techniques used to break open cells, such as sonication, enzymatic digestion of cell walls, heating, and exposure to lytic conditions.

In some forms of the disclosed method, a genomic sample is prepared by exposing cells to alkaline conditions, thereby lysing the cells and resulting in a cell lysate; reducing the pH of the cell lysate to make the pH of the cell lysate compatible with DNA replication; and incubating the cell lysate at an elevated temperature in the presence of a thermolabile nucleic acid polymerase having strand displacement activity, an additive, and a set of primers, under conditions promoting replication of nucleic acids in the cell lysate. Replication of the nucleic acids results in replicated strands. During replication at least one of the replicated nucleic acid strands is displaced by strand displacement replication of another replicated strand. Formation of replicated strands from the target sequences is favored over formation of replicated strands from non-target sequences. Alkaline conditions are conditions where the pH is greater than 9.0. Particularly useful alkaline conditions for the disclosed method are conditions where the pH is greater than 10.0. The alkaline conditions can be, for example, those that cause a substantial number of cells to lyse, those that cause a significant number of cells to lyse, or those that cause a sufficient number of cells to lyse. The number of lysed cells can be considered sufficient if the genome can be sufficiently amplified in the disclosed method. The amplification is sufficient if enough amplification product is produced to permit some use of the amplification product, such as detection of sequences or other analysis. The reduction in pH is generally into the neutral range of pH 9.0 to pH 6.0.

Samples can be exposed to alkaline conditions by mixing the sample with a lysis solution. The amount of lysis solution mixed with the sample can be that amount that causes a substantial denaturation of the nucleic acids in the sample. Generally, this volume will be a function of the pH of the sample/lysis solution mixture. The lysis solution can be formulated such that the sample is mixed with an equal volume of the lysis solution (to produce the desired alkaline conditions). Cells can be exposed to alkaline conditions by mixing the cells with a lysis solution. The amount of lysis solution mixed with the cells can be that amount that causes a substantial number of cells to lyse or those that cause a sufficient number of cells to lyse. Generally, this volume will be a function of the pH of the cell/lysis solution mixture. The lysis solution can be formulated such that the cells are mixed with an equal volume of the lysis solution (to produce the desired alkaline conditions).

The pH of the cell lysate or sample can be reduced to form a stabilized cell lysate. A stabilized cell lysate or sample is a cell lysate or sample the pH of which is in the neutral range (from about pH 6.0 to about pH 9.0). Useful stabilized cell lysates or samples have a pH that allows replication of nucleic acids in the cell lysate. For example, the pH of the stabilized cell lysate or sample is usefully at a pH at which the DNA polymerase can function. The pH of the cell lysate or sample can be reduced by mixing the cell lysate or sample with a stabilization solution. The stabilization solution comprises a solution that can reduce the pH of a cell lysate or sample exposed to alkaline conditions as described elsewhere herein.

The amount of stabilization solution mixed with the sample can be that amount that causes a reduction in pH to the neutral range (or other desired pH value). Generally, this volume will be a function of the pH of the sample/stabilization solution mixture. The stabilization solution can be formulated such that the sample is mixed with an equal volume of the stabilization solution (to produce the desired pH). The amount of stabilization solution mixed with the cell lysate can be that amount that causes a reduction in pH to the neutral range (or other desired pH value). Generally, this volume will be a function of the pH of the cell lysate/stabilization solution mixture. The stabilization solution can be formulated such that the cell lysate is mixed with an equal volume of the stabilization solution (to produce the desired pH).

In some embodiments, the cells are not lysed by heat. Those of skill in the art will understand that different cells under different conditions will be lysed at different temperatures and so can determine temperatures and times at which the cells will not be lysed by heat. In general, the cells are not subjected to heating above a temperature and for a time that would cause substantial cell lysis in the absence of the alkaline conditions used. As used herein, substantial cell lysis refers to lysis of 90% or greater of the cells exposed to the alkaline conditions. Significant cell lysis refers to lysis of 50% or more of the cells exposed to the alkaline conditions. Sufficient cell lysis refers to lysis of enough of the cells exposed to the alkaline conditions to allow synthesis of a detectable amount of amplification products by multiple strand displacement amplification. In general, the alkaline conditions used in the disclosed method need only cause sufficient cell lysis. It should be understood that alkaline conditions that could cause significant or substantial cell lysis need not result in significant or substantial cell lysis when the method is performed.

In some embodiments, the cells are not subjected to heating substantially or significantly above the temperature at which the cells grow. As used herein, the temperature at which the cells grow refers to the standard temperature, or highest of different standard temperatures, at which cells of the type involved are cultured. In the case of animal cells, the temperature at which the cells grow refers to the body temperature of the animal. In other embodiments, the cells are not subjected to heating substantially or significantly above the temperature of the amplification reaction (where the genome is replicated).

In some embodiments, the cell lysate or sample is not subjected to purification prior to the amplification reaction. In the context of the disclosed method, purification generally refers to the separation of nucleic acids from other material in the cell lysate or sample. It has been discovered that multiple displacement amplification can be performed on unpurified and partially purified samples. It is commonly thought that amplification reactions cannot be efficiently performed using unpurified nucleic acid. In particular, PCR is very sensitive to contaminants.

Forms of purification include centrifugation, extraction, chromatography, precipitation, filtration, and dialysis. Partially purified cell lysate or samples includes cell lysates or samples subjected to centrifugation, extraction, chromatography, precipitation, filtration, and dialysis. Partially purified cell lysate or samples generally does not include cell lysates or samples subjected to nucleic acid precipitation or dialysis. As used herein, separation of nucleic acid from other material refers to physical separation such that the nucleic acid to be amplified is in a different container or container from the material. Purification does not require separation of all nucleic acid from all other materials. Rather, what is required is separation of some nucleic acid from some other material. As used herein in the context of nucleic acids to be amplified, purification refers to separation of nucleic acid from other material. In the context of cell lysates, purification refers to separation of nucleic acid from other material in the cell lysate. As used herein, partial purification refers to separation of nucleic acid from some, but not all, of other material with which the nucleic acid is mixed. In the context of cell lysates, partial purification refers to separation of nucleic acid from some, but not all, of the other material in the cell lysate.

Unless the context clearly indicates otherwise, reference herein to a lack of purification, lack of one or more types of purification or separation operations or techniques, or exclusion of purification or one or more types of purification or separation operations or techniques does not encompass the exposure of cells or samples to alkaline conditions (or the results thereof) or the reduction of pH of a cell lysate or sample (or the results thereof). That is, to the extent that the alkaline conditions and pH reduction of the disclosed method produce an effect that could be considered "purification" or "separation," such effects are excluded from the definition of purification and separation when those terms are used in the context of processing and manipulation of cell lysates, samples, stabilized samples and stabilized cell lysates (unless the context clearly indicates otherwise).

As used herein, substantial purification refers to separation of nucleic acid from at least a substantial portion of other material with which the nucleic acid is mixed. In the context of cell lysates, substantial purification refers to separation of nucleic acid from at least a substantial portion of the other material in the cell lysate. A substantial portion refers to 90% of the other material involved. Specific levels of purification can be referred to as a percent purification (such as 95% purification and 70% purification). A percent purification refers to purification that results in separation from nucleic acid of at least the designated percent of other material with which the nucleic acid is mixed.

Denaturation of nucleic acid molecules to be amplified is common in amplification techniques. This is especially true when amplifying genomic DNA. In particular, PCR uses multiple denaturation cycles. Denaturation is generally used to make nucleic acid strands accessible to primers. Target nucleic acids, genomic DNA, for example, need not be denatured for efficient multiple displacement amplification. Elimination of a denaturation step and denaturation conditions has additional advantages such as reducing sequence bias in the amplified products. In some embodiments, the nucleic acids in the cell lysate or sample are not denatured by heating. In some embodiments, the cell lysate is not subjected to heating substantially or significantly above the temperature at which the cells grow. In other embodiments, the cell lysate or sample is not subjected to heating substantially or significantly above the temperature of the amplification reaction (where the genome is replicated). The disclosed multiple displacement amplification reaction is generally conducted at a substantially constant temperature (that is, the amplification reaction is substantially isothermic), and this temperature is generally below the temperature at which the nucleic acids would be notably denatured. As used herein, notable denaturation refers to denaturation of 10% or greater of the base pairs.

In preferred forms of the disclosed method, the nucleic acid sample or template nucleic acid is not subjected to denaturing conditions and/or no denaturation step is used. In some forms of the disclosed method, the nucleic acid sample or template nucleic acid is not subjected to heat denaturing conditions and/or no heat denaturation step is used. It should be understood that while sample preparation (for example, cell lysis and processing of cell extracts) may involve conditions that might be considered denaturing (for example, treatment with alkali), the denaturation conditions or step eliminated in some forms of the disclosed method refers to denaturation steps or conditions intended and used to make nucleic acid strands accessible to primers. Such denaturation is commonly a heat denaturation, but can also be other forms of denaturation such as chemical denaturation. It should be understood that in the disclosed method where the nucleic acid sample or template nucleic acid is not subjected to denaturing conditions, the template strands are accessible to the primers (since amplification occurs). However, the template stands are not made accessible via general denaturation of the sample or template nucleic acids.

The pH of all or a portion of a sample or cells exposed to alkaline conditions can be reduced to form a stabilized or neutralized sample or cell lysate, and an amplification mixture can comprise all or a portion of the neutralized or stabilized sample or cell lysate. An amplification mixture is the reaction solution where nucleic acids are amplified. An amplification mixture can comprise a genome, and the genome can comprise any fraction of the nucleic acids in the amplification mixture. The genome can comprise, for example, at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, at least 96%, at least 97%, at least 98%, or at least 99% of the nucleic acids in the amplification mixture.

The efficiency of a DNA amplification procedure may be described for individual loci as the percent representation, where the percent representation is 100% for a locus in genomic DNA as purified from cells. Amplification bias may be calculated between two samples of amplified DNA or between a sample of amplified DNA and the template DNA it was amplified from. The bias is the ratio between the values for percent representation (or for locus representation) for a particular locus. The maximum bias is the ratio of the most highly represented locus to the least represented locus. Percent representation is a form of representation bias. Thus, percent locus representation is a form of locus representation bias.

The disclosed methods can produce high quality amplification products. For example, the disclosed methods can produce a low amplification bias. As used herein, a low amplification bias includes amplification biases of less than 10-fold for at least 5 sequences or loci, less than 12-fold for at least 6 sequences or loci, less than 14-fold for at least 7 sequences or loci, less than 16-fold for at least 8 sequences or loci, less than 18-fold for at least 9 sequences or loci, less than 20-fold for at least 10 sequences or loci, less than 22-fold for at least 11 sequences or loci, less than 24-fold for at least 12 sequences or loci, less than 26-fold for at least 13 sequences or loci, less than 28-fold for at least 14 sequences or loci, less than 30-fold for at least 15 sequences or loci, less than 32-fold for at least 16 sequences or loci, less than 34-fold for at least 17 sequences or loci, less than 36-fold for at least 18 sequences or loci, less than 38-fold for at least 19 sequences or loci, less than 40-fold for at least 20 sequences or loci, less than 42-fold for at least 21 sequences or loci, less than 44-fold for at least 22 sequences or loci, less than 46-fold for at least 23 sequences or loci, less than 48-fold for at least 24 sequences or loci, and less than 50-fold for at least 25 sequences or loci. Generalizing, low amplification bias includes amplification biases of 2x-fold where x is the number of sequences or loci over which the amplification bias is calculated or observed. Low amplification bias can be expressed in other ways, such as by allele bias, locus representation, sequence representation, allele representation, locus representation bias, sequence representation bias, percent representation, percent locus representation, percent sequence representation, and other measures that indicate low bias and/or complete amplification of the input nucleic acids. The values of such other measures that constitute low amplification bias generally can be calculated by reference to the above definition and formula in view of the relationships between amplification bias and other measures of bias described elsewhere herein.

In another form of the method, the primers can be hexamer primers. Such short, 6 nucleotide primers can still prime multiple strand displacement replication efficiently. Such short primers are easier to produce as a complete set of primers of random sequence (random primers) than longer primers at least because there are fewer to make. In another form of the method, the primers can each contain at least one modified nucleotide such that the primers are nuclease resistant. In another form of the method, the primers can each contain at least one modified nucleotide such that the melting temperature of the primer is altered relative to a primer of the same sequence without the modified nucleotide(s). In another form of the method, the DNA polymerase can be φ29 DNA polymerase. φ29 DNA polymerase produces greater amplification in multiple displacement amplification.

A form of the disclosed method can be illustrated by the following protocol. This protocol can be used for any type of sample, such as cell samples and nucleic acid samples.

1. Denaturation of the genomic DNA template before amplification. Prepare the Lysis Solution by diluting Solution A by 1:4 with $H_2O$ (e.g. 100 μL of Solution A into 300 μL of $H_2O$). Prepare the Stabilization Buffer by diluting Solution B by 1:5 with $H_2O$ (for example, 100 μL of Solution A into 400 μL of $H_2O$). Both Lysis and Stabilization Solution should be prepared fresh before each new experiment. After use, the bottle containing Solution A should be resealed immediately to avoid neutralization from $CO_2$.

Solution A has a useful shelf-life of 6 months. Prepare a fresh Solution A if it has been stored more than 6 months.

| | |
|---|---|
| Solution A: | 400 mM KOH, 10 mM EDTA, pH 8 |
| Solution B: | 800 mM Tris Hydrochloride, pH 4 |

2. Add 2.5 μL of the Lysis Solution to each 0.2 mL thermocycler tube containing 2.5 μL of genomic DNA on ice. Mix well by pipetting up and down 5 times. Incubate the tubes or plate on ice for 3 minutes.

3. Stop the denaturation reaction after 3 minutes by adding 5 μL of the Stabilization Buffer to each sample and control. Remove the tubes from ice. Proceed immediately to the amplification reaction.

4. To the tube from Step 3, add in a final volume of 50 μl:
Required amount of genomic DNA,
0.3M Trehalose,
10 mM $MgCl_2$,
37.5 mM Tris/HCl pH: 7,
50 mM KCl,
20 mM Ammonium Sulfate,
1 mM dNTPs,
50 μM exonuclease-resistant random hexamer oligonucleotide,
40 units of Phi29 DNA polymerase.
Incubate at 40° C. for 6-16 hrs.

The disclosed methods, either in whole or in part, can be performed in or on solid supports or in or on reaction chambers. For example, the disclosed replication, incubation and amplification steps can be performed with the amplification mixture in or on solid supports or in or on reaction chambers. For example, the disclosed replication, incubation and amplification steps can be performed with the amplification mixture on solid supports having reaction chambers. A reaction chamber is any structure in which a separate amplification reaction can be performed. Useful reaction chambers include tubes, test tubes, eppendorf tubes, vessels, micro vessels, plates, wells, wells of micro well plates, wells of microtitre plates, chambers, micro fluidics chambers, micro machined chambers, sealed chambers, holes, depressions, dimples, dishes, surfaces, membranes, microarrays, fibers, glass fibers, optical fibers, woven fibers, films, beads, bottles, chips, compact disks, shaped polymers, particles, microparticles or other structures that can support separate reactions. Reaction chambers can be made from any suitable material. Such materials include acrylamide, cellulose, nitrocellulose, glass, gold, polystyrene, polyethylene vinyl acetate, polypropylene, polymethacrylate, polyethylene, polyethylene oxide, glass, polysilicates, polycarbonates, teflon, fluorocarbons, nylon, silicon rubber, polyanhydrides, polyglycolic acid, polylactic acid, polyorthoesters, functionalized silane, polypropylfumerate, collagen, glycosaminoglycans, and polyamino acids. Solid supports preferably comprise arrays of reaction chambers. In connection with reaction chambers, a separate reaction refers to a reaction where substantially no cross contamination of reactants or products will occur between different reaction chambers. Substantially no cross contamination refers to a level of contamination of reactants or products below a level that would be detected in the particular reaction or assay involved. For example, if nucleic acid contamination from another reaction chamber would not be detected in a given reaction chamber in a given assay (even though it may be present), there is no substantial cross contamination of the nucleic acid. It is understood, therefore, that reaction chambers can comprise, for example, locations on a planar surface, such as spots, so long as the reactions performed at the locations remain separate and are not subject to mixing.

A. Whole Genome Strand Displacement Amplification

In one form of the method, referred to as whole genome strand displacement amplification (WGSDA), a random or partially random set of primers is used to randomly prime a sample of genomic nucleic acid (or another sample of nucleic acid of high complexity). By choosing a sufficiently large set of primers of random or mostly random sequence, the primers in the set will be collectively, and randomly, complementary to nucleic acid sequences distributed throughout nucleic acid in the sample. Amplification proceeds by replication with a processive polymerase initiated at each primer and continuing until spontaneous termination. A key feature of this method is the displacement of intervening primers during replication by the polymerase. In this way, multiple overlapping copies of the entire genome can be synthesized in a short time.

Whole genome strand displacement amplification can be performed by (a) mixing a set of random or partially random primers with a genomic sample (or other nucleic acid sample of high complexity), to produce a primer-target sample mixture, and incubating the primer-target sample mixture under conditions that promote hybridization between the primers and the genomic DNA in the primer-target sample mixture, and (b) mixing DNA polymerase with the primer-target sample mixture, to produce a polymerase-target sample mixture, and incubating the polymerase-target sample mixture at an elevated temperature in the presence of a thermolabile nucleic acid polymerase having strand displacement activity, an additive, and a set of primers, under conditions promoting replication of nucleic acids in the sample. Replication of the nucleic acids results in replicated strands. During replication at least one of the replicated nucleic acid strands is displaced by strand displacement replication of another replicated strand. Formation of replicated strands from the target sequences is favored over formation of replicated strands from non-target sequences.

B. Analysis of Amplification Products

Clinical and health science studies require ready access to large quantities of genomic DNA to serve as inputs for multiparametric assays of polymorphic sites in DNA, whose combined results provide valuable prognostic and diagnostic information. However, these studies are hampered by severe lack of adequate supply of DNA, as most biopsy methods yield only minute quantities of tissue or cells. Sample preparative steps further reduce the amounts recovered from these cells due to loss during cell fractionation, thereby limiting the number of chromosomal loci that can be examined per sample using the isolated genomic DNA as input. Methods of the present invention seek to overcome these shortages by providing adequate and renewable supply of DNA for the multiparametric analyses.

Analysis of loss of heterozygosity (LOH), a relatively common type of genetic alteration found throughout the genome in most solid neoplasms, is frequently employed in cancer diagnosis. While a number of familial cancer genes with high-penetrance mutations are readily identified, success in determining clinical outcomes by LOH analysis to evaluate risk of sporadic cancer development is predicated also on contributions from low-penetrance genetic variants or polymorphisms. Such multiparametric assays require simultaneous analysis of a large number of candidate and other genetic loci from each sample for effective determination and statistical evaluation of disease progression and staging that are presently beyond the scope of measurements using native DNA prepared from the clinical sample. Amplification of genomic DNA present in these samples is a useful adjunct for providing the necessary amounts of DNA required for the multiparametric analyses. The disclosed methods can provide high quality nucleic acids that provides sufficient material for analyses such as LOH analyses.

The progressive loss of form and structure of DNA in cancer cells culminates in dozens of different genes becoming aberrant in nucleotide sequence or copy number, with hundreds or thousands of genes being differentially expressed in diseased cells compared to normal or premalignant cells. Elucidating the temporal and spatial attributes of the complex somatic genetic events delineating emerging cancer cells will aid the search for the more elusive germline variants that confer increased susceptibility. The disclosed methods can provide sufficient amounts of nucleic acids amplified from sample sources to analyze these extensive changes in the genome. This can allow increased throughput of such measurements and efficient utilization of DNA recovered from these samples.

Some forms of the disclosed methods provide accurate and reproducible replication of sample DNA, so as to generate minimal, if any, changes in nucleotide sequence distributions of replicated DNA strands from that of the input DNA. Many prior nucleic acid amplification methods introduce at least some significant degree of artifactual variation in sequence of the amplified DNA leading to bias in the representation of different sequences in the amplified nucleic acids relative to representation of those sequences in the starting nucleic acids. Such bias can be referred to as sequence bias or allele bias.

In some cases, allele bias can be attributed to the properties of the polymerase enzyme employed in the amplification reaction. For example, 'proofreading' DNA polymerases are less susceptible to introducing allele bias in replicated DNA than DNA polymerases that lack proofreading activity. Misincorporation of one or more nucleotides by DNA polymerase during DNA synthesis could lead to replication bias or 'allele bias' during DNA amplification the change produces a different sequence that may be scored or detected as a different sequence or allele. Other factors that can contribute to replication bias include the extent of or fold amplification of input DNA wherein more rounds of amplification could lead to increased allele bias in the replicated DNA, reaction conditions requiring treatment of amplification mixtures at elevated temperatures, treatments that promote creation of abasic sites in DNA, impurities in input DNA that may render the polymerase more error-prone, the nature and concentration of reagent components in the amplification reaction, including presence of chaotropic agents, positively charged metal ions, and so on.

In some cases, nucleotide incorporation errors leading to allele bias can be due to a property of the nucleic acid template being amplified. For example, regions of DNA containing repeats or stretches of repeats of a single or few nucleotides can sometimes lead to polymerase slippage, resulting in artifactual insertions or deletions of one or more nucleotides. For this reason, faithful amplification of DNA in repeat regions can be difficult to achieve. These regions include, di-, tri-, and tetra-nucleotide repeats, telomeric regions, regions containing long interspersed repeats, STR's and other kinds of repeats described in the literature. Regions of DNA containing extensive secondary structure can sometimes prevent traverse of polymerase across the region, and may result in such sequences being under-represented among the replicated strand populations as well as introduction of allele bias.

Some forms of the disclosed methods provide for minimal differences in allele ratios between input nucleic acids and amplification products (which is allele bias—a form of amplification bias). Allele ratio can be defined as the peak height (that is, amount detected) of the smaller allele divided by that of the larger allele (Paulson et al, 1999; herein incorporated by reference). Typically, allele ratios of a sample set of selected genetic loci are measured by performing genotyping assays of replicated or input DNA using a standard genotyping assay. Genotyping assays are well known to one of ordinary skill in the art examples of which are described in U.S. Pat. Nos. 5,451,067, 6,679,242, 6,479,244, 6,472,185, 6,458,544, 6,440,707, and 6,312,902, which are herein incorporated by reference. If the alleles are present in equal numbers (as would be expected for a heterozygous locus), the allele ratio is 1 and there is no allele bias. As used herein, allele bias refers to a difference in the allele ratio for a pair of alleles from an allele ratio of 1. For alleles that do not have an even ratio (that is, a ratio of 1), allele bias can refer to a difference from the normal or expected allele ratio. Generally, the allele ratio for a locus in a heterozygous diploid sample will be 1, and this should be the allele ratio measurable in the unamplified sample. When a sample is amplified, uneven amplification can result in a bias in the allele ratio. Allele bias can be calculated, for example, as the difference between the allele ratio of alleles in an unamplified sample and the allele ratio for the same alleles in DNA amplified from the sample. This can be referred to as amplification allele bias. Amplification allele bias, when present, indicates that the ratio of alleles in the amplified DNA has been altered from the ratio in the original, unamplified genomic DNA. As an example, the allele ratio of two alleles of a locus that are present in equal number is 1. If the amplified DNA has a ratio of these two alleles of 0.5, then the amplification allele bias is 0.5 (calculated as 0.5/1=0.5). Such a bias can also be represented as 50% (referring to the difference in the ratios—0.5 is 50% of 1) or 2-fold (referring to the fold difference in the allele ratios—1 is twice as large as 0.5).

Allele bias can also be quantified by assessing allele representation. The fraction of all alleles that a given allele represents is the allele representation for that allele. In the case where two alleles at a locus each represent half of the total (the normal case for heterozygous loci), then each allele can be said to have an allele representation of 50% or 0.5. Allele bias would be present if either allele had a representation different from 50%. If there is no difference between the allele representation in the input nucleic acid and the allele representation in the amplified DNA, then there is no allele bias, which can be represented as an allele bias of 1 or of 100%. In the case of allele representation, allele bias can be calculated as the ratio of the allele representations in two samples to be compared (for example, unamplified sample versus amplified DNA). Thus, 50% representation over 50% representation equals 1. Allele bias can also be expressed as the standard deviation from an allele representation of 50% (or from the normal or expected allele representation). When allele ratios of input and amplified DNA samples are same, then the amplified DNA is said to have no allele bias.

The disclosed method can accurately and evenly amplify the various sequences in highly complex nucleic acid samples. This result can be quantified by reference to, for example, percent representation, sequence representation, sequence representation bias, percent sequence representation, locus representation, locus representation bias, percent locus representation, and/or amplification bias. For example, the replicated nucleic acid molecules produced in the disclosed method can have a sequence representation or sequence representation bias of at least 50% for at least 10 different target sequences. The amplification bias can be less than 10% for at least 10 different target sequences.

The disclosed methods generally will produce amplified DNA with low allele bias. The disclosed methods can be used to measure allele bias and other amplification biases in amplified nucleic acids. For example, consider a case of an individual who is heterozygous for a selected genetic locus. The allele ratio of genomic DNA from this individual for this locus is one. An aliquot of genomic DNA from this individual could be subjected to whole genome amplification by employing the disclosed methods. If allele bias occurred during whole genome amplification, the amplified DNA would contain a greater representation of DNA copies of one of the parental alleles compared to the other parental allele. If DNA fragments containing either of the parental alleles greatly predominate in the amplified DNA population, then the genotyping test could score the DNA sample as being homozygous for that parental allele, leading to a misdiagnosis as homozygous normal. This failure to detect a heterozygous genotype as a consequence of nucleic acid amplification can be referred to as heterozygous dropout or allele drop out (ADO). In the case of homozygotes, wherein both parental alleles are same, ADO is easier to detect. The disclosed methods are equally adaptable to measuring ADO at homozygous loci.

It is unnecessary to assay for the presence of ADO at most or all of the loci present in amplified DNA. In fact, it would be impractical to do so. For most applications, assays of a sample of loci should suffice. Various factors can be considered for determining the number of loci to be scored in order to determine the ADO of an amplified DNA sample. These factors include, but are not limited to, the size (in nucleotides) of the genome being amplified, estimated error rates of nucleotide incorporation by the polymerase employed for amplification, amplification reaction conditions, and the duration of the amplification reaction. In general, a larger genome size is expected to produce larger values for ADO due to the greater number of nucleotide additions per genome needed to complete amplification. The same is true of the duration of the amplification reaction, since a longer incubation time provides for a greater number of rounds of DNA amplification, thereby increasing the number of nucleotide additions. For instance, nucleotide misincorporation events that occur during early rounds of replication are more likely to be perpetuated and predominate in the final product of the amplification reaction, than those occurring during later rounds of amplification. For purposes of this calculation, contributions from reversions of misincorporated nucleotides to wild type are ignored, since these events are of very low probability, except at mutational hotspots. Different polymerases vary greatly in their rates of nucleotide incorporation errors generated during DNA replication. This is due, in part, to an intrinsic property of the polymerase itself. In general, polymerases lacking a 3',5'-exonuclease activity are more error-prone than those that possess such activity. Other factors that contribute to misincorporation of nucleotides by polymerases are known, and include, for example, the presence of impurities in the amplification reaction and the presence of reagents that alter the structure of the polymerase or otherwise render them error prone, including organic reagents and divalent metal ions. In general, the number of loci to be evaluated in the amplified DNA to obtain an estimate of the ADO can be estimated by the equation:

$$(G*RC)/PER$$

where G is the size of the genome (or complexity of the nucleic acids), RC is the average number of rounds of replication in the amplification, and PER is the polymerase error rate (that is, the rate of misincorporation of nucleotides).

In preferred embodiments, ADO can be determined by scoring alleles at only a sample number of loci. Typically, 2-8% of the number of ADO sites estimated using the equation above can be assayed. In general, 100-500 loci can be selected when human genomic DNA is employed in the amplification reaction. Selection of loci for ADO assays can be random or ordered. In preferred embodiments, loci can be selected on the basis of their location on a chromosome of interest, in close proximity to or greater than a selected genetic distance away from a locus or chromosomal landmark of interest, on the basis of known loci that are hypersensitive to ADO, or other criteria. An ordered selection of loci can further reduce the number of loci that need to be evaluated for measuring ADO. Thus, results from assays involving 1 to 2 loci, 2 to 5 loci, 5 to 10 loci, 10 to 20 loci, 20 to 50 loci, 50 to 100 loci, 100 to 200 loci, 200 to 500 loci, or more than 500 loci may suffice for measuring ADO.

C. Amplified Nucleic Acid Quality

The disclosed method can result in replication of all or a substantial fraction of the nucleic acid molecules in a nucleic acid sample. As used herein, a substantial fraction of the nucleic acid molecules in a nucleic acid sample refers to 90% or more of the nucleic acid molecules (or nucleic acid sequences) present in the nucleic acid sample. As used herein, a significant fraction of the nucleic acid molecules in a nucleic acid sample refers to 50% or more of the nucleic acid molecules (or nucleic acid sequences) present in the nucleic acid sample. As used herein, a notable fraction of the nucleic acid molecules in a nucleic acid sample refers to 20% or more of the nucleic acid molecules (or nucleic acid sequences) present in the nucleic acid sample.

Replication of the nucleic acid molecules in a nucleic acid sample can result replication of at least 0.01% of the nucleic acid sequences in the nucleic acid sample, at least 0.1% of the nucleic acid sequences in the nucleic acid sample, at least 1% of the nucleic acid sequences in the nucleic acid sample, at least 5% of the nucleic acid sequences in the nucleic acid sample, at least 10% of the nucleic acid sequences in the nucleic acid sample, at least 20% of the nucleic acid sequences in the nucleic acid sample, at least 30% of the nucleic acid sequences in the nucleic acid sample, at least 40% of the nucleic acid sequences in the nucleic acid sample, at least 50% of the nucleic acid sequences in the nucleic acid sample, at least 60% of the nucleic acid sequences in the nucleic acid sample, at least 70% of the nucleic acid sequences in the nucleic acid sample, at least 80% of the nucleic acid sequences in the nucleic acid sample, at least 90% of the nucleic acid sequences in the nucleic acid sample, at least 95% of the nucleic acid sequences in the nucleic acid sample, at least 96% of the nucleic acid sequences in the nucleic acid sample, at least 97% of the nucleic acid sequences in the nucleic acid sample, at least 98% of the nucleic acid sequences in the nucleic acid sample, or at least 99% of the nucleic acid sequences in the nucleic acid sample.

The fraction of the nucleic acid molecules in the nucleic acid sample that is replicated can vary with the sequence complexity of the nucleic acid sample (although higher fractions are preferred for all nucleic acid samples). For example, where the nucleic acid sample has a sequence complexity of at least $1 \times 10^9$ nucleotides, replication of nucleic acid molecules in the nucleic acid sample can result in replication of at least 0.01% of the nucleic acid sequences in the nucleic acid sample. Where the nucleic acid sample has a sequence complexity of at least $1 \times 10^8$ nucleotides, replication of nucleic acid molecules in the nucleic acid sample can result in replication of at least 0.1% of the nucleic acid sequences in the nucleic acid sample. Where the nucleic acid sample has a sequence complexity of at least $1 \times 10^7$ nucleotides, replication of nucleic acid molecules in the nucleic acid sample can result in replication of at least 1% of the nucleic acid sequences in the nucleic acid sample. Where the nucleic acid sample has a sequence complexity of at least $1 \times 10^6$ nucleotides, replication of nucleic acid molecules in the nucleic acid sample can result in replication of at least 10% of the nucleic acid sequences in the nucleic acid sample. Where the nucleic acid sample has a sequence complexity of at least $1 \times 10^5$ nucleotides, replication of nucleic acid molecules in the nucleic acid sample can result in replication of at least 80% of the nucleic acid sequences in the nucleic acid sample. Where the nucleic acid sample has a sequence complexity of at least $1 \times 10^4$ nucleotides, replication of nucleic acid molecules in the nucleic acid sample can result in replication of at least 90% of the nucleic acid sequences in the nucleic acid sample. Where the nucleic acid sample has a sequence complexity of at least $1 \times 10^3$ nucleotides, replication of nucleic acid molecules in the nucleic acid sample can result in replication of at least 96% of the nucleic acid sequences in the nucleic acid sample.

Where the nucleic acid sample has a sequence complexity of less than $1 \times 10^9$ nucleotides, replication of nucleic acid molecules in the nucleic acid sample can result in replication of at least 0.01% of the nucleic acid sequences in the nucleic acid sample. Where the nucleic acid sample has a sequence complexity of less than $1 \times 10^8$ nucleotides, replication of nucleic acid molecules in the nucleic acid sample can result in replication of at least 0.1% of the nucleic acid sequences in the nucleic acid sample.

Where the nucleic acid sample has a sequence complexity of less than $1 \times 10^7$ nucleotides, replication of nucleic acid molecules in the nucleic acid sample can result in replication of at least 1% of the nucleic acid sequences in the nucleic acid sample. Where the nucleic acid sample has a sequence complexity of less than $1 \times 10^6$ nucleotides, replication of nucleic acid molecules in the nucleic acid sample can result in replication of at least 10% of the nucleic acid sequences in the nucleic acid sample. Where the nucleic acid sample has a sequence complexity of less than $1 \times 10^5$ nucleotides, replication of nucleic acid molecules in the nucleic acid sample can result in replication of at least 80% of the nucleic acid sequences in the nucleic acid sample. Where the nucleic acid sample has a sequence complexity of less than $1 \times 10^4$ nucleotides, replication of nucleic acid molecules in the nucleic acid sample can result in replication of at least 90% of the nucleic acid sequences in the nucleic acid sample. Where the nucleic acid sample has a sequence complexity of less than $1 \times 10^3$ nucleotides, replication of nucleic acid molecules in the nucleic acid sample can result in replication of at least 96% of the nucleic acid sequences in the nucleic acid sample.

One measure of the quality of the amplified nucleic acids can be the percent representation, sequence representation, sequence representation bias, percent sequence representation, locus representation, locus representation bias, and/or percent locus representation in the amplified nucleic acids. A locus representation or sequence representation the same as or close to the locus or sequence representation in the source nucleic acid sample indicates amplified nucleic acids of the highest quality. Locus representation bias can refer to the ratio (usually expressed as a percentage) of the amount of a given locus in amplified nucleic acid to the amount of the same locus in the unamplified nucleic acid sample. In making this calculation, the measured amount of the locus in the amplified nucleic and the measured amount of the locus in the unamplified nucleic acid sample generally can be normalized to the total amount of nucleic acid present in the amplified nucleic acid and the unamplified nucleic acid sample, respectively. Locus representation or locus representation bias expressed as a percentage (usually of a reference locus representation) can be referred to as a percent locus representation (which is a form of percent representation). Locus representation bias can also be expressed as the standard deviation of the locus representation in an amplified sample from the locus representation in the unamplified sample (or other reference locus representation). Locus representation bias can be a form of amplification bias. Locus representation can refer to the amount or level of a given locus (or a group of loci). Locus representation can be expressed as a locus representation relative to another, reference locus representation. Thus, for example, a percent locus representation is a form of locus representation.

Sequence representation bias can refer to the ratio (usually expressed as a percentage) of the amount of a given sequence in amplified nucleic acid to the amount of the same sequence in the unamplified nucleic acid sample. In making this calculation, the measured amount of the sequence in the amplified nucleic and the measured amount of the sequence in the unamplified nucleic acid sample generally can be normalized to the total amount of nucleic acid present in the amplified nucleic acid and the unamplified nucleic acid sample, respectively. Sequence representation or sequence representation bias expressed as a percentage (usually of a reference sequence representation) can be referred to as a percent sequence representation (which is a form of percent representation). Sequence representation bias can also be expressed as the standard deviation of the sequence representation in an amplified sample from the sequence representation in the unamplified sample (or other reference locus representation). Sequence representation bias can be a form of amplification bias. Sequence representation can refer to the amount or level of a given sequence (or a group of sequences). Sequence representation can be expressed as a sequence representation relative to another, reference sequence representation. Thus, for example, a percent sequence representation is a form of sequence representation.

The locus or sequence representation or locus or sequence representation bias can be, for example, 10%, 20%, 30%, 40%, 50%, 60%, 70%, 80%, 90%, 100%, 110%, 120%, 130%, 140%, 150%, 160%, 170%, 180%, 190%, 200%, 225%, 250%, 275%, 300%, 350%, 400%, 450%, 500%, 600%, 700%, 800%, 900%, or 1000% for one, some, or all loci or sequences measured. The locus or sequence representation or locus or sequence representation bias can be, for example, greater than 10%, greater than 20%, greater than 30%, greater than 40%, greater than 50%, greater than 60%, greater than 70%, greater than 80%, greater than 90%, greater than 100%, greater than 110%, greater than 120%, greater than 130%, greater than 140%, greater than 150%, greater than 160%, greater than 170%, greater than 180%, greater than 190%, greater than 200%, greater than 225%, greater than 250%, greater than 275%, greater than 300%, greater than 350%, greater than 400%, greater than 450%, greater than 500%, greater than 600%, greater than 700%, greater than 800%, greater than 900%, or greater than 1000% for one, some, or all loci or sequences measured. The locus or sequence representation or locus or sequence representation bias can be, for example, less than 10%, less than 20%, less than 30%, less than 40%, less than 50%, less than 60%, less than 70%, less than 80%, less than 90%, less than 100%, less than 110%, less than 120%, less than 130%, less than 140%, less than 150%, less than 160%, less than 170%, less than 180%, less than 190%, less than 200%, less than 225%, less than 250%, less than 275%, less than 300%, less than 350%, less than 400%, less than 450%, less than 500%, less than 600%, less than 700%, less than 800%, less than 900%, or less than 1000% for one, some, or all loci or sequences measured.

The locus or sequence representation or locus or sequence representation bias can be, for example, between 10% and 1000%, between 10% and 900%, between 10% and 800%, between 10% and 700%, between 10% and 600%, between 10% and 500%, between 10% and 400%, between 10% and 300%, between 10% and 250%, between 10% and 200%, between 10% and 150%, between 10% and 125%, between 10% and 100%, between 20% and 1000%, between 20% and 900%, between 20% and 800%, between 20% and 700%, between 20% and 600%, between 20% and 500%, between 20% and 400%, between 20% and 300%, between 20% and 250%, between 20% and 200%, between 20% and 150%, between 20% and 125%, between 20% and 100%, between 30% and 1000%, between 30% and 900%, between 30% and 800%, between 30% and 700%, between 30% and 600%, between 30% and 500%, between 30% and 400%, between 30% and 300%, between 30% and 250%, between 30% and 200%, between 30% and 150%, between 30% and 125%, between 30% and 100%, between 40% and 1000%, between 40% and 900%, between 40% and 800%, between 40% and 700%, between 40% and 600%, between 40% and 500%, between 40% and 400%, between 40% and 300%, between 40% and 250%, between 40% and 200%, between 40% and 150%, between 40% and 125%, between 40% and 100%, between 50% and 1000%, between 50% and 900%, between 50% and 800%, between 50% and 700%, between 50% and 600%, between 50% and 500%, between 50% and 400%, between 50% and 300%, between 50% and 250%, between 50% and 200%, between 50% and 150%, between 50% and 125%, between 50% and 100%, between 60% and 1000%, between 60% and 900%, between 60% and 800%, between 60% and 700%, between 60% and 600%, between 60% and 500%, between 60% and 400%, between 60% and 300%, between 60% and 250%, between 60% and 200%, between 60% and 150%, between 60% and 125%, between 60% and 100%, between 70% and 1000%, between 70% and 900%, between 70% and 800%, between 70% and 700%, between 70% and 600%, between 70% and 500%, between 70% and 400%, between 70% and 300%, between 70% and 250%, between 70% and 200%, between 70% and 150%, between 70% and 125%, between 70% and 100%, between 80% and 1000%, between 80% and 900%, between 80% and 800%, between 80% and 700%, between 80% and 600%, between 80% and 500%, between 80% and 400%, between 80% and 300%, between 80% and 250%, between 80% and 200%, between 80% and 150%, between 80% and 125%, between 80% and 100%, between 90% and 1000%, between 90% and 900%, between 90% and 800%, between 90% and 700%, between 90% and 600%, between 90% and 500%, between 90% and 400%, between 90% and 300%, between 90% and 250%, between 90% and 200%, between 90% and 150%, between 90% and 125%, between 90% and 100%, between 100% and 1000%, between 100% and 900%, between 100% and 800%, between 100% and 700%, between 100% and 600%, between 100% and 500%, between 100% and 400%, between 100% and 300%, between 100% and 250%, between 100% and 200%, between 100% and 150%, or between 100% and 125% for one, some, or all loci or sequences measured.

The various locus representations and locus representation biases described above and elsewhere herein can be, for example, for 1 locus, 2 loci, 3 loci, 4 loci, 5 loci, 6 loci, 7 loci, 8 loci, 9 loci, 10 loci, 11 loci, 12 loci, 13 loci, 14 loci, 15 loci, 16 loci, 17 loci, 18 loci, 19 loci, 20 loci, 25 loci, 30 loci, 40 loci, 50 loci, 75 loci, or 100 loci. The locus representation or locus representation bias can be, for example, for at least 1 locus, at least 2 loci, at least 3 loci, at least 4 loci, at least 5 loci, at least 6 loci, at least 7 loci, at least 8 loci, at least 9 loci, at least 10 loci, at least 11 loci, at least 12 loci, at least 13 loci, at least 14 loci, at least 15 loci, at least 16 loci, at least 17 loci, at least 18 loci, at least 19 loci, at least 20 loci, at least 25 loci, at least 30 loci, at least 40 loci, at least 50 loci, at least 75 loci, or at least 100 loci.

The locus representation or locus representation bias can be, for example, for 1 locus, 2 different loci, 3 different loci, 4 different loci, 5 different loci, 6 different loci, 7 different loci, 8 different loci, 9 different loci, 10 different loci, 11 different loci, 12 different loci, 13 different loci, 14 different loci, 15 different loci, 16 different loci, 17 different loci, 18 different loci, 19 different loci, 20 different loci, 25 different loci, 30 different loci, 40 different loci, 50 different loci, 75 different loci, or 100 different loci. The locus representation or locus representation bias can be, for example, for at least 1 locus, at least 2 different loci, at least 3 different loci, at least 4 different loci, at least 5 different loci, at least 6 different loci, at least 7 different loci, at least 8 different loci, at least 9 different loci, at least 10 different loci, at least 11 different loci, at least 12 different loci, at least 13 different loci, at least 14 different loci, at least 15 different loci, at least 16 different loci, at least 17 different loci, at least 18 different loci, at least 19 different loci, at least 20 different loci, at least 25 different loci, at least 30 different loci, at least 40 different loci, at least 50 different loci, at least 75 different loci, or at least 100 different loci.

The various sequence representations and sequence representation biases described above and elsewhere herein can be, for example, for 1 target sequence, 2 target sequences, 3 target sequences, 4 target sequences, 5 target sequences, 6 target sequences, 7 target sequences, 8 target sequences, 9 target sequences, 10 target sequences, 11 target sequences, 12 target sequences, 13 target sequences, 14 target sequences, 15 target sequences, 16 target sequences, 17 target sequences, 18 target sequences, 19 target sequences, 20 target sequences, 25 target sequences, 30 target sequences, 40 target sequences, 50 target sequences, 75 target sequences, or 100 target sequences. The sequence representation or sequence representation bias can be, for example, for at least 1 target sequence, at least 2 target sequences, at least 3 target sequences, at least 4 target sequences, at least 5 target sequences, at least 6 target sequences, at least 7 target sequences, at least 8 target sequences, at least 9 target sequences, at least 10 target sequences, at least 11 target sequences, at least 12 target sequences, at least 13 target sequences, at least 14 target sequences, at least 15 target sequences, at least 16 target sequences, at least 17 target sequences, at least 18 target sequences, at least 19 target sequences, at least 20 target sequences, at least 25 target sequences, at least 30 target sequences, at least 40 target sequences, at least 50 target sequences, at least 75 target sequences, or at least 100 target sequences.

The sequence representation or sequence representation bias can be, for example, for 1 target sequence, 2 different target sequences, 3 different target sequences, 4 different target sequences, 5 different target sequences, 6 different target sequences, 7 different target sequences, 8 different target sequences, 9 different target sequences, 10 different target sequences, 11 different target sequences, 12 different target sequences, 13 different target sequences, 14 different target sequences, 15 different target sequences, 16 different target sequences, 17 different target sequences, 18 different target sequences, 19 different target sequences, 20 different target sequences, 25 different target sequences, 30 different target sequences, 40 different target sequences, 50 different target sequences, 75 different target sequences, or 100 different target sequences. The sequence representation or sequence representation bias can be, for example, for at least 1 target sequence, at least 2 different target sequences, at least 3 different target sequences, at least 4 different target sequences, at least 5 different target sequences, at least 6 different target sequences, at least 7 different target sequences, at least 8 different target sequences, at least 9 different target sequences, at least 10 different target sequences, at least 11 different target sequences, at least 12 different target sequences, at least 13 different target sequences, at least 14 different target sequences, at least 15 different target sequences, at least 16 different target sequences, at least 17 different target sequences, at least 18 different target sequences, at least 19 different target sequences, at least 20 different target sequences, at least 25 different target sequences, at least 30 different target sequences, at least 40 different target sequences, at least 50 different target sequences, at least 75 different target sequences, or at least 100 different target sequences.

Another measure of the quality of the amplified nucleic acids can be the amplification bias in the amplified nucleic acids. Amplification bias is the difference in the level of amplification of different sequences in a nucleic acid sample. A low amplification bias indicates amplified nucleic acids of the highest quality. One expression of amplification bias can be calculated as the ratio (usually expressed as a fold difference or a percent difference) of the locus representation bias of the locus having the highest locus representation bias to the locus representation bias having the lowest locus representation bias in the amplified nucleic acid. Another expression of amplification bias can be calculated as the ratio (usually expressed as a fold difference or a percent difference) of the locus representation of the locus having the highest locus representation to the locus representation having the lowest locus representation in the amplified nucleic acid. If sequence representation bias is measured, then amplification bias can be calculated as the ratio (usually expressed as a fold difference) of the sequence representation bias of the sequence having the highest sequence representation bias to the sequence representation bias having the lowest sequence representation bias in the amplified nucleic acid. Amplification bias can be calculated as the ratio (usually expressed as a fold difference) of the sequence representation of the sequence having the highest sequence representation to the sequence representation having the lowest sequence representation in the amplified nucleic acid. Although the above calculations are measures of amplification bias for all of the loci or sequences assessed, a subset of loci or sequences assessed can be used to calculate amplification bias. In fact, amplification bias can be calculated for individual loci, sequences or alleles. Thus, for example, amplification bias can also be calculated as the ratio (usually expressed as a fold difference or a percent difference) of the locus representation bias of one or more loci to the locus representation bias one or more other loci in the amplified nucleic acid. As another example, amplification bias can also be calculated as the ratio (usually expressed as a fold difference or a percent difference) of the locus representation in an unamplified sample of one or more loci to the locus representation in an amplified sample of the same loci.

The amplification bias can be, for example, 1-fold, 2-fold, 3-fold, 4-fold, 5-fold, 6-fold, 7-fold, 8-fold, 9-fold, 10-fold, 11-fold, 12-fold, 14-fold, 16-fold, 20-fold, 24-fold, 30-fold, 35-fold, 40-fold, 50-fold, 60-fold, 70-fold, 80-fold, 90-fold, 100-fold, 150-fold, 200-fold, 250-fold, or 300-fold. The amplification bias can be, for example, about 1-fold, about 2-fold, about 3-fold, about 4-fold, about 5-fold, about 6-fold, about 7-fold, about 8-fold, about 9-fold, about 10-fold, about 11-fold, about 12-fold, about 14-fold, about 16-fold, about 20-fold, about 24-fold, about 30-fold, about 35-fold, about 40-fold, about 50-fold, about 60-fold, about 70-fold, about 80-fold, about 90-fold, about 100-fold, about 150-fold, about 200-fold, about 250-fold, or about 300-fold. The amplification bias can be, for example, less than 2-fold, less than 3-fold, less than 4-fold, less than 5-fold, less than 6-fold, less than 7-fold, less than 8-fold, less than 9-fold, less than 10-fold, less than 11-fold, less than 12-fold, less than 14-fold, less than 16-fold, less than 20-fold, less than 24-fold, less than 30-fold, less than 35-fold, less than 40-fold, less than 50-fold, less than 60-fold, less than 70-fold, less than 80-fold, less than 90-fold, less than 100-fold, less than 150-fold, less than 200-fold, less than 250-fold, or less than 300-fold.

The amplification bias can be, for example, less than about 2-fold, less than about 3-fold, less than about 4-fold, less than about 5-fold, less than about 6-fold, less than about 7-fold, less than about 8-fold, less than about 9-fold, less than about 10-fold, less than about 11-fold, less than about 12-fold, less than about 14-fold, less than about 16-fold, less than about 20-fold, less than about 24-fold, less than about 30-fold, less than about 35-fold, less than about 40-fold, less than about 50-fold, less than about 60-fold, less than about 70-fold, less than about 80-fold, less than about 90-fold, less than about 100-fold, less than about 150-fold, less than about 200-fold, less than about 250-fold, or less than about 300-fold.

The amplification bias can be, for example, from 1-fold to 300-fold, from 2-fold to 300-fold, from 3-fold to 300-fold, from 4-fold to 300-fold, from 5-fold to 300-fold, from 6-fold to 300-fold, from 7-fold to 300-fold, from 8-fold to 300-fold, from 9-fold to 300-fold, from 10-fold to 300-fold, from 11-fold to 300-fold, from 12-fold to 300-fold, from 14-fold to 300-fold, from 16-fold to 300-fold, from 20-fold to 300-fold, from 24-fold to 300-fold, from 30-fold to 300-fold, from 35-fold to 300-fold, from 40-fold to 300-fold, from 50-fold to 300-fold, from 60-fold to 300-fold, from 70-fold to 300-fold, from 80-fold to 300-fold, from 90-fold to 300-fold, from 100-fold to 300-fold, from 150-fold to 300-fold, from 200-fold to 300-fold, or from 250-fold to 300-fold.

The amplification bias can be, for example, from 1-fold to 250-fold, from 2-fold to 250-fold, from 3-fold to 250-fold, from 4-fold to 250-fold, from 5-fold to 250-fold, from 6-fold to 250-fold, from 7-fold to 250-fold, from 8-fold to 250-fold, from 9-fold to 250-fold, from 10-fold to 250-fold, from 11-fold to 250-fold, from 12-fold to 250-fold, from 14-fold to 250-fold, from 16-fold to 250-fold, from 20-fold to 250-fold, from 24-fold to 250-fold, from 30-fold to 250-fold, from 35-fold to 250-fold, from 40-fold to 250-fold, from 50-fold to 250-fold, from 60-fold to 250-fold, from 70-fold to 250-fold, from 80-fold to 250-fold, from 90-fold to 250-fold, from 100-fold to 250-fold, from 150-fold to 250-fold, or from 200-fold to 250-fold.

The amplification bias can be, for example, from 1-fold to 200-fold, from 2-fold to 200-fold, from 3-fold to 200-fold, from 4-fold to 200-fold, from 5-fold to 200-fold, from 6-fold to 200-fold, from 7-fold to 200-fold, from 8-fold to 200-fold, from 9-fold to 200-fold, from 10-fold to 200-fold, from 11-fold to 200-fold, from 12-fold to 200-fold, from 14-fold to 200-fold, from 16-fold to 200-fold, from 20-fold to 200-fold, from 24-fold to 200-fold, from 30-fold to 200-fold, from 35-fold to 200-fold, from 40-fold to 200-fold, from 50-fold to 200-fold, from 60-fold to 200-fold, from 70-fold to 200-fold, from 80-fold to 200-fold, from 90-fold to 200-fold, from 100-fold to 200-fold, or from 150-fold to 200-fold.

The amplification bias can be, for example, from 1-fold to 150-fold, from 2-fold to 150-fold, from 3-fold to 150-fold, from 4-fold to 150-fold, from 5-fold to 150-fold, from 6-fold to 150-fold, from 7-fold to 150-fold, from 8-fold to 150-fold, from 9-fold to 150-fold, from 10-fold to 150-fold, from 11-fold to 150-fold, from 12-fold to 150-fold, from 14-fold to 150-fold, from 16-fold to 150-fold, from 20-fold to 150-fold, from 24-fold to 150-fold, from 30-fold to 150-fold, from 35-fold to 150-fold, from 40-fold to 150-fold, from 50-fold to 150-fold, from 60-fold to 150-fold, from 70-fold to 150-fold, from 80-fold to 150-fold, from 90-fold to 150-fold, or from 100-fold to 150-fold.

The amplification bias can be, for example, from 1-fold to 100-fold, from 2-fold to 100-fold, from 3-fold to 100-fold, from 4-fold to 100-fold, from 5-fold to 100-fold, from 6-fold to 100-fold, from 7-fold to 100-fold, from 8-fold to 100-fold, from 9-fold to 100-fold, from 10-fold to 100-fold, from 11-fold to 100-fold, from 12-fold to 100-fold, from 14-fold to 100-fold, from 16-fold to 100-fold, from 20-fold to 100-fold, from 24-fold to 100-fold, from 30-fold to 100-fold, from 35-fold to 100-fold, from 40-fold to 100-fold, from 50-fold to 100-fold, from 60-fold to 100-fold, from 70-fold to 100-fold, from 80-fold to 100-fold, or from 90-fold to 100-fold.

The amplification bias can be, for example, from 1-fold to 90-fold, from 2-fold to 90-fold, from 3-fold to 90-fold, from 4-fold to 90-fold, from 5-fold to 90-fold, from 6-fold to 90-fold, from 7-fold to 90-fold, from 8-fold to 90-fold, from 9-fold to 90-fold, from 10-fold to 90-fold, from 11-fold to 90-fold, from 12-fold to 90-fold, from 14-fold to 90-fold, from 16-fold to 90-fold, from 20-fold to 90-fold, from 24-fold to 90-fold, from 30-fold to 90-fold, from 35-fold to 90-fold, from 40-fold to 90-fold, from 50-fold to 90-fold, from 60-fold to 90-fold, from 70-fold to 90-fold, or from 80-fold to 90-fold.

The amplification bias can be, for example, from 1-fold to 80-fold, from 2-fold to 80-fold, from 3-fold to 80-fold, from 4-fold to 80-fold, from 5-fold to 80-fold, from 6-fold to 80-fold, from 7-fold to 80-fold, from 8-fold to 80-fold, from 9-fold to 80-fold, from 10-fold to 80-fold, from 11-fold to 80-fold, from 12-fold to 80-fold, from 14-fold to 80-fold, from 16-fold to 80-fold, from 20-fold to 80-fold, from 24-fold to 80-fold, from 30-fold to 80-fold, from 35-fold to 80-fold, from 40-fold to 80-fold, from 50-fold to 80-fold, from 60-fold to 80-fold, or from 70-fold to 80-fold.

The amplification bias can be, for example, from 1-fold to 70-fold, from 2-fold to 70-fold, from 3-fold to 70-fold, from 4-fold to 70-fold, from 5-fold to 70-fold, from 6-fold to 70-fold, from 7-fold to 70-fold, from 8-fold to 70-fold, from 9-fold to 70-fold, from 10-fold to 70-fold, from 11-fold to 70-fold, from 12-fold to 70-fold, from 14-fold to 70-fold, from 16-fold to 70-fold, from 20-fold to 70-fold, from 24-fold to 70-fold, from 30-fold to 70-fold, from 35-fold to 70-fold, from 40-fold to 70-fold, from 50-fold to 70-fold, or from 60-fold to 70-fold. The amplification bias can be, for example, from 1-fold to 60-fold, from 2-fold to 60-fold, from 3-fold to 60-fold, from 4-fold to 60-fold, from 5-fold to 60-fold, from 6-fold to 60-fold, from 7-fold to 60-fold, from 8-fold to 60-fold, from 9-fold to 60-fold, from 10-fold to 60-fold, from 11-fold to 60-fold, from 12-fold to 60-fold, from 14-fold to 60-fold, from 16-fold to 60-fold, from 20-fold to 60-fold, from 24-fold to 60-fold, from 30-fold to 60-fold, from 35-fold to 60-fold, from 40-fold to 60-fold, or from 50-fold to 60-fold.

The amplification bias can be, for example, from 1-fold to 50-fold, from 2-fold to 50-fold, from 3-fold to 50-fold, from 4-fold to 50-fold, from 5-fold to 50-fold, from 6-fold to 50-fold, from 7-fold to 50-fold, from 8-fold to 50-fold, from 9-fold to 50-fold, from 10-fold to 50-fold, from 11-fold to 50-fold, from 12-fold to 50-fold, from 14-fold to 50-fold, from 16-fold to 50-fold, from 20-fold to 50-fold, from 24-fold to 50-fold, from 30-fold to 50-fold, from 35-fold to 50-fold, or from 40-fold to 50-fold. The amplification bias can be, for example, from 1-fold to 40-fold, from 2-fold to 40-fold, from 3-fold to 40-fold, from 4-fold to 40-fold, from 5-fold to 40-fold, from 6-fold to 40-fold, from 7-fold to 40-fold, from 8-fold to 40-fold, from 9-fold to 40-fold, from 10-fold to 40-fold, from 11-fold to 40-fold, from 12-fold to 40-fold, from 14-fold to 40-fold, from 16-fold to 40-fold, from 20-fold to 40-fold, from 24-fold to 40-fold, from 30-fold to 40-fold, or from 35-fold to 40-fold.

The amplification bias can be, for example, from 1-fold to 30-fold, from 2-fold to 30-fold, from 3-fold to 30-fold, from 4-fold to 30-fold, from 5-fold to 30-fold, from 6-fold to 30-fold, from 7-fold to 30-fold, from 8-fold to 30-fold, from 9-fold to 30-fold, from 10-fold to 30-fold, from 11-fold to 30-fold, from 12-fold to 30-fold, from 14-fold to 30-fold, from 16-fold to 30-fold, from 20-fold to 30-fold, or from 24-fold to 30-fold. The amplification bias can be, for example, from 1-fold to 20-fold, from 2-fold to 20-fold, from 3-fold to 20-fold, from 4-fold to 20-fold, from 5-fold to 20-fold, from 6-fold to 20-fold, from 7-fold to 20-fold, from 8-fold to 20-fold, from 9-fold to 20-fold, from 10-fold to 20-fold, from 11-fold to 20-fold, from 12-fold to 20-fold, from 14-fold to 20-fold, from 16-fold to 20-fold, from 20-fold to 20-fold, or from 24-fold to 20-fold.

The amplification bias can be, for example, from 1-fold to 12-fold, from 2-fold to 12-fold, from 3-fold to 12-fold, from 4-fold to 12-fold, from 5-fold to 12-fold, from 6-fold to 12-fold, from 7-fold to 12-fold, from 8-fold to 12-fold, from 9-fold to 12-fold, from 10-fold to 12-fold, or from 11-fold to 12-fold. The amplification bias can be, for example, from 1-fold to 11-fold, from 2-fold to 11-fold, from 3-fold to 11-fold, from 4-fold to 11-fold, from 5-fold to 11-fold, from 6-fold to 11-fold, from 7-fold to 11-fold, from 8-fold to 11-fold, from 9-fold to 11-fold, or from 10-fold to 11-fold. The amplification bias can be, for example, from 1-fold to 10-fold, from 2-fold to 10-fold, from 3-fold to 10-fold, from 4-fold to 10-fold, from 5-fold to 10-fold, from 6-fold to 10-fold, from 7-fold to 10-fold, from 8-fold to 10-fold, or from 9-fold to 10-fold. The amplification bias can be, for example, from 1-fold to 9-fold, from 2-fold to 9-fold, from 3-fold to 9-fold, from 4-fold to 9-fold, from 5-fold to 9-fold, from 6-fold to 9-fold, from 7-fold to 9-fold, or from 8-fold to 9-fold.

The amplification bias can be, for example, from 1-fold to 8-fold, from 2-fold to 8-fold, from 3-fold to 8-fold, from 4-fold to 8-fold, from 5-fold to 8-fold, from 6-fold to 8-fold, or from 7-fold to 8-fold. The amplification bias can be, for example, from 1-fold to 7-fold, from 2-fold to 7-fold, from 3-fold to 7-fold, from 4-fold to 7-fold, from 5-fold to 7-fold, or from 6-fold to 7-fold. The amplification bias can be, for example, from 1-fold to 6-fold, from 2-fold to 6-fold, from 3-fold to 6-fold, from 4-fold to 6-fold, or from 5-fold to 6-fold. The amplification bias can be, for example, from 1-fold to 5-fold, from 2-fold to 5-fold, from 3-fold to 5-fold, from 4-fold to 5-fold, from 1-fold to 4-fold, from 2-fold to 4-fold, from 3-fold to 4-fold, from 1-fold to 3-fold, from 2-fold to 3-fold, or from 1-fold to 2-fold.

The amplification bias can be, for example, from about 1-fold to about 300-fold, from about 2-fold to about 300-fold, from about 3-fold to about 300-fold, from about 4-fold to about 300-fold, from about 5-fold to about 300-fold, from about 6-fold to about 300-fold, from about 7-fold to about 300-fold, from about 8-fold to about 300-fold, from about 9-fold to about 300-fold, from about 10-fold to about 300-fold, from about 11-fold to about 300-fold, from about 12-fold to about 300-fold, from about 14-fold to about 300-fold, from about 16-fold to about 300-fold, from about 20-fold to about 300-fold, from about 24-fold to about 300-fold, from about 30-fold to about 300-fold, from about 35-fold to about 300-fold, from about 40-fold to about 300-fold, from about 50-fold to about 300-fold, from about 60-fold to about 300-fold, from about 70-fold to about 300-fold, from about 80-fold to about 300-fold, from about 90-fold to about 300-fold, from about 100-fold to about 300-fold, from about 150-fold to about 300-fold, from about 200-fold to about 300-fold, or from about 250-fold to about 300-fold.

The amplification bias can be, for example, from about 1-fold to about 250-fold, from about 2-fold to about 250-fold, from about 3-fold to about 250-fold, from about 4-fold to about 250-fold, from about 5-fold to about 250-fold, from about 6-fold to about 250-fold, from about 7-fold to about 250-fold, from about 8-fold to about 250-fold, from about 9-fold to about 250-fold, from about 10-fold to about 250-fold, from about 11-fold to about 250-fold, from about 12-fold to about 250-fold, from about 14-fold to about 250-fold, from about 16-fold to about 250-fold, from about 20-fold to about 250-fold, from about 24-fold to about 250-fold, from about 30-fold to about 250-fold, from about 35-fold to about 250-fold, from about 40-fold to about 250-fold, from about 50-fold to about 250-fold, from about 60-fold to about 250-fold, from about 70-fold to about 250-fold, from about 80-fold to about 250-fold, from about 90-fold to about 250-fold, from about 100-fold to about 250-fold, from about 150-fold to about 250-fold, or from about 200-fold to about 250-fold.

The amplification bias can be, for example, from about 1-fold to about 200-fold, from about 2-fold to about 200-fold, from about 3-fold to about 200-fold, from about 4-fold to about 200-fold, from about 5-fold to about 200-fold, from about 6-fold to about 200-fold, from about 7-fold to about 200-fold, from about 8-fold to about 200-fold, from about 9-fold to about 200-fold, from about 10-fold to about 200-fold, from about 11-fold to about 200-fold, from about 12-fold to about 200-fold, from about 14-fold to about 200-fold, from about 16-fold to about 200-fold, from about 20-fold to about 200-fold, from about 24-fold to about 200-fold, from about 30-fold to about 200-fold, from about 35-fold to about 200-fold, from about 40-fold to about 200-fold, from about 50-fold to about 200-fold, from about 60-fold to about 200-fold, from about 70-fold to about 200-fold, from about 80-fold to about 200-fold, from about 90-fold to about 200-fold, from about 100-fold to about 200-fold, or from about 150-fold to about 200-fold.

The amplification bias can be, for example, from about 1-fold to about 150-fold, from about 2-fold to about 150-fold, from about 3-fold to about 150-fold, from about 4-fold to about 150-fold, from about 5-fold to about 150-fold, from about 6-fold to about 150-fold, from about 7-fold to about 150-fold, from about 8-fold to about 150-fold, from about 9-fold to about 150-fold, from about 10-fold to about 150-fold, from about 11-fold to about 150-fold, from about 12-fold to about 150-fold, from about 14-fold to about 150-fold, from about 16-fold to about 150-fold, from about 20-fold to about 150-fold, from about 24-fold to about 150-fold, from about 30-fold to about 150-fold, from about 35-fold to about 150-fold, from about 40-fold to about 150-fold, from about 50-fold to about 150-fold, from about 60-fold to about 150-fold, from about 70-fold to about 150-fold, from about 80-fold to about 150-fold, from about 90-fold to about 150-fold, or from about 100-fold to about 150-fold.

The amplification bias can be, for example, from about 1-fold to about 100-fold, from about 2-fold to about 100-fold, from about 3-fold to about 100-fold, from about 4-fold to about 100-fold, from about 5-fold to about 100-fold, from about 6-fold to about 100-fold, from about 7-fold to about 100-fold, from about 8-fold to about 100-fold, from about 9-fold to about 100-fold, from about 10-fold to about 100-fold, from about 11-fold to about 100-fold, from about 12-fold to about 100-fold, from about 14-fold to about 100-fold, from about 16-fold to about 100-fold, from about 20-fold to about 100-fold, from about 24-fold to about 100-fold, from about 30-fold to about 100-fold, from about 35-fold to about 100-fold, from about 40-fold to about 100-fold, from about 50-fold to about 100-fold, from about 60-fold to about 100-fold, from about 70-fold to about 100-fold, from about 80-fold to about 100-fold, or from about 90-fold to about 100-fold.

The amplification bias can be, for example, from about 1-fold to about 90-fold, from about 2-fold to about 90-fold, from about 3-fold to about 90-fold, from about 4-fold to about 90-fold, from about 5-fold to about 90-fold, from about 6-fold to about 90-fold, from about 7-fold to about 90-fold, from about 8-fold to about 90-fold, from about 9-fold to about 90-fold, from about 10-fold to about 90-fold, from about 11-fold to about 90-fold, from about 12-fold to about 90-fold, from about 14-fold to about 90-fold, from about 16-fold to about 90-fold, from about 20-fold to about 90-fold, from about 24-fold to about 90-fold, from about 30-fold to about 90-fold, from about 35-fold to about 90-fold, from about 40-fold to about 90-fold, from about 50-fold to about 90-fold, from about 60-fold to about 90-fold, from about 70-fold to about 90-fold, or from about 80-fold to about 90-fold.

The amplification bias can be, for example, from about 1-fold to about 80-fold, from about 2-fold to about 80-fold, from about 3-fold to about 80-fold, from about 4-fold to about 80-fold, from about 5-fold to about 80-fold, from about 6-fold to about 80-fold, from about 7-fold to about 80-fold, from about 8-fold to about 80-fold, from about 9-fold to about 80-fold, from about 10-fold to about 80-fold, from about 11-fold to about 80-fold, from about 12-fold to about 80-fold, from about 14-fold to about 80-fold, from about 16-fold to about 80-fold, from about 20-fold to about 80-fold, from about 24-fold to about 80-fold, from about 30-fold to about 80-fold, from about 35-fold to about 80-fold, from about 40-fold to about 80-fold, from about 50-fold to about 80-fold, from about 60-fold to about 80-fold, or from about 70-fold to about 80-fold.

The amplification bias can be, for example, from about 1-fold to about 70-fold, from about 2-fold to about 70-fold, from about 3-fold to about 70-fold, from about 4-fold to about 70-fold, from about 5-fold to about 70-fold, from about 6-fold to about 70-fold, from about 7-fold to about 70-fold, from about 8-fold to about 70-fold, from about 9-fold to about 70-fold, from about 10-fold to about 70-fold, from about 11-fold to about 70-fold, from about 12-fold to about 70-fold, from about 14-fold to about 70-fold, from about 16-fold to about 70-fold, from about 20-fold to about 70-fold, from about 24-fold to about 70-fold, from about 30-fold to about 70-fold, from about 35-fold to about 70-fold, from about 40-fold to about 70-fold, from about 50-fold to about 70-fold, or from about 60-fold to about 70-fold. The amplification bias can be, for example, from about 1-fold to about 60-fold, from about 2-fold to about 60-fold, from about 3-fold to about 60-fold, from about 4-fold to about 60-fold, from about 5-fold to about 60-fold, from about 6-fold to about 60-fold, from about 7-fold to about 60-fold, from about 8-fold to about 60-fold, from about 9-fold to about 60-fold, from about 10-fold to about 60-fold, from about 11-fold to about 60-fold, from about 12-fold to about 60-fold, from about 14-fold to about 60-fold, from about 16-fold to about 60-fold, from about 20-fold to about 60-fold, from about 24-fold to about 60-fold, from about 30-fold to about 60-fold, from about 35-fold to about 60-fold, from about 40-fold to about 60-fold, or from about 50-fold to about 60-fold.

The amplification bias can be, for example, from about 1-fold to about 50-fold, from about 2-fold to about 50-fold, from about 3-fold to about 50-fold, from about 4-fold to about 50-fold, from about 5-fold to about 50-fold, from about 6-fold to about 50-fold, from about 7-fold to about 50-fold, from about 8-fold to about 50-fold, from about 9-fold to about 50-fold, from about 10-fold to about 50-fold, from about 11-fold to about 50-fold, from about 12-fold to about 50-fold, from about 14-fold to about 50-fold, from about 16-fold to about 50-fold, from about 20-fold to about 50-fold, from about 24-fold to about 50-fold, from about 30-fold to about 50-fold, from about 35-fold to about 50-fold, or from about 40-fold to about 50-fold. The amplification bias can be, for example, from about 1-fold to about 40-fold, from about 2-fold to about 40-fold, from about 3-fold to about 40-fold, from about 4-fold to about 40-fold, from about 5-fold to about 40-fold, from about 6-fold to about 40-fold, from about 7-fold to about 40-fold, from about 8-fold to about 40-fold, from about 9-fold to about 40-fold, from about 10-fold to about 40-fold, from about 11-fold to about 40-fold, from about 12-fold to about 40-fold, from about 14-fold to about 40-fold, from about 16-fold to about 40-fold, from about 20-fold to about 40-fold, from about 24-fold to about 40-fold, from about 30-fold to about 40-fold, or from about 35-fold to about 40-fold.

The amplification bias can be, for example, from about 1-fold to about 30-fold, from about 2-fold to about 30-fold, from about 3-fold to about 30-fold, from about 4-fold to about 30-fold, from about 5-fold to about 30-fold, from about 6-fold to about 30-fold, from about 7-fold to about 30-fold, from about 8-fold to about 30-fold, from about 9-fold to about 30-fold, from about 10-fold to about 30-fold, from about 11-fold to about 30-fold, from about 12-fold to about 30-fold, from about 14-fold to about 30-fold, from about 16-fold to about 30-fold, from about 20-fold to about 30-fold, or from about 24-fold to about 30-fold. The amplification bias can be, for example, from about 1-fold to about 20-fold, from about 2-fold to about 20-fold, from about 3-fold to about 20-fold, from about 4-fold to about 20-fold, from about 5-fold to about 20-fold, from about 6-fold to about 20-fold, from about 7-fold to about 20-fold, from about 8-fold to about 20-fold, from about 9-fold to about 20-fold, from about 10-fold to about 20-fold, from about 11-fold to about 20-fold, from about 12-fold to about 20-fold, from about 14-fold to about 20-fold, from about 16-fold to about 20-fold, from about 20-fold to about 20-fold, or from about 24-fold to about 20-fold.

The amplification bias can be, for example, from about 1-fold to about 12-fold, from about 2-fold to about 12-fold, from about 3-fold to about 12-fold, from about 4-fold to about 12-fold, from about 5-fold to about 12-fold, from about 6-fold to about 12-fold, from about 7-fold to about 12-fold, from about 8-fold to about 12-fold, from about 9-fold to about 12-fold, from about 10-fold to about 12-fold, or from about 11-fold to about 12-fold. The amplification bias can be, for example, from about 1-fold to about 11-fold, from about 2-fold to about 11-fold, from about 3-fold to about 11-fold, from about 4-fold to about 11-fold, from about 5-fold to about 11-fold, from about 6-fold to about 11-fold, from about 7-fold to about 11-fold, from about 8-fold to about 11-fold, from about 9-fold to about 11-fold, or from about 10-fold to about 11-fold. The amplification bias can be, for example, from about 1-fold to about 10-fold, from about 2-fold to about 10-fold, from about 3-fold to about 10-fold, from about 4-fold to about 10-fold, from about 5-fold to about 10-fold, from about 6-fold to about 10-fold, from about 7-fold to about 10-fold, from about 8-fold to about 10-fold, or from about 9-fold to about 10-fold. The amplification bias can be, for example, from about 1-fold to about 9-fold, from about 2-fold to about 9-fold, from about 3-fold to about 9-fold, from about 4-fold to about 9-fold, from about 5-fold to about 9-fold, from about 6-fold to about 9-fold, from about 7-fold to about 9-fold, or from about 8-fold to about 9-fold.

The amplification bias can be, for example, from about 1-fold to about 8-fold, from about 2-fold to about 8-fold, from about 3-fold to about 8-fold, from about 4-fold to about 8-fold, from about 5-fold to about 8-fold, from about 6-fold to about 8-fold, or from about 7-fold to about 8-fold. The amplification bias can be, for example, from about 1-fold to about 7-fold, from about 2-fold to about 7-fold, from about 3-fold to about 7-fold, from about 4-fold to about 7-fold, from about 5-fold to about 7-fold, or from about 6-fold to about 7-fold. The amplification bias can be, for example, from about 1-fold to about 6-fold, from about 2-fold to about 6-fold, from about 3-fold to about 6-fold, from about 4-fold to about 6-fold, or from about 5-fold to about 6-fold. The amplification bias can be, for example, from about 1-fold to about 5-fold, from about 2-fold to about 5-fold, from about 3-fold to about 5-fold, from about 4-fold to about 5-fold, from about 1-fold to about 4-fold, from about 2-fold to about 4-fold, from about 3-fold to about 4-fold, from about 1-fold to about 3-fold, from about 2-fold to about 3-fold, or from about 1-fold to about 2-fold.

The various amplification biases described above and elsewhere herein can be, for example, for 1 locus, 2 loci, 3 loci, 4 loci, 5 loci, 6 loci, 7 loci, 8 loci, 9 loci, 10 loci, 11 loci, 12 loci, 13 loci, 14 loci, 15 loci, 16 loci, 17 loci, 18 loci, 19 loci, 20 loci, 25 loci, 30 loci, 40 loci, 50 loci, 75 loci, or 100 loci. The amplification bias can be, for example, for at least 1 locus, at least 2 loci, at least 3 loci, at least 4 loci, at least 5 loci, at least 6 loci, at least 7 loci, at least 8 loci, at least 9 loci, at least 10 loci, at least 11 loci, at least 12 loci, at least 13 loci, at least 14 loci, at least 15 loci, at least 16 loci, at least 17 loci, at least 18 loci, at least 19 loci, at least 20 loci, at least 25 loci, at least 30 loci, at least 40 loci, at least 50 loci, at least 75 loci, or at least 100 loci.

The amplification bias can be, for example, for 1 locus, 2 different loci, 3 different loci, 4 different loci, 5 different loci, 6 different loci, 7 different loci, 8 different loci, 9 different loci, 10 different loci, 11 different loci, 12 different loci, 13 different loci, 14 different loci, 15 different loci, 16 different loci, 17 different loci, 18 different loci, 19 different loci, 20 different loci, 25 different loci, 30 different loci, 40 different loci, 50 different loci, 75 different loci, or 100 different loci. The amplification bias can be, for example, for at least 1 locus, at least 2 different loci, at least 3 different loci, at least 4 different loci, at least 5 different loci, at least 6 different loci, at least 7 different loci, at least 8 different loci, at least 9 different loci, at least 10 different loci, at least 11 different loci, at least 12 different loci, at least 13 different loci, at least 14 different loci, at least 15 different loci, at least 16 different loci, at least 17 different loci, at least 18 different loci, at least 19 different loci, at least 20 different loci, at least 25 different loci, at least 30 different loci, at least 40 different loci, at least 50 different loci, at least 75 different loci, or at least 100 different loci.

The various amplification biases described above and elsewhere herein can be, for example, for 1 target sequence, 2 target sequences, 3 target sequences, 4 target sequences, 5 target sequences, 6 target sequences, 7 target sequences, 8 target sequences, 9 target sequences, 10 target sequences, 11 target sequences, 12 target sequences, 13 target sequences, 14 target sequences, 15 target sequences, 16 target sequences, 17 target sequences, 18 target sequences, 19 target sequences, 20 target sequences, 25 target sequences, 30 target sequences, 40 target sequences, 50 target sequences, 75 target sequences, or 100 target sequences. The amplification bias can be, for example, for at least 1 target sequence, at least 2 target sequences, at least 3 target sequences, at least 4 target sequences, at least 5 target sequences, at least 6 target sequences, at least 7 target sequences, at least 8 target sequences, at least 9 target sequences, at least 10 target sequences, at least 11 target sequences, at least 12 target sequences, at least 13 target sequences, at least 14 target sequences, at least 15 target sequences, at least 16 target sequences, at least 17 target sequences, at least 18 target sequences, at least 19 target sequences, at least 20 target sequences, at least 25 target sequences, at least 30 target sequences, at least 40 target sequences, at least 50 target sequences, at least 75 target sequences, or at least 100 target sequences.

The amplification bias can be, for example, for 1 target sequence, 2 different target sequences, 3 different target sequences, 4 different target sequences, 5 different target sequences, 6 different target sequences, 7 different target sequences, 8 different target sequences, 9 different target sequences, 10 different target sequences, 11 different target sequences, 12 different target sequences, 13 different target sequences, 14 different target sequences, 15 different target sequences, 16 different target sequences, 17 different target sequences, 18 different target sequences, 19 different target sequences, 20 different target sequences, 25 different target sequences, 30 different target sequences, 40 different target sequences, 50 different target sequences, 75 different target sequences, or 100 different target sequences. The amplification bias can be, for example, for at least 1 target sequence, at least 2 different target sequences, at least 3 different target sequences, at least 4 different target sequences, at least 5 different target sequences, at least 6 different target sequences, at least 7 different target sequences, at least 8 different target sequences, at least 9 different target sequences, at least 10 different target sequences, at least 11 different target sequences, at least 12 different target sequences, at least 13 different target sequences, at least 14 different target sequences, at least 15 different target sequences, at least 16 different target sequences, at least 17 different target sequences, at least 18 different target sequences, at least 19 different target sequences, at least 20 different target sequences, at least 25 different target sequences, at least 30 different target sequences, at least 40 different target sequences, at least 50 different target sequences, at least 75 different target sequences, or at least 100 different target sequences.

D. Modifications And Additional Operations

1. Detection of Amplification Products

Amplification products can be detected directly by, for example, primary labeling or secondary labeling, as described below.

i. Primary Labeling

Primary labeling consists of incorporating labeled moieties, such as fluorescent nucleotides, biotinylated nucleotides, digoxygenin-containing nucleotides, or bromodeoxyuridine, during strand displacement replication. For example, one may incorporate cyanine dye deoxyuridine analogs (Yu et al., *Nucleic Acids Res.*, 22:3226-3232 (1994)) at a frequency of 4 analogs for every 100 nucleotides. A preferred method for detecting nucleic acid amplified in situ is to label the DNA during amplification with BrdUrd, followed by binding of the incorporated BrdU with a biotinylated anti-BrdU antibody (Zymed Labs, San Francisco, Calif.), followed by binding of the biotin moieties with Streptavidin-Peroxidase (Life Sciences, Inc.), and finally development of fluorescence with Fluorescein-tyramide (DuPont de Nemours & Co., Medical Products Dept.). Other methods for detecting nucleic acid amplified in situ include labeling the DNA during amplification with 5-methylcytosine, followed by binding of the incorporated 5-methylcytosine with an antibody (Sano et al., *Biochim. Biophys. Acta* 951:157-165 (1988)), or labeling the DNA during amplification with aminoallyl-deoxyuridine, followed by binding of the incorporated aminoallyl-deoxyuridine with an Oregon Green® dye (Molecular Probes, Eugene, Oreg.) (Henegariu et al., *Nature Biotechnology* 18:345-348 (2000)).

Another method of labeling amplified nucleic acids is to incorporate 5-(3-aminoallyl)-dUTP (AAdUTP) in the nucleic acid during amplification followed by chemical labeling at the incorporated nucleotides. Incorporated 5-(3-aminoallyl)-deoxyuridine (AAdU) can be coupled to labels that have reactive groups that are capable of reacting with amine groups. AAdUTP can be prepared according to Langer et al. (1981). Proc. Natl. Acad. Sci. USA. 78: 6633-37. Other modified nucleotides can be used in analogous ways. That is, other modified nucleotides with minimal modification can be incorporated during replication and labeled after incorporation.

Examples of labels suitable for addition to AAdUTP are radioactive isotopes, fluorescent molecules, phosphorescent molecules, enzymes, antibodies, and ligands. Examples of suitable fluorescent labels include fluorescein isothiocyanate (FITC), 5,6-carboxymethyl fluorescein, Texas red, nitrobenz-2-oxa-1,3-diazol-4-yl (NBD), coumarin, dansyl chloride, rhodamine, amino-methyl coumarin (AMCA), Eosin, Erythrosin, BODIPY®, Cascade Blue®, Oregon Green®, pyrene, lissamine, xanthenes, acridines, oxazines, phycoerythrin, macrocyclic chelates of lanthanide ions such as quantum Dye™, fluorescent energy transfer dyes, such as thiazole orange-ethidium heterodimer, and the cyanine dyes Cy3, Cy3.5, Cy5, Cy5.5 and Cy7. Examples of other specific fluorescent labels include 3-Hydroxypyrene 5,8,10-Tri Sulfonic acid, 5-Hydroxy Tryptamine (5-HT), Acid Fuchsin, Alizarin Complexon, Alizarin Red, Allophycocyanin, Aminocoumarin, Anthroyl Stearate, Astrazon Brilliant Red 4G, Astrazon Orange R, Astrazon Red 6B, Astrazon Yellow 7 GLL, Atabrine, Auramine, Aurophosphine, Aurophosphine G, BAO 9 (Bisaminophenyloxadiazole), BCECF, Berberine Sulphate, Bisbenzamide, Blancophor FFG Solution, Blancophor SV, Bodipy F1, Brilliant Sulphoflavin FF, Calcien Blue, Calcium Green, Calcofluor RW Solution, Calcofluor White, Calcophor White ABT Solution, Calcophor White Standard Solution, Carbostyryl, Cascade Yellow, Catecholamine, Chinacrine, Coriphosphine O, Coumarin-Phalloidin, CY3.1 8, CY5.1 8, CY7, Dans (1-Dimethyl Amino Naphaline 5 Sulphonic Acid), Dansa (Diamino Naphtyl Sulphonic Acid), Dansyl NH—CH3, Diamino Phenyl Oxydiazole (DAO), Dimethylamino-5-Sulphonic acid, Dipyrromethenboron Difluoride, Diphenyl Brilliant Flavine 7GFF, Dopamine, Erythrosin ITC, Euchrysin, FIF (Formaldehyde Induced Fluorescence), Flazo Orange, Fluo 3, Fluorescamine, Fura-2, Genacryl Brilliant Red B, Genacryl Brilliant Yellow 10GF, Genacryl Pink 3G, Genacryl Yellow 5GF, Gloxalic Acid, Granular Blue, Haematoporphyrin, Indo-1, Intrawhite Cf Liquid, Leucophor PAF, Leucophor SF, Leucophor WS, Lissamine Rhodamine B200 (RD200), Lucifer Yellow CH, Lucifer Yellow VS, Magdala Red, Marina Blue, Maxilon Brilliant Flavin 10 GFF, Maxilon Brilliant Flavin 8 GFF, MPS (Methyl Green Pyronine Stilbene), Mithramycin, NBD Amine, Nitrobenzoxadidole, Noradrenaline, Nuclear Fast Red, Nuclear Yellow, Nylosan Brilliant Flavin E8G, Oxadiazole, Pacific Blue, Pararosaniline (Feulgen), Phorwite AR Solution, Phorwite BKL, Phorwite Rev, Phorwite RPA, Phosphine 3R, Phthalocyanine, Phycoerythrin R, Polyazaindacene Pontochrome Blue Black, Porphyrin, Primuline, Procion Yellow, Pyronine, Pyronine B, Pyrozal Brilliant Flavin 7GF, Quinacrine Mustard, Rhodamine 123, Rhodamine 5 GLD, Rhodamine 6G, Rhodamine B, Rhodamine B 200, Rhodamine B Extra, Rhodamine BB, Rhodamine BG, Rhodamine WT, Serotonin, Sevron Brilliant Red 2B, Sevron Brilliant Red 4G, Sevron Brilliant Red B, Sevron Orange, Sevron Yellow L, SITS (Primuline), SITS (Stilbene Isothiosulphonic acid), Stilbene, Snarf 1, sulpho Rhodamine B Can C, Sulpho Rhodamine G Extra, Tetracycline, Thiazine Red R, Thioflavin S, Thioflavin TCN, Thioflavin 5, Thiolyte, Thiozol Orange, Tinopol CBS, True Blue, Ultralite, Uranine B, Uvitex SFC, Xylene Orange, and XRITC.

Preferred fluorescent labels are fluorescein (5-carboxyfluorescein-N-hydroxysuccinimide ester), rhodamine (5,6-tetramethyl rhodamine), and the cyanine dyes Cy3, Cy3.5, Cy5, Cy5.5 and Cy7. The absorption and emission maxima, respectively, for these fluors are: FITC (490 nm; 520 nm), Cy3 (554 nm; 568 nm), Cy3.5 (581 nm; 588 nm), Cy5 (652 nm: 672 nm), Cy5.5 (682 nm; 703 nm) and Cy7 (755 nm; 778 nm), thus allowing their simultaneous detection. Other examples of fluorescein dyes include 6-carboxyfluorescein (6-FAM), 2',4',1,4,-tetrachlorofluorescein (TET), 2',4',5',7',1,4-hexachlorofluorescein (HEX), 2',7'-dimethoxy-4',5'-dichloro-6-carboxyrhodamine (JOE), 2'-chloro-5'-fluoro-7', 8'-fused phenyl-1,4-dichloro-6-carboxyfluorescein (NED), and 2'-chloro-7'-phenyl-1,4-dichloro-6-carboxyfluorescein (VIC). Fluorescent labels can be obtained from a variety of commercial sources, including Amersham Pharmacia Biotech, Piscataway, N.J.; Molecular Probes, Eugene, Oreg.; and Research Organics, Cleveland, Ohio.

ii. Secondary Labeling with Detection Probes

Secondary labeling consists of using suitable molecular probes, referred to as detection probes, to detect the amplified nucleic acids. For example, a primer may be designed to contain, in its non-complementary portion, a known arbitrary sequence, referred to as a detection tag. A secondary hybridization step can be used to bind detection probes to these detection tags. The detection probes may be labeled as described above with, for example, an enzyme, fluorescent moieties, or radioactive isotopes. By using three detection tags per primer, and four fluorescent moieties per each detection probe, one may obtain a total of twelve fluorescent signals for every replicated strand.

iii. Multiplexing and Hybridization Array Detection

Detection of amplified nucleic acids can be multiplexed by using sets of different primers, each set designed for amplifying different target sequences. Only those primers that are able to find their targets will give rise to amplified products. There are two alternatives for capturing a given amplified nucleic acid to a fixed position in a solid-state detector. One is to include within the non-complementary portion of the primers a unique address tag sequence for each unique set of primers. Nucleic acid amplified using a given set of primers will then contain sequences corresponding to a specific address tag sequence. A second and preferred alternative is to use a sequence present in the target sequence as an address tag.

iv. Enzyme-Linked Detection

Amplified nucleic acid labeled by incorporation of labeled nucleotides can be detected with established enzyme-linked detection systems. For example, amplified nucleic acid labeled by incorporation of biotin using biotin-16-UTP (Roche Molecular Biochemicals) can be detected as follows. The nucleic acid is immobilized on a solid glass surface by hybridization with a complementary DNA oligonucleotide (address probe) complementary to the target sequence (or its complement) present in the amplified nucleic acid. After hybridization, the glass slide is washed and contacted with alkaline phosphatase-streptavidin conjugate (Tropix, Inc., Bedford, Mass.). This enzyme-streptavidin conjugate binds to the biotin moieties on the amplified nucleic acid. The slide is again washed to remove excess enzyme conjugate and the chemiluminescent substrate CSPD (Tropix, Inc.) is added and covered with a glass cover slip. The slide can then be imaged in a Biorad Fluorimager.

2. Using Products of Multiple Displacement Amplification

The nucleic acids produced using the disclosed method can be used for any purpose. For example, the amplified nucleic acids can be analyzed (such as by sequencing or probe hybridization) to determine characteristics of the amplified sequences or the presence or absence or certain sequences. The amplified nucleic acids can also be used as reagents for assays or other methods. For example, nucleic acids produced in the disclosed method can be coupled or adhered to a solid-state substrate. The resulting immobilized nucleic acids can be used as probes or indexes of sequences in a sample. Nucleic acids produced in the disclosed method can be coupled or adhered to a solid-state substrate in any suitable way. For example, nucleic acids generated by multiple strand displacement can be attached by adding modified nucleotides to the 3' ends of nucleic acids produced by strand displacement replication using terminal deoxynucleotidyl transferase, and reacting the modified nucleotides with a solid-state substrate or support thereby attaching the nucleic acids to the solid-state substrate or support.

Nucleic acids produced in the disclosed method also can be used as probes or hybridization partners. For example, sequences of interest can be amplified in the disclosed method and provide a ready source of probes. The replicated strands (produced in the disclosed method) can be cleaved prior to use as hybridization probes. For example, the replicated strands can be cleaved with DNAse I. The hybridization probes can be labeled as described elsewhere herein with respect to labeling of nucleic acids produce in the disclosed method.

Nucleic acids produced in the disclosed method also can be used for subtractive hybridization to identify sequences that are present in only one of a pair or set of samples. For example, amplified cDNA from different samples can be annealed and the resulting double-stranded material can be separated from single-stranded material. Unhybridized sequences would be indicative of sequences expressed in one of the samples but not others.

SPECIFIC EMBODIMENTS

Disclosed is a method of amplifying nucleic acids, the method comprising incubating nucleic acids comprising target sequences at an elevated temperature in the presence of a thermolabile nucleic acid polymerase having strand displacement activity, an additive, and a set of primers, under conditions promoting replication of the nucleic acids. Replication of the nucleic acids results in replicated strands. During replication at least one of the replicated nucleic acid strands is displaced by strand displacement replication of another replicated strand. Formation of replicated strands from the target sequences is favored over formation of replicated strands from non-target sequences.

Also disclosed is a method of amplifying a whole genome, the method comprising exposing cells to alkaline conditions to form a cell lysate, reducing the pH of the cell lysate to form a stabilized cell lysate, and incubating stabilized cell lysate at an elevated temperature in the presence of a thermolabile nucleic acid polymerase having strand displacement activity, an additive, and a set of primers, under conditions promoting replication of the nucleic acids. Replication of the nucleic acids results in replicated strands. During replication at least one of the replicated nucleic acid strands is displaced by strand displacement replication of another replicated strand. Formation of replicated strands from the target sequence is favored over formation of replicated strands from non-target sequences. The cell lysate comprises a whole genome.

Also disclosed is a method of performing strand displacement nucleic acid synthesis at an elevated temperature, the method comprising mixing thermolabile nucleic acid polymerase having strand-displacement activity, nucleic acids comprising target sequences, a set of primers, and an additive, and incubating at an elevated temperature and under conditions favoring hybridization of the primers to the target sequences and extension of the primers by the addition of nucleotides sequentially to the 3' end of the primer in a template-dependent manner, wherein the extension results in replication of the target sequences.

Also disclosed is a method of amplifying a whole genome, the method comprising exposing cells to alkaline conditions to form a cell lysate, wherein the cell lysate comprises a whole genome, reducing the pH of the cell lysate to form a stabilized cell lysate, and incubating stabilized cell lysate at an elevated temperature in the presence of a thermolabile nucleic acid polymerase having strand displacement activity, an additive, a set of primers, and deoxyribonucleotide triphosphates under conditions promoting replication of nucleic acids. During replication at least one of the replicated nucleic acid strands is displaced by strand displacement replication of another replicated strand. Formation of template-dependent extension products in the replication reaction is favored over formation of non-templated product.

Also disclosed is a method of performing strand displacement nucleic acid synthesis at an elevated temperature, the method comprising mixing thermolabile nucleic acid polymerase having strand-displacement activity, single-stranded template nucleic acid, a set of primers, deoxyribonucleotide triphosphates and an additive, and incubating at an elevated temperature and under conditions favoring hybridization of primer to template nucleic acid and extension of primer by the addition of nucleotides sequentially to the 3' end of the primer in a template-dependent manner, wherein said polymerization results in replication of said template nucleic acid.

Also disclosed is a method of amplifying nucleic acids, the method comprising incubating nucleic acids at an elevated temperature in the presence of a thermolabile nucleic acid polymerase having strand displacement activity, an additive, a set of primers, and deoxyribonucleotide triphosphates under conditions promoting replication of nucleic acids. During replication at least one of the replicated nucleic acid strands is displaced by strand displacement replication of another replicated strand. Formation of template-dependent extension products in the replication reaction is favored over formation of non-templated product.

The elevated temperature can be a temperature at which the nucleic acid polymerase is substantially incapable of performing template-dependent polymerization in absence of the additive. The elevated temperature can comprise a temperature at which said polymerase is substantially incapable of performing template-dependent polymerization in absence of said additive. The elevated temperature can be a temperature greater than 30 degrees Celsius. The elevated temperature can be a temperature greater than 32 degrees Celsius. The elevated temperature can be a temperature greater than 35 degrees Celsius. The elevated temperature can be a temperature greater than 37 degrees Celsius. The thermolabile nucleic acid polymerase can be Phi29 DNA polymerase. The thermolabile nucleic acid polymerase can be Phi29 DNA polymerase, *E. coli* DNA polymerase, Bst large fragment DNA polymerase, Bca DNA polymerase, phage M2 DNA polymerase, phage φPRD1 DNA polymerase, Klenow fragment of DNA polymerase I, T5 DNA polymerase, T4 DNA polymerase holoenzyme, or a combination.

The set of primers can comprise at least 2 primers. The set of primers can comprise at least 10 primers. The set of primers can comprise at least 50 primers. The set of primers can comprise greater than 200 primers. The set of primers can comprise greater than 1023 primers. The primers in the set of primers each can be 6 nucleotides in length. The primers in the set of primers each can be 8 nucleotides in length. The primers in the set of primers each can be longer than 8 nucleotides. Two or more of the primers in the set of primers can be of different lengths.

The additive can comprise a sugar or a combination of sugars. The additive can comprise trehalose, glucose, sucrose, or a combination. The additive can comprise a sugar, a chaperone, a protein, or a combination. Strand displacement replication is performed in presence of the additive. The additive can comprise trehalose. The incubation of the nucleic acids, nucleic acid polymerase, additive, and set of primers can be in the presence of deoxyribonucleotide triphosphates.

The ratio of replicated strands from target sequences to replicated strands from non-target sequences is less than the ratio of replicated strands from target sequences to replicated strands from non-target sequences if the nucleic acids are incubated in the presence of the same nucleic acid polymerase and set of primers and under the same conditions except not at an elevated temperature.

Also disclosed is a kit for amplifying nucleic acids, the kit comprising a thermolabile nucleic acid polymerase having strand displacement activity, an additive, and a set of primers, wherein incubating nucleic acids comprising target sequences at an elevated temperature in the presence of the thermolabile nucleic acid polymerase, the additive, and the set of primers under conditions promoting replication of the nucleic acids results in replicated strands and in formation of replicated strands from the target sequences in favor of formation of replicated strands from non-target sequences.

The elevated temperature can be a temperature at which the nucleic acid polymerase is substantially incapable of performing template-dependent polymerization in absence of the additive. The thermolabile nucleic acid polymerase, the additive, and the set of primers can be chosen such that incubating nucleic acids comprising target sequences at an elevated temperature in the presence of the thermolabile nucleic acid polymerase, the additive, and the set of primers under conditions promoting replication of the nucleic acids results in replicated strands and in formation of replicated strands from the target sequences in favor of formation of replicated strands from non-target sequences.

The nucleic acid polymerase can be Phi29 DNA polymerase. The additive can be a sugar, a chaperone, a protein, trehalose, glucose, sucrose, or a combination. The additive can comprise trehalose, the set of primers can comprise exonuclease-resistant random hexamer primers, and the nucleic acid polymerase can comprise Phi29 DNA polymerase. The kit can further comprise one or more components that, when mixed in appropriate amounts, produce a reaction mixture having final concentrations of 10 mM $MgCl_2$, 37.5 mM Tris-HCl, pH 7, 50 mM KCl, 20 mM Ammonium Sulfate, and 1 mM dNTPs. The kit can further comprise any one or a combination of a stabilization solution, a lysis solution, a reaction mix that comprises the set of primers, dithiotheitol, Phosphate-Buffered Saline, and control DNA template. The stabilization solution can comprise 800 mM Tris-HCl, pH 4; the lysis solution can comprise 400 mM KOH, 100 mM dithiothreitol, and 10 mM EDTA; the reaction mix can comprise 150 mM Tris-HCl, 200 mM KCl, 40 mM $MgCl_2$, 20 mM $(NH_4)_2SO_4$, 4 mM deoxynucleotide triphosphates, and 0.2 mM random hexamer primers; the dithiothreitol can comprise 1M dithiothreitol; and the Phosphate-Buffered Saline can comprise 1× Phosphate-Buffered Saline, pH 7.5.

Illustration

The following illustrates some specific modes of the disclosed methods.
High Temperature MDA Protocol
 Reagent Compositions
 Solution A: 400 mM KOH, 10 mM EDTA, pH 8
 Solution B: 800 mM Tris Hydrochloride, pH 4
 1. Denaturation of the genomic DNA template before amplification.
  a. Denaturation Solution Dilute Solution A by 1:4 with $H_2O$ (e.g. 100 μL of Solution A into 300 pt of $H_2O$).
  b. Stabilization Solution Dilute Solution B by 1:5 with $H_2O$ (e.g. 100 μL of Solution B into 400 μL of $H_2O$).
 Note: Denaturation and Stabilization Solutions should be diluted freshly before use. The bottle containing Solution A should be stored tightly sealed.
 2. Add 2.5 μL of the Denaturation Solution to each 0.2 mL thermocycler tube containing 2.5 μL of genomic DNA on ice. Mix well by pipetting up and down 5 times. Incubate the tubes or plate on ice for 3 minutes.
 3. Stop the denaturation reaction after 3 minutes by adding 5 μL of the Stabilization Solution to each sample and control. Remove the tubes from ice. Proceed immediately to the amplification protocol.
 4. Multiple Displacement Amplification
 To the tube from Step 3, add in a final volume of 50 μl:
  Required amount of genomic DNA,
  0.3M Trehalose,
  10 mM $MgCl_2$,
  37.5 mM Tris/HCl pH: 7,
  50 mM KCl,
  20 mM Ammonium Sulfate,
  1 mM dNTPs,
  50 uM exonuclease-resistant random hexamer oligonucleotide,
  40 units of Phi29 DNA polymerase.
 Incubate at 40° C. for 6-16 hrs.

EXAMPLES

A. Example 1

Measurement of DNA Synthesis in MDA Reaction Carried Out at in the Absence of any Additive at 30° C. or in the Presence of 0.3 M Trehalose at 40° C.

Figure 2:
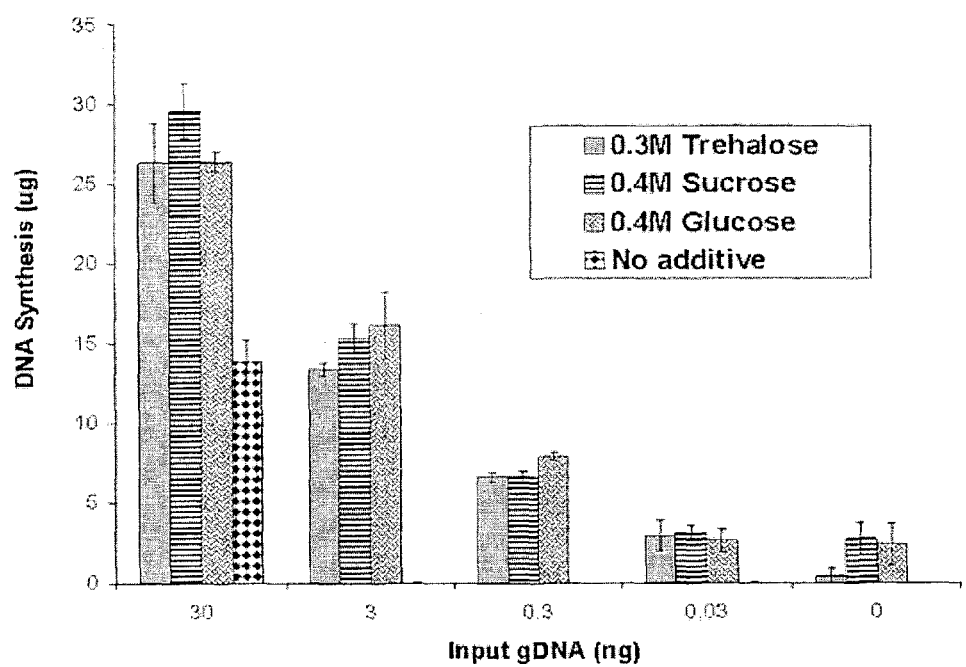
FIG. 2 is a graph of DNA synthesis by MDA reaction carried out at 40° C. in the presence of various sugars for 16 hrs. using varying amounts (0 to 30 ng) of intact genomic DNA as the input template. The MDA reaction was either carried out with no additive or in the presence of 0.3 M Trehalose or 0.4 M Sucrose or 0.4 M Glucose.

MDA reactions were carried out at 30° C. with no additive or at 40° C. with 0.3 M Trehalose, essentially using the protocol described above for high temperature MDA. The quantity of input template was either 0 ng, 0.3 ng, 3 ng, or 30 ng. After 16 hrs of MDA reaction at described temperature, the total DNA synthesis was quantitated by using picogreen assay. The results are shown in FIG. 2.

B. Example 2

Measurement of DNA Synthesis in a 16 hrs. MDA Reaction Carried Out at 40° C. in the Presence of no Additive or 0.3 M Trehalose or 0.4 M Sucrose or 0.4 M Glucose MDA reactions were carried out at 40° C. either with no additive or in the presence of 0.3 M Trehalose or 0.4 M Sucrose or 0.4 M Glucose, essentially using the protocol described above for high temperature MDA. The quantity of input template was either 0 ng or 0.003 ng or 0.03 ng or 0.3 ng or 3 ng or 30 ng. After 16 hrs of MDA reaction, the total DNA synthesis was quantitated by using picogreen assay. The results are shown in FIG. 3.

It is understood that the disclosed invention is not limited to the particular methodology, protocols, and reagents described as these may vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a", "an", and "the" include plural reference unless the context clearly dictates otherwise. Thus, for example, reference to "a nucleic acid polymerase" includes a plurality of such nucleic acid polymerases, reference to "the primer" is a reference to one or more primers and equivalents thereof known to those skilled in the art, and so forth.

Unless defined otherwise, all technical and scientific terms used herein have the same meanings as commonly understood by one of skill in the art to which the disclosed invention belongs. Although any methods and materials similar or equivalent to those described herein can be used in the practice or testing of the present invention, the preferred methods, devices, and materials are as described. Publications cited herein and the material for which they are cited are specifically incorporated by reference. Nothing herein is to be construed as an admission that the invention is not entitled to antedate such disclosure by virtue of prior invention.

Those skilled in the art will recognize, or be able to ascertain using no more than routine experimentation, many equivalents to the specific embodiments of the invention described herein. Such equivalents are intended to be encompassed by the following claims.

I claim:

1. A method of amplifying nucleic acids, the method comprising,
incubating nucleic acids comprising target sequences at an elevated temperature in the presence of a thermolabile nucleic acid polymerase having strand displacement activity, an additive, and a set of primers, under conditions promoting replication of the nucleic acids, wherein replication of the nucleic acids results in replicated strands, wherein during replication at least one of the replicated nucleic acid strands is displaced by strand displacement replication of another replicated strand, wherein replication is conducted at a constant temperature,
wherein formation of replicated strands from the target sequences is favored over formation of replicated strands from non-target sequences.

2. The method of claim 1 wherein the elevated temperature is a temperature at which the nucleic acid polymerase is notably inactivated from performing template-dependent polymerization in absence of the additive.

3. The method of claim 2 wherein the elevated temperature is a temperature greater than 30 degrees Celsius.

4. The method of claim 2 wherein the elevated temperature is a temperature greater than 32 degrees Celsius.

5. The method of claim 2 wherein the elevated temperature is a temperature greater than 35 degrees Celsius.

6. The method of claim 2 wherein the elevated temperature is a temperature greater than 37 degrees Celsius.

7. The method of claim 1 wherein the set of primers comprises at least 2 primers.

8. The method of claim 1 wherein the set of primers comprises at least 10 primers.

9. The method of claim 1 wherein the set of primers comprises at least 50 primers.

10. The method of claim 1 wherein the set of primers comprises greater than 200 primers.

11. The method of claim 1 wherein the set of primers comprises greater than 1023 primers.

12. The method of claim 1 wherein the primers in the set of primers are each 6 nucleotides in length.

13. The method of claim 1 wherein the primers in the set of primers are each 8 nucleotides in length.

14. The method of claim 1 wherein the primers in the set of primers are each longer than 8 nucleotides.

15. The method of claim 1 wherein two or more of the primers in the set of primers are of different lengths.

16. The method of claim 1 wherein the additive comprises a sugar or a combination of sugars.

17. The method of claim 16 wherein the additive comprises trehalose, glucose, sucrose, or a combination.

18. The method of claim 1 wherein the additive comprises a sugar, a chaperone, a protein, or a combination.

19. The method of claim 1 wherein strand displacement replication is performed in presence of the additive.

20. The method of claim 19 wherein the additive comprises trehalose.

21. The method of claim 1 wherein the incubation of the nucleic acids, nucleic acid polymerase, additive, and set of primers is in the presence of deoxyribonucleotide triphosphates.

22. The method of claim 1 wherein the ratio of replicated strands from target sequences to replicated strands from non-target sequences is less than the ratio of replicated strands from target sequences to replicated strands from non-target sequences if the nucleic acids are incubated in the presence of the same nucleic acid polymerase and set of primers and under the same conditions except not at an elevated temperature.

23. The method of claim 1 wherein the elevated temperature is a temperature at or above which the nucleic acid polymerase is notably inactivated in the absence of the additive, dNTPs, and template nucleic acid.

24. The method of claim 1 wherein the elevated temperature is a temperature at or above which the nucleic acid polymerase is substantially inactivated in the absence of the additive, dNTPs, and template nucleic acid.

25. The method of claim 1 wherein the elevated temperature is a temperature at or above which the nucleic acid polymerase is significantly inactivated in the absence of the additive, dNTPs, and template nucleic acid.

26. A method of amplifying a whole genome, the method comprising,
exposing cells to alkaline conditions to form a cell lysate, wherein the cell lysate comprises a whole genome,
reducing the pH of the cell lysate to form a stabilized cell lysate, and
incubating stabilized cell lysate at an elevated temperature in the presence of a thermolabile nucleic acid polymerase having strand displacement activity, an additive, and a set of primers, under conditions promoting replication of the nucleic acids, wherein replication of the nucleic acids results in replicated strands, wherein during replication at least one of the replicated nucleic acid strands is displaced by strand displacement replication of another replicated strand,
wherein formation of replicated strands from the target sequence is favored over formation of replicated strands from non-target sequences.

27. A method of performing strand displacement nucleic acid synthesis at an elevated temperature, the method comprising,
mixing thermolabile nucleic acid polymerase having strand-displacement activity, nucleic acids comprising target sequences, a set of primers, and an additive and
incubating at an elevated temperature and under conditions favoring hybridization of the primers to the target sequences and extension of the primers by the addition of nucleotides sequentially to the 3' end of the primer in a template-dependent manner, wherein the extension results in replication of the target sequences.

28. The method of claim 1, wherein generation of high molecular weight artifacts during the incubation is reduced as compared to generation of high molecular weight artifacts in a similar incubation not at the elevated temperature and not in the presence of the additive.

* * * * *